US007087750B2

(12) United States Patent
Caldirola et al.

(10) Patent No.: US 7,087,750 B2
(45) Date of Patent: Aug. 8, 2006

(54) COMPOUNDS, THEIR USE AND PREPARATION

(75) Inventors: Patrizia Caldirola, Uppsala (SE); Björn M. Nilsson, Uppsala (SE); Gary Johansson, Uppsala (SE)

(73) Assignee: Biovitrum AB (SE)

( * ) Notice: Subject to any disclaimer, the term of this patent is extended or adjusted under 35 U.S.C. 154(b) by 0 days.

(21) Appl. No.: 10/037,110

(22) Filed: Oct. 22, 2001

(65) Prior Publication Data
US 2002/0165251 A1 Nov. 7, 2002

Related U.S. Application Data

(60) Provisional application No. 60/243,115, filed on Oct. 25, 2000.

(30) Foreign Application Priority Data
Oct. 20, 2000 (SE) .................................. 0003810

(51) Int. Cl.
C07D 403/04 (2006.01)
C07D 471/04 (2006.01)
C07D 471/06 (2006.01)
A61K 31/496 (2006.01)
A61P 25/24 (2006.01)

(52) U.S. Cl. ..................... 540/575; 544/349; 544/373; 546/133; 548/466; 548/509; 514/218; 514/249; 514/253.09; 514/305; 514/414; 514/415

(58) Field of Classification Search ................ 514/218, 514/249, 253.09, 305, 414, 415; 540/575; 544/349, 373; 546/133; 548/466, 509
See application file for complete search history.

(56) References Cited

U.S. PATENT DOCUMENTS

| 6,133,287 A | 10/2000 | Slassi et al. ................ 514/318 |
| 6,251,893 B1 * | 6/2001 | Maddaford et al. .... 514/214.01 |
| 2002/0115670 A1 | 8/2002 | Kelly et al. ............ 514/253.05 |
| 2003/0045527 A1 * | 3/2003 | Briggs et al. .......... 514/254.09 |

FOREIGN PATENT DOCUMENTS

| EP | 0812826 A1 | 12/1997 |
| EP | 0 909 762 A2 | 4/1999 |
| WO | 92/13856 | 8/1992 |
| WO | WO 9213856 A1 | 8/1992 |
| WO | 96/03400 | 2/1996 |
| WO | WO 96/33171 A1 * | 10/1996 |
| WO | WO 9633171 A1 | 10/1996 |
| WO | WO 9636611 A1 | 11/1996 |
| WO | WO 9805315 A1 | 2/1998 |
| WO | 99/47516 | 9/1999 |
| WO | WO 9947516 A1 | 9/1999 |
| WO | 99/65906 | 12/1999 |
| WO | WO 9965492 A1 | 12/1999 |
| WO | WO 9965906 A1 | 12/1999 |
| WO | 00/34242 | 6/2000 |
| WO | WO 0232863 A1 | 4/2002 |
| WO | WO 02 41889 A2 | 5/2002 |
| WO | WO 0236562 A2 | 5/2002 |

OTHER PUBLICATIONS

Illi, Volker O., Synthesis (2), 136 (German) 1979.*
Nyasse, Barthelemy; Grehn, Leif; Maia, Hernani L. S.; Monteiro, Luis S.; Ragnarsson, Ulf, Journal of Organic Chemistry, 64(19), 7135-7139, 1999.*
Goulaouic-Dubois, Catherine; Guggisberg, Armin; Hesse, Manfred, Journal of Organic Chemistry, 60(18), 5969-72 (English) 1995.*
U.S. Appl. No. 60/245,118, filed Nov. 2000, Kelly et al.*
U.S. Appl. No. 60/298,834, Jun. 2001, Clark et al.*
Bioorganic & Medicinal Chemistry Letters, vol. 10, No. 15, cover only.*
Robichaud, A.J. et al, Ann. Reports Med. Chem., vol. 35, 2000, 11-19.*
Dourish CT, Obes Res. Nov. 1995; 3 Suppl 4: 449S-462S, cited in Medline, Abstract PMID: 8697043.*
Lindner, Mark D. et al JPET 307:682-691, 2003.*
CAPLUS accession No. 1993:539117, Abstract Only.
CAPLUS accession No. 1996:736044, Abstract Only.
CAPLUS accession No. 1998:724128, Abstract Only.
CAPLUS accession No. 1993:495527, Abstract Only.
CAPLUS accession No. 1993:147461, Abstract Only.
CAPLUS accession No. 1999:550761, Abstract Only.
CAPLUS accession No. 1986:110010, Abstract Only.
CAPLUS accession No. 1979:450235, Abstract Only.
CAPLUS accession No. 1982:562734, Abstract Only.
CAPLUS accession No. 1986:186352, Abstract Only.
CAPLUS accession No. 1987:156217, Abstract Only.
CAPLUS accession No. 1993:101757, Abstract Only.
CAPLUS accession No. 1995:751092, Abstract Only.
CAPLUS accession No. 1998:265011, Abstract Only.

(Continued)

Primary Examiner—Thomas C. McKenzie
(74) Attorney, Agent, or Firm—Fish & Richardson P.C.

(57) ABSTRACT

The invention provides 2, 3-, 4- or 5-substituted-N1-(arylsulfonyl)indole and (heteroaryl)indole compounds of the general formula (I):

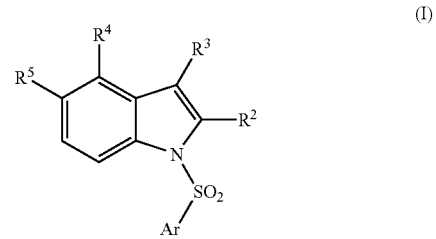

in which Ar, $R^2$, $R^3$, $R^4$ and $R^5$ are as defined in the specification. The compounds bind to the 5-$HT_6$ receptor and are useful for the treatment and prophylaxis of disorders mediated by the 5-$HT_6$ receptor, such as obesity and CNS disorders.

75 Claims, No Drawings

OTHER PUBLICATIONS

Isaac et al., "6-Bicyclopiperazinyl-1-arylsulfonylindoles and 6-Bicyclopiperidinyl-1-arylsulfonylindoles . . . ", 2000, Bioorganic & Medicinal Chem. Letters, vol. 10;1719-1721.

Tsai et al., "N1-(Benzenesulfonyl)tryptamines as Novel 5-HT6 Antagonists", 2000, Bioorganic & Medicinal Chem. Letters, vol. 10;2295-2299.

CAPLUS accession No. 1999:661842.

CAPLUS accession No. 1998:710510.

CAPLUS accession No. 1999:235586.

CAPLUS accession No. 2001:419497.

CAPLUS accession No. 2001:466985.

Lee et al., "5-HT6 Serotonin Receptor Binding Affinities of N1-Benzenesulfonyl . . . ", 2000, Med. Chem, Res., vol. 10(4);230-242.

Tsai, et al. $N_1$-*(Benzenesulfonyl)tryptamines as Novel 5-HT$_6$ Antagonists*. Bioorganic & Medicinal Chemistry Letters, vol. 10, No. 4, 2000, pp. 2295-2299.

Lee, et al. *5-HT$_6$ Serotonin Receptor Binding Affinites of $N_1$-Benzenesulfonyl and Related Tryptamines*. Medicinal Chemistry Research, vol. 10, No. 4, 2000, pp. 230-242.

Bentley et al., "5-HT6 antisense oligonucleotide ICV affects rat performance in the water maze and feeding." J Psychopharmacol Suppl A64, 1997, 255.

Bentley et al., "Effect of 5-HT6 antagonist Ro 04-6790 on food consumption in rats trained to a fixed feeding regime." Br J Pharmacol. 1999 Suppl. 126, P66.

Hirst, "5-HT6 receptor and clinical positibilities, S12.2" *Neuroscience in Orlando* (Oct. 31-Nov. 10, 2002).

Meneses, "5-HT system and cognition", *Neurosci. Biobehav. Pharm.* 23:1111-1125 (1999).

Rogers et al., Cognitive Enhancement Effect of Selective 5-HT$_6$ antagonist SB 271046, *Br. J. Pharmac.*, 17:22P (1999).

Ruat et al. Biochem. Biophys. Res. Commun. 1993, 193 (1) 268-276.

Sakamoto, et al. Condensed heteroaromatic ring systems. XIII. One-step synthesis of 2-substituted 1-methylsulfonylindoles from N-(2-halophenyl)methanesulfonamides. Chem. Pharm. Bull., 1988, vol. 36, No. 4, pp. 1305-1308.

Sebben et al., NeuroReport 5, 2553-2557 (1994).

Williams et al., Annual Reports in Medicinal chemistry, D. Robertson, ed., vol. 36, pp. 1-5, Academic Press (2001).

* cited by examiner

COMPOUNDS, THEIR USE AND PREPARATION

CROSS REFERENCE TO RELATED APPLICATIONS

This application claims priority from Swedish Patent Application No. 0003810-9, filed Oct. 20, 2000, and U.S. Provisional Patent Application No. 60/243,115, filed Oct. 25, 2000. These applications are incorporated herein by reference in their entirety.

TECHNICAL FIELD

The present invention relates to novel 2–3-, 4- or 5-substituted-N1-(arylsulfonyl)indole compounds and (heteroarylsulfonyl)indole compounds, to pharmaceutical compositions comprising the compounds and to the use of the compounds for the preparation of a medicament for the treatment of obesity and CNS disorders as well as method of treatment of these disorders.

BACKGROUND ART

Obesity is a condition characterized in an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and NIDDM (type II diabetes). Searching for compounds, which reduce body weight has been going on for many decades. One line of research has been activation of serotonergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulate a wide range of physiological and pathological functions, including anxiety, sleep regulation, aggression, feeding and depression. Multiple serotonin receptor subtypes have been identified and cloned. One of these, the 5-HT$_6$ receptor, was cloned by several groups in 1993 (M Ruat, E Traiffort, J-M Arrang, J Tardivel-Lacombe, J Diaz, R Leurs, J-C Shwartz. *Biochem. Biophys. Res. Commun.* 1993, 193 (1) 268–276; M Sebben, H Ansanay, J Bockaert, A Dumuis, *NeuroReport* 5, 2553–2557 (1994).) This receptor is positively coupled to adenylyl cyclase and displays affinity for antipsychotics such as clozapine. Recently, the effect of 5-HT$_6$ antagonist and 5-HT$_6$ antisense oligonucleotides to reduce food intake in rats has been reported (J C Bentley, C A Mardsen, A J Sleight and K C Fone. Effect of 5-HT$_6$ antagonist Ro 04-6790 on food consumption in rats trained to a fixed feeding regime. *Br J Pharmacol.* 1999 Suppl. 126, P66; J C Bentley, A J Sleight, C A Mardsen, K C F Fone. 5-HT$_6$ antisense oligonucleotide ICV affects rat performance in the water maze and feeding. *J Psychopharmacol Suppl A* 64, 1997, 255).

Compounds with enhanced affinity and selectivity for the 5-HT$_6$ receptor have been identified, e.g. in WO 00/34242 and by M. Isaac, A. Slassi, T. Xin, N. MacLean, J. Wilson, K. McCallum, H. Wang and L. Demchyshyn: 6-Bicyclopiperazinyl-1-arylsulfonylindoles and 6-Bicyclopiperidinyl-1-arylsulfonylindoles derivatives as novel, potent and selective 5-HT$_6$ receptor antagonists; *Bioorganic & Medicinal Chemistry Letters* 2000, 10, 1719–1721.

DETAILED DESCRIPTION OF THE INVENTION

According to the present invention it has been found that the compounds of formula (I) show affinity for the 5-HT$_6$ receptor as antagonists at a low nanomolar range. The 5-HT$_6$ antagonist compounds of the present invention are useful for the treatment or prophylaxis of obesity and for the treatment or prophylaxis of memory and CNS disorders (schizophrenia, Parkinson's disease and depression), Attention Deficit Hyperactive Disorders (ADHD), and drug abuse.

According to the invention, a compound of the general formula (I) is provided:

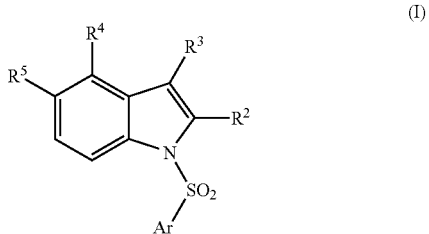

(I)

wherein

Ar is
(1) phenyl,
(2) naphthyl,
(3) a 5- to 10-membered monocyclic or bicyclic heterocyclic ring having 1 to 4 heteroatoms selected from the group consisting of oxygen, sulfur, or nitrogen, or
(4) —R$^9$-phenyl;

wherein the phenyl, naphthyl, or heterocyclic ring is optionally substituted with halogen, C$_{1-6}$ alkyl, CF$_3$, hydroxyl, C$_{1-6}$ alkoxyl, OCF$_3$, COCF$_3$, CN, NO$_2$, phenyloxy, phenyl, C$_{1-6}$ alkylsulfonyl, C$_{2-6}$ alkenyl, —NR$^7$R$^8$, C$_{1-6}$ alkylcarboxyl, formyl, —C$_{1-6}$ alkyl-NH—CO-phenyl, —C$_{1-6}$ alkyl-CO—NH-phenyl, —NH—CO—C$_{1-6}$ alkyl, —CO—NR$^7$R$^8$, or SR$^7$; wherein each of R$^7$ and R$^8$ is independently H or C$_{1-6}$ alkyl; and R$^9$ is C$_{1-6}$ alkyl or C$_{2-6}$ alkenyl, either of which is optionally substituted with phenyl or phenyloxy;

R$^2$ is H, phenyl, I, or C$_{1-6}$ alkyl;
R$^3$ is H or 3-(1-azabicyclo[2.2.2]oct-2-en)yl;
R$^4$ is H or is selected from the group consisting of:

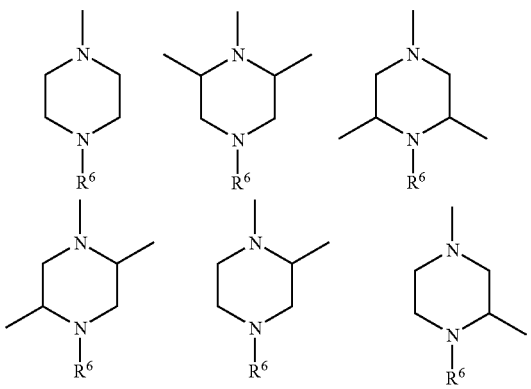

-continued

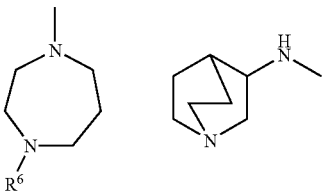
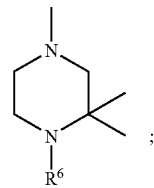

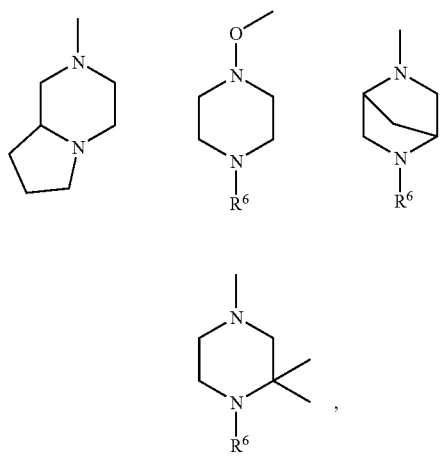
and wherein R⁶ is H, C$_{1-6}$ alkyl, or benzyl; and
R⁵ is H, hydroxy, C$_{1-3}$ alkoxy, F, NO$_2$, CF$_3$, OCF$_3$, or is selected from the group consisting of:

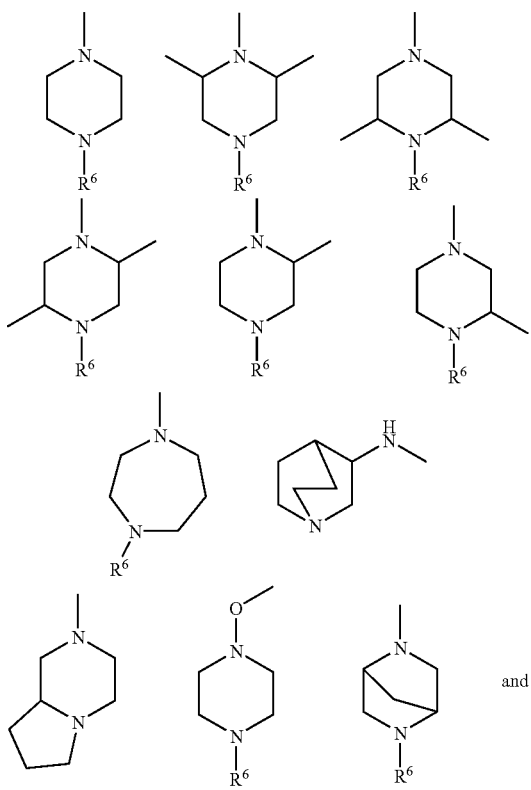

-continued

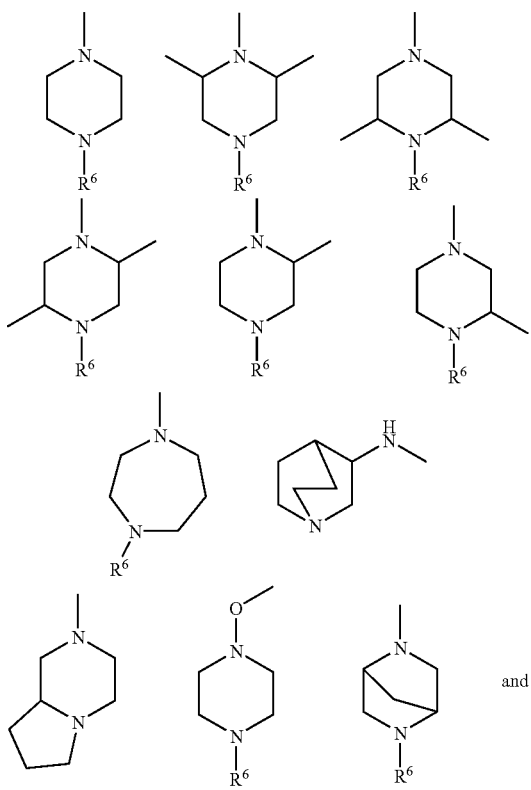
;

or a pharmaceutically acceptable salt, hydrate, or stereoisomer thereof, with the proviso that when R² is alkyl, R⁴ is not H.

The term "C$_{1-6}$ alkyl" denotes a straight or branched alkyl group having from 1 to 6 carbon atoms. Examples of alkyl include methyl, ethyl, n-propyl, iso-propyl, n-butyl, iso-butyl, sec-butyl, t-butyl and straight- and branched-chain pentyl and hexyl.

The term "alkenyl" refers to a straight or branched hydrocarbon chain containing 2 to 6 carbon atoms and one or more (e.g., 1, 2, or 3) double or triple bonds, respectively. Some examples of alkenyl are allyl, 2-butenyl, 2-pentenyl, and 2-hexenyl.

The term "C$_{1-6}$ alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

The term "halogen" shall mean fluorine, chlorine, bromine or iodine. The term "heterocyclic ring" refers to a cyclic moiety of the indicated size and having 1–4 heteroatoms (ring atoms) selected from the group consisting of nitrogen, oxygen, and sulfur. A heterocyclic ring can be completely saturated, partially saturated, or unsaturated. In other words, a heterocyclic ring can be a heterocycloalkyl, heterocycloalkenyl (containing one or more double bonds) or heteroaryl and may contain fused rings. Examples of a heterocyclic ring include piperidinyl, piperazinyl, tetrahydropyranyl, tetrahydrofuryl, morpholinyl, pyridyl, furanyl, pyrrolyl, thienyl, thiazolyl, oxazolyl, imidazolyl, indolyl, benzofuranyl, and benzthiazolyl. When appropriate, the nitrogen ring atoms of a heterocyclic ring can be —NH—, —N(C$_{1-6}$ alkyl)-, or —N(—CO—CF$_3$)—.

In a preferred embodiment, the invention features a compound of formula (I), supra, wherein Ar is (1) phenyl that is unsubstituted or optionally mono- or poly-substituted with halogen, C$_{1-6}$ alkyl, CF$_3$, hydroxyl, C$_{1-6}$ alkoxyl, OCF$_3$, CN, NO$_2$, phenyloxyl, phenyl, alkylsulfonyl, C$_{1-6}$ alkenyl, —NH$_2$, —NHR⁷, —NR⁷R⁸, C$_{1-6}$ alkylcarboxyl, formyl, —NH—CO—C$_{1-6}$ alkyl, —CO—NR⁷R⁸, or SR⁷ wherein each of R⁷ and R⁸ is independently H or C$_{1-6}$ alkyl;

(2) 1-naphthyl or 2-naphthyl that is unsubstituted or optionally mono- or poly-substituted with halogen, C$_{1-6}$ alkyl, CF$_3$, hydroxyl, C$_{1-6}$ alkoxyl, OCF$_3$, CN, NO$_2$, phenyloxyl, phenyl, alkylsulfonyl, C$_{1-6}$ alkenyl, —NH$_2$, —NHR⁷, —NR⁷R⁸, C$_{1-6}$ alkylcarboxyl, formyl, —NH—CO—C$_{1-6}$ alkyl, —CO—NR⁷R⁸, or SR⁷ wherein each of R⁷ and R⁸ is independently H or C$_{1-6}$ alkyl;

(3) cynnamoyl;

(4) benzyl;

(5) 1,1-diphenylethyl;

(6) a monocyclic or bicyclic heterocyclic ring selected from the group consisting of furyl, pyrrolyl, triazolyl, diazolyl, oxazolyl, thiazolyl, oxadiazolyl, isothiazolyl, isoxazolyl, thiadiazolyl, pyrimidyl, pyrazinyl, thienyl, imidazolyl, pyrazolyl, indolyl, quinolinyl, isoquinolinyl, benzofuryl, benzothienyl, and benzoxadiazolyl, said heterocyclic ring being optionally mono- or di-substituted substituted with halogen or $C_{1-6}$ alkyl;

$R^4$ is H or is selected from the group consisting of:

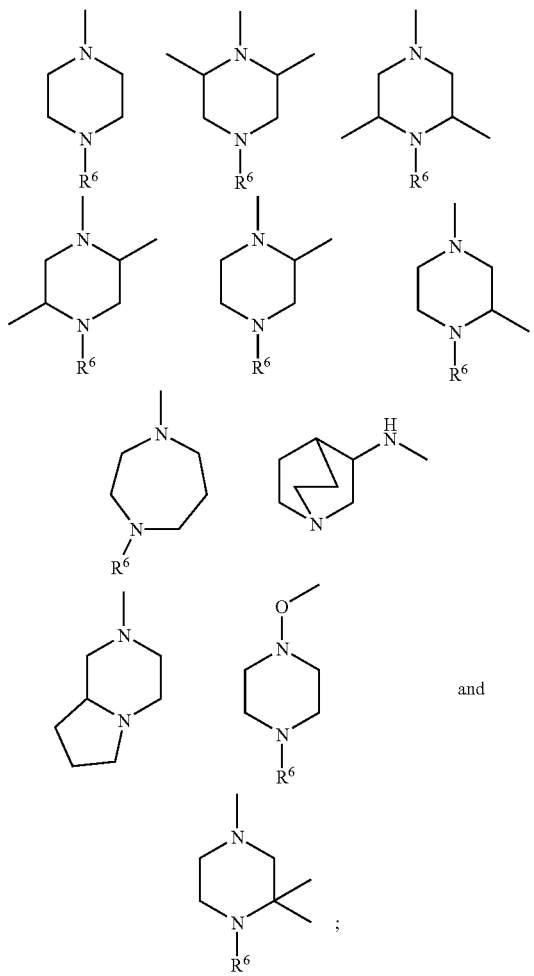

wherein $R^6$ is H, $C_{1-6}$ alkyl, or benzyl; and $R^5$ is H, hydroxy, $C_{1-3}$ alkoxy, F, $NO_2$, $CF_3$, $OCF_3$ or is selected from the group consisting of:

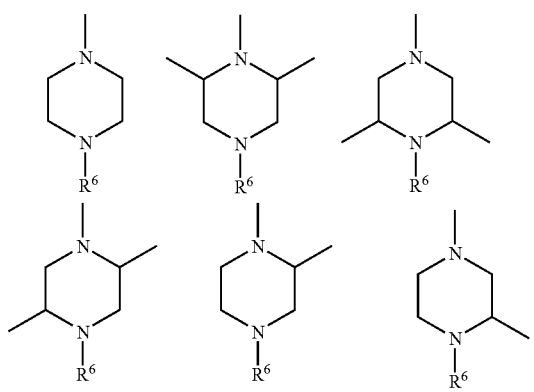

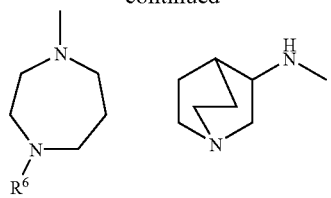

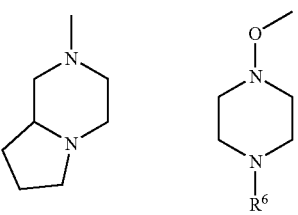

and

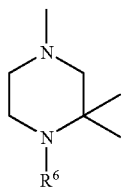

In another preferred embodiment, the invention features a compound of formula (I), supra, wherein Ar is
(1) phenyl,
(2) 1-naphthyl or 2-naphthyl,
(3) a 5- to 10-membered monocyclic or bicyclic heterocyclic ring having 1 to 4 heteroatoms selected from the group consisting of oxygen, sulfur, or nitrogen, or
(4) —$R^9$-phenyl;

wherein the phenyl, naphthyl, or heterocyclic ring is optionally substituted with F, Cl, Br, $C_{1-6}$ alkyl, $CF_3$, hydroxyl, $C_{1-6}$ alkoxyl, $OCF_3$, phenyl, $C_{2-6}$ alkenyl, —$NR^7R^8$, —NH—CO—$C_{1-6}$ alkyl, or $SR^7$, wherein each of $R^7$ and $R^8$ is independently H or $C_{1-6}$ alkyl; and $R^9$ is $C_{1-2}$ alkyl;

$R^2$ is H, phenyl, I, or $C_{1-6}$ alkyl;

$R^4$ is selected from the group consisting of:

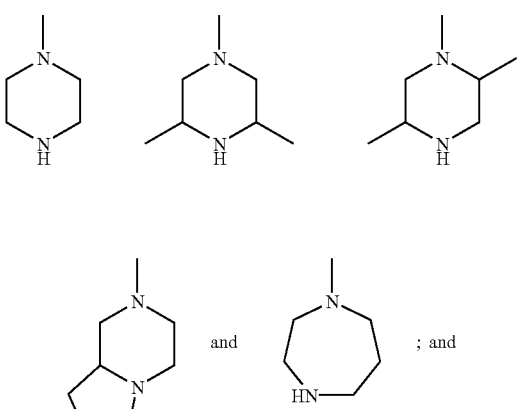

$R^5$ is $C_{1-3}$ alkoxy or a heterocyclic ring selected from the group consisting of:

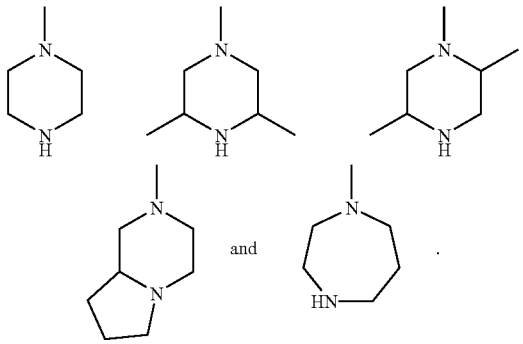

and

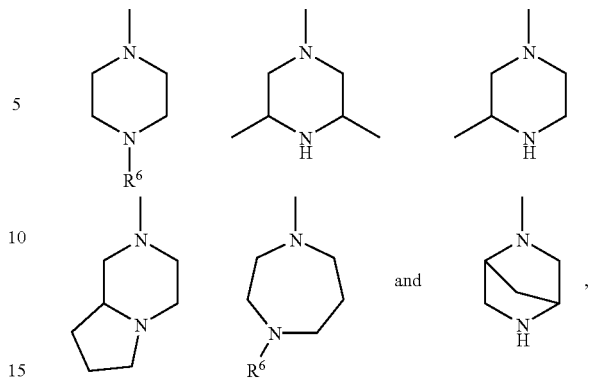

wherein $R^6$ is H, $C_{1-3}$ alkyl, or benzyl.

Further preferred embodiments of the present invention are provided below.

(1) Compounds of formula (I), supra, wherein wherein Ar is phenyl, optionally substituted with F, Cl, Br, methyl, $CF_3$, $C_{1-4}$ alkoxyl, $OCF_3$, CN, $NO_2$, phenyloxy, phenyl, methylsulfonyl, or —$NR^7R^8$, where each of $R^7$ and $R^8$ is independently H or methyl.

(2) Compounds of formula (I), supra, wherein Ar is 1-naphthyl or 2-naphthyl, each of which is optionally substituted with F, Cl, Br, methyl, $CF_3$, $C_{1-4}$ alkoxyl, $OCF_3$, CN, $NO_2$, phenyloxy, phenyl, methylsulfonyl, or —$NR^7R^8$, where each of $R^7$ and $R^8$ is independently H or methyl.

(3) Compounds of formula (I), supra, wherein Ar is a heterocyclic ring selected from the group consisting of furyl, pyrrolyl, triazolyl, diazolyl, oxazolyl, thiazolyl, oxadiazolyl, isothiazolyl, isoxazolyl, thiadiazolyl, pyridinyl, pyrimidyl, pyrazinyl, thienyl, imidazolyl, pyrazolyl, indolyl, quinolinyl, isoquinolinyl, benzofuryl, benzothienyl, and benzoxadiazolyl, each of which is optionally substitiued with halogen, $C_{1-6}$ alkyl, $CF_3$, hydroxyl, $C_{1-6}$ alkoxyl, $OCF_3$, CN, $NO_2$, phenyloxy, phenyl, $C_{1-6}$ alkylsulfonyl, $C_{2-6}$ alkenyl, —$NR^7R^8$, $C_{1-6}$ alkylcarboxyl, formyl, —NH—CO—$C_{1-6}$ alkyl, —CO—$NR^7R^8$, or $SR^7$; wherein each of $R^7$ and $R^8$ is independently H or $C_{1-6}$ alkyl.

(4) Compounds of formula (I), supra, wherein Ar is a heterocyclic ring selected from the group consisting of pyridinyl, thienyl, imidazolyl, pyrazolyl, benzothienyl, and benzoxadiazolyl, each of which is optionally substituted with halogen or $C_{1-6}$ alkyl.

(5) Compounds of formula (I), supra, wherein Ar is 2-pyridyl, 3-pyridyl, or 4-pyridyl.

(6) Compounds of formula (I), supra, wherein Ar is a 5- to 7-membered aromatic, partially saturated, or completely saturated heterocyclic ring having 1 to 4 heteroatoms selected from the group consisting of O, S, or $NR^{10}$, where $R^{10}$ is H, $C_{1-6}$ alkyl, —CO—$CF_3$, or absent.

(7) Compounds of formula (I), supra, wherein Ar is —$R^9$-phenyl, wherein $R^9$ is $C_{1-3}$ alkyl or $C_{2-3}$ alkenyl, either of which is optionally substituted with phenyl or phenyloxy, each phenyl being optionally substituted with F, Cl, Br, methyl, $CF_3$, $C_{1-4}$ alkoxyl, $OCF_3$, CN, $NO_2$, phenyloxy, phenyl, methylsulfonyl, or —$NR^7R^8$; and each of $R^7$ and $R^8$ being independently H or $C_{1-6}$ alkyl.

Further preferred embodiments of the present invention include compounds of formula (I), supra, wherein each of $R^2$ and $R^3$ is H; and compounds of formula (I), supra, wherein each of $R^4$ and $R^5$ is independently H or a heterocyclic ring selected from the group consisting of:

Some preferred compounds of the invention are:
1-(phenylsulfonyl)-4-(1-piperazinyl)-1H-indole,
1-[(4-fluorophenyl)sulfonyl]-4-(1-piperazinyl)-1H-indole,
1-[(5-chloro-3-methyl-1-benzothien-2-yl)sulfonyl]-4-(1-piperazinyl)-1H-indole,
3-(1-azabicyclo[2.2.2]oct-2-en-3-yl)-1-(phenylsulfonyl)-1H-indole
5-methoxy-1-(phenylsulfonyl)-4-(1-piperazinyl)-1H-indole,
4-(4-ethyl-1-piperazinyl)-1-(phenylsulfonyl)-1H-indole,
1-[(4-methylphenyl)sulfonyl]-4-(4-methyl-1-piperazinyl)-1H-indole,
1-(phenylsulfonyl)-5-(1-piperazinyl)-1H-indole,
4-(2,5-dimethyl-1-piperazinyl)-1-(phenylsulfonyl)-1H-indole,
4-(2,6-dimethyl-1-piperazinyl)-1-(phenylsulfonyl)-1H-indole,
4-(1,4-diazepan-1-yl)-1-(phenylsulfonyl)-1H-indole,
2-[1-(phenylsulfonyl)-1H-indol-4-yl]octahydropyrrolo[1,2-a]pyrazine 1-(2-naphthylsulfonyl)-4-(1-piperazinyl)-1H-indole,
1-(1-naphthylsulfonyl)-4-(1-piperazinyl)-1H-indole,
1-[(4-methylphenyl)sulfonyl]-4-(1-piperazinyl)-1H-indole,
N-(1-Azabicyclo[2.2.2]oct-3-yl)-N-{1-[(4-methylphenyl)sulfonyl]-1H-indol-4-yl}amine,
2-Ethyl-4-(4-ethyl-1-piperazinyl)-1-[(phenyl)sulfonyl]-1H-indole,
2-ethyl-1-(4-methyl-phenylsulfonyl)-4-(1-piperazinyl)-1H-indole,
4-(2,5-dimethyl-1-piperazinyl)-2-ethyl-1-(phenylsulfonyl)-1H-indole,
4-(4-ethyl-1-piperazinyl)-5-fluoro-1-[(4-methylphenyl)sulfonyl]-1H-indole,
5-fluoro-4-(1-piperazinyl)-1-{[4-(trifluoromethyl)phenyl]sulfonyl}-1H-indole,
5-chloro-1-phenylsulfonyl)-4-(1-piperazinyl)-1H-indole,
5-chloro-1-(phenylsulfonyl)-4-(1-piperazinyl)-1H-indole,
1-[(5-chloro-3-methyl-1-benzothien-2-yl)sulfonyl]-5-methoxy-4-(1-piperazinyl)-1H-indole,
1-[(5-chloro-3-methyl-1-benzothien-2-yl)sulfonyl]-5-(1-piperazinyl)-1H-indole,
1-[(4-methylphenyl)sulfonyl]-4-(3-methyl-1-piperazinyl)-1H-indole,
1-[(4-methylphenyl)sulfonyl]-4-(4-piperidinyloxy)-1H-indole, and
1-[(4-methylphenyl)sulfonyl]-4-(3-methyl-1-piperazinyl)-1H-indole.

Most preferred embodiments of the invention are the compounds
1-(phenylsulfonyl)-4-(1-piperazinyl)-1H-indole hydrochloride,
1-[(2,5-dimethoxyphenyl)sulfonyl]-4-(1-piperazinyl)-1H-indole hydrochloride, and 4-(1-piperazinyl)-1-(3-pyridinylsulfonyl)-1H-indole hydrochloride.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated from each other by conventional methods. Any given isomer may be obtained by stereospecific or asymmetric synthesis. The invention also extends to any tautomeric forms and mixtures thereof.

The compounds of the formula (I) can form acid addition salts with acids such as conventional pharmaceutically acceptable acids, for example maleic, hydrochloric, hydrobromic, phosphoric, acetic, fumaric, salicylic, citric, lactic, mandelic, tartaric and methanesulfonic.

Compounds of formula (I) may also form solvates such as hydrates and the invention also extends to these forms. When referred to herein, it is understood that the term "compound of formula (I)" also includes these forms.

The compounds according to formula (I) can conveniently be administered in a pharmaceutical composition containing the compound in combination with pharmacologically and pharmaceutically acceptable carriers. Such pharmaceutical compositions can be prepared by methods and contain carriers or excipients which are well known in the art. A generally recognized compendium of such methods and ingredients is Remington's Pharmaceutical Sciences by E.W. Martin (Mark Publ. Co., 15$^{th}$ Ed., 1975). The compounds and compositions can be administered orally, parenterally (for example, by intravenous, intraperitoneal or intramuscular injection), transdermally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously, or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound can be administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may be presented in a single dose or as divided doses administered at appropriate intervals.

The compositions can be administered orally, sublingually, transdermally, or parenterally at dose levels of about 0.01 to about 150 mg/kg, preferably about 0.1 to about 50 mg/kg, and more preferably about 0.1 to about 30 mg/kg of mammal body weight.

TABLE I

Compounds prepared according to synthetic schemes 1 or 2.
All compounds in Table I are hydrochlorides salts.

| EXAMPLE | —SO$_2$—Ar | R$^4$ |
|---|---|---|
| (7) 1-(phenylsulfonyl)-4-(1-piperazinyl)-1H-indole | phenylsulfonyl | piperazinyl |

TABLE I-continued

Compounds prepared according to synthetic schemes 1 or 2.
All compounds in Table I are hydrochlorides salts.

| EXAMPLE | —SO₂—Ar | R⁴ |
|---|---|---|
| (8) 1-[(2,5-dimethoxyphenyl)sulfonyl]-4-(1-piperazinyl)-1H-indole | 2,5-dimethoxyphenylsulfonyl | 1-piperazinyl |
| (9) 1-(mesitylsulfonyl)-4-(1-piperazinyl)-1H-indole | mesitylsulfonyl | 1-piperazinyl |
| (10) 1-(1-naphthylsulfonyl)-4-(1-piperazinyl)-1H-indole | 1-naphthylsulfonyl | 1-piperazinyl |
| (11) N,N-dimethyl-N-(5-{[4-(1-piperazinyl)-1H-indol-1-yl]sulfonyl}-1-naphthyl)amine | 5-(dimethylamino)-1-naphthylsulfonyl | 1-piperazinyl |
| (12) 1-[(4-Propoxyphenyl)sulfonyl]-4-(1-piperazinyl)-1H-indole | 4-propoxyphenylsulfonyl | 1-piperazinyl |
| (13) 1-[(2,5-Dichloro-3-thienyl)sulfonyl]-4-(1-piperazinyl)-1H-indole hydrochloride | 2,5-dichloro-3-thienylsulfonyl | 1-piperazinyl |

TABLE I-continued

Compounds prepared according to synthetic schemes 1 or 2.
All compounds in Table I are hydrochlorides salts.

| EXAMPLE | —SO₂—Ar | R⁴ |
|---|---|---|
| (14) 1-[(4-Methoxyphenyl)sulfonyl]-4-(1-piperazinyl)-1H-indole hydrochloride | 4-methoxyphenylsulfonyl | piperazinyl |
| (15) 1-[(2,4-Difluorophenyl)sulfonyl]-4-(1-piperazinyl)-1H-indole hydrochloride | 2,4-difluorophenylsulfonyl | piperazinyl |
| (16) 1-([1,1'-Biphenyl]-4-ylsulfonyl)-4-(1-piperazinyl)-1H-indole hydrochloride | 4-biphenylsulfonyl | piperazinyl |
| (17) 1-[(3,4-Dimethoxyphenyl)sulfonyl]-4-(1-piperazinyl)-1H-indole hydrochloride | 3,4-dimethoxyphenylsulfonyl | piperazinyl |
| (18) 5-Methyl-2-methoxyl-{[4-(1-piperazinyl)-1H-indol-1-yl]sulfonyl}phenyl ether hydrochloride | 2-methoxy-5-methylphenylsulfonyl | piperazinyl |

TABLE I-continued

Compounds prepared according to synthetic schemes 1 or 2.
All compounds in Table I are hydrochlorides salts.

| EXAMPLE | —SO$_2$—Ar | R$^4$ |
|---|---|---|
| (19) 1-[(2,5-Dichlorophenyl)sulfonyl]-4-(1-piperazinyl)-1H-indole hydrochloride | 2,5-dichlorophenylsulfonyl | piperazinyl |
| (20) 1-[(5-Chloro-1,3-dimethyl-1H-pyrazol-4-yl)sulfonyl]-4-(1-piperazinyl)-1H-indole hydrochloride | 5-chloro-1,3-dimethyl-1H-pyrazol-4-ylsulfonyl | piperazinyl |
| (21) 1-[(3-Chloro-2-methylphenyl)sulfonyl]-4-(1-piperazinyl)-1H-indole hydrochloride | 3-chloro-2-methylphenylsulfonyl | piperazinyl |
| (22) 2-Chloro-5-(4-{[4-(1-piperazinyl)-1H-indol-1-yl]sulfonyl}phenoxy)benzonitrile hydrochloride | 4-(2-chloro-6-cyanophenoxy)phenylsulfonyl | piperazinyl |
| (23) 4-Bromo-2-{[4-(1-piperazinyl)-1H-indol-1-yl]sulfonyl}phenyl methyl ether hydrochloride | 5-bromo-2-methoxyphenylsulfonyl | piperazinyl |
| (24) 4-(1-Piperazinyl)-1-(3-pyridinylsulfonyl)-1H-indole hydrochloride | 3-pyridinylsulfonyl | piperazinyl |

TABLE I-continued

Compounds prepared according to synthetic schemes 1 or 2.
All compounds in Table I are hydrochlorides salts.

| EXAMPLE | —SO₂—Ar | R⁴ |
|---|---|---|
| (25) 7-{[4-(1-Piperazinyl)-1H-indol-1-yl]sulfonyl}-2-(trifluoroacetyl)-1,2,3,4-tetrahydroisoquinoline hydrochloride | | piperazinyl |
| (26) Methyl 2-{[4-(1-piperazinyl)-1H-indol-1-yl]sulfonyl}phenyl sulfone hydrochloride | | piperazinyl |
| (27) 1-[(4-fluorophenyl)sulfonyl]-4-(1-piperazinyl)-1H-indole | | piperazinyl |
| (28) 1-[(5-chloro-3-methyl-1-benzothien-2-yl)sulfonyl]-4-(1-piperazinyl)-1H-indole hydrochloride | | piperazinyl |
| (29) 1-[(4-methylphenyl)sulfonyl]-4-(4-methyl-1-piperazinyl)-1H-indole | | 4-methylpiperazinyl |

TABLE I-continued

Compounds prepared according to synthetic schemes 1 or 2.
All compounds in Table I are hydrochlorides salts.

| EXAMPLE | —SO₂—Ar | R⁴ |
|---|---|---|
| (32) 4-piperazine-N-(4-trifluoromethyl)phenylsulfonyl)indole hydrochloride | 4-(trifluoromethyl)phenylsulfonyl | piperazinyl |
| (33) 4-(3-methyl-1-piperazinyl)-1-{[4-(trifluoromethyl)phenyl]sulfonyl}-1H-indole | 4-(trifluoromethyl)phenylsulfonyl | 3-methylpiperazinyl |
| (36) 1-[(2-methylphenyl)sulfonyl]-4-(4-methyl-1-piperazinyl)-1H-indole | (2-methylphenyl)sulfonyl | 4-methylpiperazinyl |
| (37) 4-(4-ethyl-1-piperazinyl)-1-[(2-methylphenyl)sulfonyl]-1H-indole | (2-methylphenyl)sulfonyl | 4-ethylpiperazinyl |
| (38) 1-[(2-methylphenyl)sulfonyl]-4-(1-piperazinyl)-1H-indole | (2-methylphenyl)sulfonyl | piperazinyl |
| (39) 4-(5-aza-indolizidinyl)-1-(2-methylbenzenesulfonyl)-1H-indole | (2-methylphenyl)sulfonyl | 5-aza-indolizidinyl |

TABLE I-continued

*Compounds prepared according to synthetic schemes 1 or 2.*
*All compounds in Table I are hydrochlorides salts.*

| EXAMPLE | —SO₂—Ar | R⁴ |
|---|---|---|
| (40) 4-(4-methyl-1,4-diazepan-1-yl)-1-[(2-methylphenyl)sulfonyl]-1H-indole | | |
| (41) 4-(3-Methyl-1-piperazinyl)-1-(2-methylbenzenesulfonyl)-1H-indole | | |
| (42) 4-(3,5-dimethyl-1-piperazinyl)-1-[(2-methylphenyl)sulfonyl]-1H-indole | | |
| (43) 4-(4-isopropyl-1-piperazinyl)-1-(2-methylbenzenesulfonyl)-1H-indole | | |
| (44) 4-((1S,4S)-2-methyl-2,5-diazabicyclo[2.2.1]heptyl)-1-(2-methylbenzenesulfonyl)-1H-indole | | |
| (45) 4-(4-methyl-1-homopiperazinyl)-1-(benzenesulfonyl)-1H-indole | | |
| (46) 4-(cis 3,5-dimethyl-1-piperazinyl)-1-(benzenesulfonyl)-1H-indole | | |

TABLE I-continued

Compounds prepared according to synthetic schemes 1 or 2.
All compounds in Table I are hydrochlorides salts.

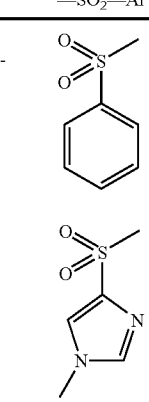

| EXAMPLE | —SO$_2$—Ar | R$^4$ |
|---|---|---|
| (47) 4-(4-ethyl-1-piperazinyl)-1-(benzenesulfonyl)-1H-indole | 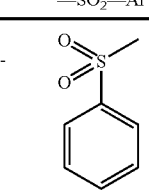 | 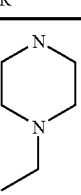 |
| (62) 1-[(N-methyl-1H-imidazol-4-yl)sulfonyl]-4-(1-piperazinyl)-1H-indole hydrochloride | 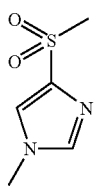 | 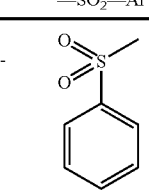 |
| (48) 4-Piperazinyl-1-(4-nitro-benzenesulfonyl)-1H-indole | 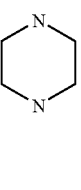 | 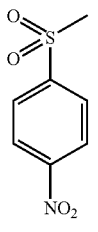 |
| (49) 4-Piperazinyl-1-(4-nitro-benzenesulfonyl)-1H-indole | 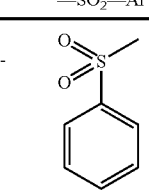 | 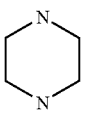 |
| (50) 4-Piperazinyl-1-(4-chloro-benzenesulfonyl)-1H-indole | 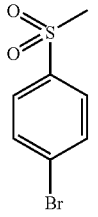 | 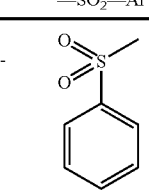 |
| (51) 4-Piperazinyl-1-(E2-phenyl-ethensulfonyl)-1H-indole | 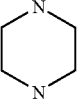 | 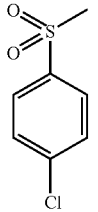 |

TABLE I-continued

Compounds prepared according to synthetic schemes 1 or 2.
All compounds in Table I are hydrochlorides salts.

| EXAMPLE | —SO₂—Ar | R⁴ |
|---|---|---|
| (52) 4-Piperazinyl-1-(3-trifluoromethyl-benzenesulfonyl)-1H-indole | 3-(trifluoromethyl)phenylsulfonyl | piperazinyl |
| (53) 4-Piperazinyl-1-(4-cyanobenzenesulfonyl)-1H-indole | 4-cyanophenylsulfonyl | piperazinyl |
| (54) 4-Piperazinyl-1-(4-chloro-7-sulfonyl-2,1,3-benzoxadiazole sulfonyl)-1H-indole | 4-chloro-2,1,3-benzoxadiazol-7-ylsulfonyl | piperazinyl |
| (55) 4-Piperazinyl-1-(3-cyanobenzenesulfonyl)-1H-indole | 3-cyanophenylsulfonyl | piperazinyl |
| (56) 4-Piperazinyl-1-(4-phenoxybenzenesulfonyl)-1H-indole | 4-phenoxyphenylsulfonyl | piperazinyl |
| (57) 4-Piperazinyl-1-(4-chlorophenylmethanesulfonyl)-1H-indole | (4-chlorophenyl)methanesulfonyl | piperazinyl |

TABLE I-continued

Compounds prepared according to synthetic schemes 1 or 2.
All compounds in Table I are hydrochlorides salts.

| EXAMPLE | —SO$_2$—Ar | R$^4$ |
|---|---|---|
| (58) 4-Piperazinyl-1-(4-methylphenylmethanesulfonyl)-1H-indole | (4-methylbenzyl methanesulfonyl group) | piperazinyl |
| (59) 4-Piperazinyl-1-(1,1-diphenylethanesulfonyl)-1H-indole, | (1,1-diphenylethanesulfonyl group) | piperazinyl |
| (60) 4-Piperazinyl-1-(4-trifluoromethoxybenzenesulfonyl)-1H-indole | (4-trifluoromethoxyphenylsulfonyl group) | piperazinyl |
| (61) 4-Piperazinyl-1-(5-[(benzoylamino)methyl]thiophene-2-sulfonyl)-1H-indole | (5-[(benzoylamino)methyl]thiophene-2-sulfonyl group) | piperazinyl |

General Synthetic Schemes

Scheme 1: (i) NaH, THF, TBDMSCl or TIPSCl in CH$_2$Cl$_2$; (ii) X = Br: t-Bu$_3$P, Pd(OAc)$_2$, Diamine of choice, NaOt-Bu, xylene; (iii) Bu$_4$NF1M, THF or NaF, Ethyl Acetate; (iv) Ar—SO$_2$Cl, Py or NaOH or NaH CH$_2$Cl$_2$; (v) HCl in ether.

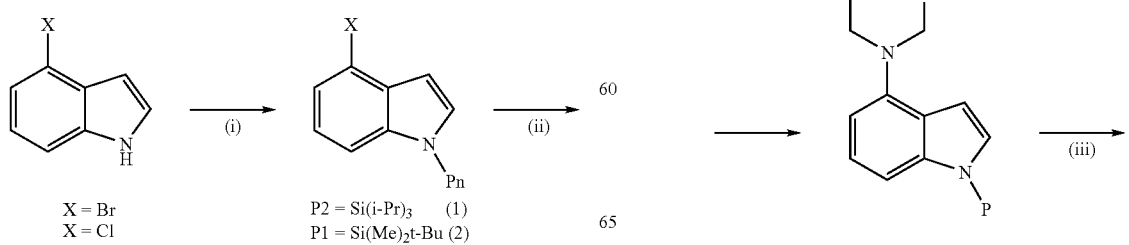

P2 = Si(i-Pr)$_3$ (1)
P1 = Si(Me)$_2$t-Bu (2)

X = Br
X = Cl

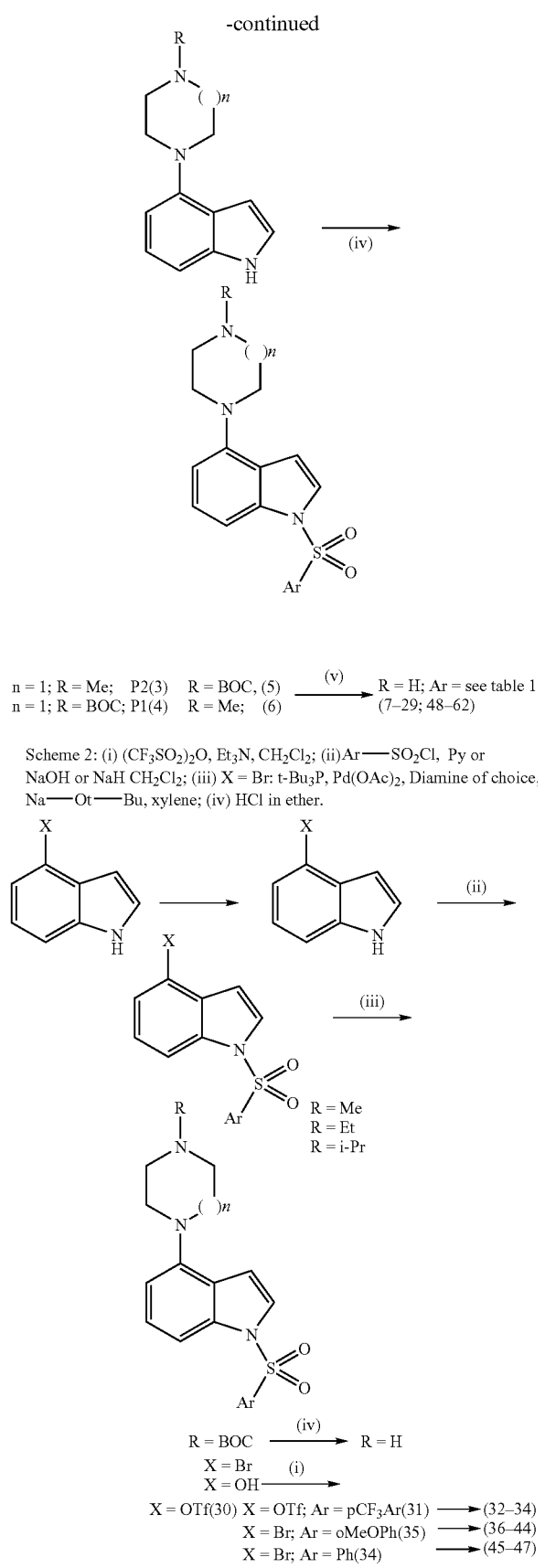

The products described in the following examples were confirmed by standard spectroscopical methods and elemental analysis and/or high resolution MS. NMR spectra were obtained on Bruker 500 MHz or JEOL 270 MHz spectrometers at 25° C., and the chemical shift values are reported as parts per million (δ). MS spectra were acquired on a 2690 Separation Module (Waters) with a Platform LCZ (Micromass). Flash chromatography was performed on Silica gel 60 (Merck) or LiChroprep RP-18 (Merck). HPLC analyses were accomplished on a HP Series1100, with a GROM-SIL 100 ODS-0 AB column, 4.6×50 mm. The HPLC purifications were performed on preparative HPLC/ Mass system using YMC Combi prep ODS-AQ column, 56×20 mm, Gilson pumps, Dynamax UV-1 detector and Finnigan Mass detector. The eluents used were $H_2O$ and $CH_3CN$, both with 0.1% TFA. The purity of the compounds was determined by HPLC. Elemental analysis was performed at Structural Chemistry Department, Biovitrum AB, Stockholm. Melting points, when given, were obtained on a Bütchi or a Gallenkamp melting point apparatus and are uncorrected.

General Synthetic Methods

Method 1: Buchwald Coupling between Aryltriflates or Arylahalides and Amines

To a solution of the aryltriflate (1 equiv.) in xylene are added, under $N_2$ flush, $Pd(OAc)_2$ (0.6 equiv.), (R)-2,2'-bis (diphenylphosphino)-1,1'-binaphthyl (BINAP) (0.1 equiv.) and $Cs_2CO_3$ (3 equiv.), followed by amine (2 equiv.). The mixtures are heated to 100° C.–120° C. under stirring (TLC monitoring). Purification by flash chromatography [$SiO_2$, $CHCl_3$ to MeOH:$CHCl_3$:aq $NH_3$ (10:90: 0.4%)] afforded the final compounds. The final compounds are converted into their hydrochloride salts by dissolving the free bases in methanol and diethyl ether (1:9) followed by the addition of HCl in diethyl ether.

Method 2: Buchwald Coupling between Arylhalides and Amines

To a mixture of 4-bromoindoles (1 equiv), $t$-$Bu_3P$ (0.05 equiv.) or 2-(dicyclohexylphosphino)biphenyl (0.05 equiv.), and Pd $(OAc)_2$ (0.02 equiv.) in xylene are added amines (2.8 equiv.) and NaOt-Bu (2.8 equiv.). The reactions are heated at 120° C. for 4 h, filtered through celite and the solvent is removed. The crude mixtures are purified by column chromatography ($SiO_2$, $CH_2Cl_2$/heptane 1:4) to yield final compounds. The final compounds are converted in their hydrochloride salts according to the same procedure as described in Method 1.

Method 3: Sulfonylation in the Presence of NaOH

Arylsulfonyl chlorides (0.75 rumol) are added to a cold (0° C.) solution of indole derivates (0.5 mmol), grounded NaOH (3 mnmol) and tetrabutyl ammonium hydrogen sulfate (0.05 mmol) in $CH_2Cl_2$ (3 mL). The mixtures are shaken for 30 min at 0° C. and 30 min at room temperature. Each mixture is then filtered through a bed of hydromatrix (Varian; 3 cm) and silica gel (0.5 cm). The system is washed with $CH_2Cl_2$ (2×3 mL) and the solvent is evaporated in vacuum. The resulting residues (final products as free base) are dissolved in $CH_2Cl_2$ (3 mL) and HCl in ether is added (2 mL) and shaken for 2 h at room temperature. The resulting precipitates are collected by filtration to give the final compounds as hydrochloride salts. The purity of the compounds is analyzed by LC and eventually purified by LC/MS if required.

Method 4: Sulfonylation in the Presence of NaH

Sulfonylchlorides (1.5 equiv.) are added to indoles derivatives (1equiv.) and NaH 60% dispersion in oil (2 equiv.) in CH$_2$Cl$_2$ containing DMF (1%). After 1 h at room temperature the reactions are quenched with water, filtered and the solvent is removed. Purification by column chromatography (SiO$_2$, CH$_2$Cl$_2$:MeOH 9:1:0.4% NH$_3$) gave the final compounds. The final compounds are transformed into their hydrochloride salts by the procedure described in Method 1.

Method 5: Sulfonylation of sodium salt of 4-(4-t-butyloxycarbonyl)-piperazinyl-indole (stock solution A).

NaH (163 mg, 6.5 mmol) is added to a solution of 4-(4-t-butyloxycarbonyl)-piperazinyl-indole (1.50 g, 6.50 mmol) in THF (45 mL). The reaction is stirred at room temperature for 0.5 h. The suspension is diluted to 60 mL with THF and distributed into 30 reaction vials (stock solution A). Diverse sulfonylchlorides (0.25 mmol) in THF (2 mL) are added to the stock solution A (2 mL). The reactions are shaken for 3 h followed by addition of MeOH (100 μL). Polystyrene-trisamine (PS-trisamine) is added to the mixtures and the reactions are agitated at room temperature over night. The mixtures are filtered through a short silica column and the volatiles are removed. The crude products are dissolved in MeOH (2 mL) followed by addition of HCl/ether 2 M (4 mL). After 0.5 h the sample was centrifugated and the supernatant was decanted after 0.5 hrs. The remaining solid was washed with (ether) and dried in vacuo to afford the hydrochloride salts.

EXAMPLE 1 (INTERMEDIATE)

4-Bromo-1-(tri-isopropylsilyl)-1H-indole (Scheme 1)

The NaH 60% dispersion in oil (0.94 g, 23.4 mmol) was added to a solution of 4-bromoindole (3.07 g, 15.6 mmol) and triisopropylsilyl chloride (3.62 g, 18.8 mmol) in CH$_2$Cl$_2$ (50 mL) and DMF (2 mL). The reaction was stirred at room temperature for 1 h and quenched with water. The insoluble material was filtered off and the solvent was removed. Purification by column chromatography (SiO$_2$, CH$_2$Cl$_2$/heptane 1:4) yielded 3.44 g (63%) of the title compound: $^1$H NMR (CDCl$_3$) δ 7.42–6.63 (m, 5 H), 1.66 (sept, J=8 Hz, 3 H), 1.10 (d, J=8 Hz, 18H; MS (ESI) 354.4 (M+H)$^+$; Purity (HPLC) >95%.

EXAMPLE 2 (INTERMEDIATE)

N-tert-Butyl-trimethylsilyl-4-chloroindole (Scheme 1)

4-Chloroindole (131.1 g, 0.871 mol) was dissolved in dry THF (0.5 L). The solution was chilled to 0° C. (ice bath, stirring). t-BuOK (97.6 g, 0.871 mol) was added in one portion and the stirring was continued for additional 5 minutes. Tert-butyldimethylchlorosilane (131.3 g, 0.871 mol) was added portionwise over 10 min with a good stirring. The reaction is exothermic. After 30 minutes the reaction was quenched with water (20 ml) and pH was adjusted to 8–9 and extracted with ethyl acetate (3×50 mL). The organic phases were dried (MgSO$_4$), filtered and the volatiles were eliminate by vacuum. The residue was triturated and crystallized from heptane to yield 181 g (78%) of the title compound. $^1$H NMR (CDCl$_3$) δ 7.45 (dd, J=7.9 Hz, J=0.8 Hz, 1 H), 7.25 (d, J=3.0 Hz, 1 H), 7.18–7.07 (m, 2 H), 6.77 (d, 1 H), 0.96 (s, 9 H), 0.62 (s, 6 H); $^{13}$C NMR (CDCl$_3$) 141.8; 131.7; 130.3; 125.9; 122.0; 119.7; 112.5; 103.5; 26.3; 19.5; −3.9; MS (ESI) 266.1 (M+H).

EXAMPLE 3 (INTERMEDIATE)

4-(4-Methyl-1-Piperazinyl)-1-(triisopropylsilyt)-1H-indole (Scheme 1)

The compound was prepared according to Method 2 from 4-bromo-1-(triisopropylsilyl)indole (0.090 g, 0.255 mmol), t-Bu$_3$P (3.6 mg, 0.014 mmol), and Pd (OAc)$_2$ (1 mg, 0.0036 mmol) in xylene (3 mL) and 4-methyl-1-piperazine (0.135 g, 0.73 mmol) and NaOt-Bu (69 mg, 0.72 mmol). The crude was purified by column chromatography (SiO$_2$, CH$_2$Cl$_2$/heptane 1:4) to yield 90 mg (84%) of pure material: $^1$H NMR (CD$_3$OD) δ 7.19–6.56 (m, 5 H), 3.31–3.25 (m, 4 H), 2.71–2.63 (m, 4 H), 2.36 (s, 3 H), 1.76 (sept, J=8 Hz, 3 H), 1.1 (d, J=8 Hz, 18 H); MS (ESI) 372.5 (M+H)$^+$; Purity (HPLC) >95%.

EXAMPLE 4 (INTERMEDIATE)

N-tert-Butyldimethylsilyl-4-(4-Boc-piperazinyl)-indole (Scheme 1)

The compound was prepared according to Method 2 from N-tert-butyldimethylsilyl -4-chloroindole (100 g, 376 mmol, 1 equiv.), tert-butyl 1-piperazinecarboxylate (84 g, 451 mmol), Palladium(II) acetate (1.26 g., 5.62 mmol, 2%), 2-(dicyclohexylphosphino)-biphenyl (3.95 g., 11.28 mmol, 4 mol %), tert-BuONa (50 g, 520 mmol, 1.4 equiv.) in toluene. The solution was cooled to room temperature and KH$_2$PO$_4$ (150 mL, 13% aqueous solution) was added and pH was adjusted (pH=8–9) followed by extraction with toluene (2×100 mL), dried (MgSO$_4$) and evaporated. The residue was crystallized from heptane to yield 124.4 g (79.6%). $^1$H NMR (CDCl$_3$) δ 7.20 (d, J=8.4 Hz, 1 H), 7.13 (d, J=3.2 Hz, 1 H), 7.06 (t, 1 H), 6.60–6.57 (m, 2 H), 3.65 (t, 4 H), 3.16 (t, 4 H), 1.48 (s, 9 H), 0.91 (s, 9 H), 0.58 (s, 6 H); $^{13}$C NMR (CDCl$_3$) δ 155.0; 145.5; 142.2; 129.9; 124.9; 122.0; 109.3; 107.2; 102.9; 79.8; 77.3; 51.5; 28.5; 26.4; 19.5; −3.8; MS (ESI) 416.4 (M+H).

EXAMPLE 5 (INTERMEDIATE)

4-(4-Boc-piperazinyl)-indole (Scheme 1)

A mixture of N-tert-butyldimethylsilyl-4-(4-tert-butyloxylcarbonate-piperazinyl)-indole (4) (116.9 g., 281 mmol), NaF (30 g., 714 mmol), AcOEt (440 g), water (200 mL) and Bu4NSO$_4$ (2 g, 6 mmol) was heated under powerful stirring at 50–60° C. under N$_2$ for 2 h. The organic phase was separated and the water phase was extracted once more by AcOEt (100 mL). The organic phases were dried (MgSO$_4$), evaporated and co-evaporated with ethanol. The residue was crystallized from ether:hexane (1:3) to yield 81.0 g (95.6%) of the title compound. $^1$H NMR (CDCl$_3$) δ 8.59 (bs, 1 H); 7.12–7.02 (m, 3 H), 6.58 (d, J=6.9 Hz, 1 H), 7.53 (t, 1 H), 3.69 (t, 4 H), 3.19 (t, 4 H), 1.53 (s, 9 H); $^{13}$C NMR (CDCl$_3$) δ 155.1; 145.5; 137.1; 123.2; 122.6; 121.4; 106.9; 106.5; 100.8; 80.0; 77.4; 51.4; 28.6; MS (ESI) 302.2 (M+H).

EXAMPLE 6 (INTERMEDIATE)

4-(4-Methyl-1-piperazinyl)-1H-indole (Scheme 1)

A mixture of 4-(1-methyl-1-piperazinyl)-1-(triisopropylsilyl)-1H-indole (110 mg, 0.296 mmol) and Bu4NF IM in THF (1 mL) was stirred at room temperature for 1 h. A mixture of CH$_2$Cl$_2$/heptane 1:1 (10 mL) was added followed by filtration through silica. The product was purified by column chromatography (SiO$_2$, CH$_2$Cl$_2$:MeOH 9:1:0.4% NH$_3$) to yield 60 mg (94%) of the title product: $^1$H NMR (CD$_3$OD) δ 7.11–6.41 (m, 5 H), 3.30–3.23 (m, 4 H), 2.71–2.66 (m, 4 H), 2.37 (s, 3 H); MS (ESI) 216.4 (M+H)$^+$; Purity (HPLC) >95%.

EXAMPLE 7

1-Phenylsulfonyl-4-piperazinylindole Dihydrochloride

The title compound was prepared from 4-boc-piperazinyl-indole and phenylsulfonylchloride according to Method 3: $^1$H NMR (DMSO-d$_6$) δ 9.64 (brs, 2 H), 7.98–7.94 (m, 4 H), 7.80–7.77 (m, 1 H), 7.70–7.65 (m, 1 H), 7.63–7.55 (m, 3 H), 7.27–7.22 (m, 1 H), 6.95 (d, J=3.76 Hz, 1 H), 6.81–6.77 (m, 1 H), 3.31–3.20 (m, 4 H); $^{13}$C NMR (DMSO-d$_6$) δ 144.79, 137.02, 135.22, 134.62, 129.82, 126.65, 125.63, 125.54, 123.49, 111.15, 107.87, 107.76, 47.81, 42.86. Anal. (C$_{18}$H$_{19}$N$_3$O$_2$S.2HCl0.5 H$_2$O) C, H, N.

EXAMPLE 8

1-[(2,5-Dimethoxyphenyl)sulfonyl]-4-(1-piperazinyl)-1H-indole Hydrochloride (Scheme 1)

The title compound was prepared from 4-(4-boc-piperazinyl)-indole and 2,5-dimethoxyphenyl)sulfonyl chloride according to Method 3: $^1$H NMR (500 MHz, DMSO-d$_6$) δ 8.95 (br, 1 H), 7.71 (d, J=5 Hz, 1 H), 7.52 (d, J=5 Hz, 1 H), 7.38 (d, J=8 Hz, 1 H), 7.27 (d, J=8 Hz, 1 H), 7.14 (t, J=8 Hz, 1 H), 7.13 (d, J=8 Hz, 1 H), 6.86 (d, J=5 Hz, 1 H), 6.77 (d, J=8 Hz, 1 H), 3.81 (s, 3 H), 3.64 (s, 3 H), 3.40–3.20 (m, 8 H); MS (ESI+) for m/z 402 (M+H)$^+$.

EXAMPLE 9

1-(Mesitylsulfonyl)-4-(1-piperazinyl)-1H-indole Hydrochloride (Scheme 1)

The title compound was prepared from 4-(4-boc-piperazinyl)-indole and mesitylsulfonylchloride according to Method 3: 1H NMR (270 MHz, DMSO-d$_6$) δ 9.10 (br, 1 H), 7.71 (d, J=5 Hz, 1 H), 7.40–7.20 (m, 3 H), 7.00–6.80 (m, 2 H), 6.51 (d, J=8 Hz, 1 H), 3.30–3.20 (m, 8 H), 2.41 (s, 6 H), 2.27 (s, 3 H); MS (ESI+) for m/z 384 (M+H)$^+$.

EXAMPLE 10

1-(1-Naphthylsulfonyl)-4-(1-piperazinyl)-1H-indole Hydrochloride (Scheme 1)

The title compound was prepared according 4-(4-boc-piperazinyl)-indole and naphthylsulfonylchloride according to Method 3: $^1$H NMR (270 MHz, DMSO-d$_6$) δ 9.03 (br, 1 H), 8.63 (d, J=8 Hz, 1 H), 8.43 (d, J=8 Hz, 1 H), 8.34 (d, J=8 Hz, 1 H), 8.15–8.05 (m, 2 H), 7.80–7.65 (m, 3 H), 7.41 (d, J=8 Hz, 1 H), 7.18 (t, J=8 Hz, 1 H), 6.93 (d, J=5Hz, 1 H), 6.74 (d, J=8Hz, 1 H), 3.30–3.20 (m, 8 H); MS (ESI+) for m/z 392 (M+H)$^+$.

EXAMPLE 11

N,N-Dimethyl-5-{[4-(1-piperazinyl)-1H-indol-1-yl]sulfonyl}-1-naphthalenamine hydrochloride (Scheme 1)

The title compound was prepared from 4-(4-boc-piperazinyl)-indole and 5-N,N-dimethyl-naphthalenamine-1-sulfonylchloride according to Method 3: $^1$H NMR (270 MHz, DMSO-d$_6$) δ 9.25 (br, 1 H), 8.63 (d, J=8 Hz, 1 H), 8.41 (d, J=8 Hz, 1 H), 8.29 (d, J=8 Hz, 1 H), 8.12 (m, 2 H), 7.80–7.65 (m, 3 H), 7.41 (d, J=8 Hz, 1 H), 7.18 (t, J=8 Hz, 1 H), 6.93 (d, J=5 Hz, 1 H), 6.74 (d, J=8 Hz, 1 H), 3.30–3.20 (m, 8 H), 2.82 (m, 6 H); MS (ESI+) for m/z 435 (M+H)$^+$.

EXAMPLE 12

1-[(4-Propoxyphenyl)sulfonyl]-4-(1-piperazinyl)-1H-indole Hydrochloride (Scheme 1)

The title compound was prepared according from 4-(4-boc-piperazinyl)-indole and 4-propoxyphenylsylfonyl chloride according to Method 3: $^1$H NMR (270 MHz, DMSO-d$_6$) δ 9.03 (br, 1 H), 7.89 (d, J=8 Hz, 2 H), 7.78 (d, J=5 Hz, 1 H), 7.61 (d, J=8 Hz, 1 H), 7.25 (t, J=8 Hz, 1 H), 7.07 (d, J=8 Hz, 2 H), 6.93 (d, J=5 Hz, 1 H), 6.67 (d, J=8 Hz, 1 H), 4.01 (t, J=7 Hz, 2 H), 3.28 (m, 8 H), 1.66 (m, 2 H), 1.38 (m, 2 H), 0,88 (t, J=7 Hz, 2 H). MS (ESI+) for m/z 414 (M+H)$^+$.

EXAMPLE 13

1-[(2,5-Dichloro-3-thienyl)sulfonyl]-4-(1-piperazinyl)-1H-indole Hydrochloride (Scheme 1)

The title compound was prepared from 4-(4-boc-piperazinyl)-indole and 2,5-dichloro-3-thienylsulfonyl chloride according to Method 3: $^1$H NMR (270 MHz, DMSO-d$_6$) δ 9.24 (br, 1 H), 7.78 (d, J=5 Hz, 1 H), 7.72 (s, 1 H), 7.57 (d, J=8 Hz, 1 H), 7.29 (t, J=8 Hz, 1 H), 7.01 (d, J=5 Hz, 1 H), 6.86 (d, J=8 Hz, 1 H), 3.31 (m, 8 H). MS (ESI+) for m/z 416 (M+H)$^+$.

EXAMPLE 14

1-[(4-Methoxyphenyl)sulfonyl]-4-(1-piperazinyl)-1H-indole Hydrochoride (Scheme 1)

The title compound was prepared from 4-(4-boc-piperazinyl)-indole and 4-methoxyphenylsulfonyl chloride according to Method 3: $^1$H NMR (270 MHz, DMSO-d$_6$) δ 9.07 (br, 1 H), 7.90 (d, J=8 Hz, 2 H), 7.78 (d, J=5 Hz, 1 H), 7.61 (d, J=8 Hz, 1 H), 7.25 (t, J=8 Hz, 1 H), 7.09 (d, J=8 Hz, 2 H), 6.92 (d, J=5 Hz, 1 H), 6.68 (d, J=8 Hz, 1 H), 3.79 (s, 3 H), 3.24 (m, 8 H); MS (ESI+) for m/z 371 (M+H)$^+$.

EXAMPLE 15

1-[(2,4-Difluorophenyl)sulfonyl]-4-(1-piperazinyl)-1H-indole Hydrochloride (Scheme 1)

The title compound was prepared from 4-(4-boc-piperazinyl)-indole and 2,4-di-fluorophenylsulfonylchloride according to Method 3: $^1$H NMR (270 MHz, DMSO-d$_6$) δ 9.41 (br, 1 H), 8.24 (m, 1 H), 7.75 (m, 1 H), 7.58 (m, 1 H), 7.47–7.33 (m, 2 H), 7.23 (t, J=8 Hz, 1 H), 6.99 (d, J=5 Hz, 1 H), 6.70 (d, J -8 Hz, 1 H), 3.25 (m, 8 H). MS (ESI+) for m/z 378 (M+H)$^+$.

EXAMPLE 16

1-([1,1'-Biphenyl]-4-yl-sulfonyl)-4-(1-piperazinyl)-1H-indole hydrochloride (Scheme 1)

The title compound was prepared from 4-(4-boc-piperazinyl)-indole and 1,1'-biphenyl-4-ylsulfonyl chloride according to Method 3: $^1$H NMR (270 MHz, DMSO-d$_6$) δ 9.26 (br, 1H), 8.04 (m, 2 H), 7.88 (m, 3 H), 7.67 (m, 3 H), 7.46 (m, 3 H), 7.27 (t, J=8 Hz, 1 H), 6.96 (d, J=5 Hz, 1 H), 6.80 (d, J=8 Hz, 1 H), 3.25 (m, 8 H); MS (ESI+) for m/z 418 (M+H)$^+$.

EXAMPLE 17

1-[(3,4-Dimethoxyphenyl)sulfonyl]-4-(1-piperazinyl)-1H-indole hydrochloride (Scheme 1)

The title compound was prepared from 4-(4-boc-piperazinyl)-indole and 3,4-dimethoxyphenylsulfonyl chloride according to Method 3: $^1$H NMR (270 MHz, DMSO-d$_6$) δ 9.00 (br, 1 H), 7.82 (d, J=5 Hz, 1 H), 7.66 (d, J=8 Hz, 1 H), 7.57 (m, 1 H), 7.40 (d, J=3 Hz, 1 H), 7.24 (t, J=8 Hz, 1 H), 7.10 (d, J=8 Hz, 1 H), 6.90 (d, J=5 Hz, 1 H), 6.78 (d, J=8 Hz, 1 H), 3.78 (s, 6 H), 3.24 (m, 8 H); MS (ESI+) for m/z 402 (M+H)$^+$.

EXAMPLE 18

5-Methyl-2-methoxyl-{[4-(1-piperazinyl)-1H-indol-1-yl]sulfonyl}phenyl ether hydrochloride (Scheme 1)

The title compound was prepared from 4-(4-boc-piperazinyl)-indole and 5-methyl-2-methoxyphenylsulfonyl chloride according to Method 3: $^1$H NMR (270 MHz, DMSO-d$_6$) δ 9.45 (br, 1 H), 7.92 (d, J=8 Hz, 1 H), 7.70 (d, J=5 Hz, 1 H), 7.30 (d, J=8 Hz, 1 H), 7.13 (t, J=8Hz, 1 H), 7.01–6.92 (m, 2 H), 6.83 (d, J=5Hz, 1 H), 6.73 (d, J=8Hz, 1 H), 3.70 (s, 3 H), 3.26 (m, 8 H), 3.32 (s, 3 H); MS (ESI+) for m/z 386 (M+H)$^+$.

EXAMPLE 19

1-[(2,5-Dichlorophenyl)sulfonyl]-4-(1-piperazinyl)-1H-indole hydrochloride (Scheme 1)

The title compound was prepared according from 4-(4-boc-piperazinyl)-indole and 2,5-dichlorophenylsulfonyl chloride according to Method 3: $^1$H NMR (270 MHz, DMSO-d$_6$) δ 9.09 (br, 1 H), 8.25 (d, J=3 Hz, 1 H), 7.91–7.81 (m, 2 H), 7.72 (d, J=8 Hz, 1 H), 7.36 (d, J 8 Hz, 1 H), 7.23 (t, J=8 Hz, 1 H), 6.98 (d, J 3 Hz, 1 H), 6.82 (d, J=8 Hz, H), 3.26(m,8 H).

EXAMPLE 20

1-[(5-Chloro-1,3-dimethyl-1H-pyrazol-4-yl)sulfonyl]-4-(1-piperazinyl)-1H-indole hydrochloride (Scheme 1)

The title compound was prepared from 4-(4-boc-piperazinyl)-indole and 5-chloro-1,3-dimethyl-1H-pyrazol-4yl-sulfonyl chloride according to Method 3: $^1$H NMR (270 MHz, DMSO-d$_6$) δ 9.17 (br, 1 H), 7.78 (d, J=3 Hz, 1 H), 7.49 (d, J=8 Hz, 1 H), 7.28 (t, J=8 Hz, 1 H), 6.93 (d, J=3 Hz, 1 H), 6.87 (d, J=8 Hz, 1 H), 3.72 (s, 3 H), 3.28 (m, 8 H), 2.34 (s, 3 H); MS (ESI+) for m/z 394 (M+H)$^+$.

EXAMPLE 21

1-[(3-Chloro-2-methylphenyl)sulfonyl]-4-(1-piperazinyl)-1H-indole hydrochloride (Scheme 1)

The compound was prepared from 4-(4-boc-piperazinyl)-indole and 3-chloro-2-methoxyphenylsulfonyl chloride according to Method 3: $^1$H NMR (270 MHz, DMSO-d$_6$) δ 9.21 (br, 1 H), 7.89 (d, J=3 Hz, 1 H), 7.82 (t, J=8 Hz, 1 H), 7.51 (t, J=8 Hz, 1H), 7.19 (d, J=8 Hz, 1 H), 7.10 (t, J=8 Hz, 1 H), 7.01 (d, J=3 Hz, 1 H), 6.81 (d, J=8 Hz, 1 H), 3.29 (m, 8 H), 2.54 (s, 3 H); MS (ESI+) for m/z 390 (M+H)$^+$.

EXAMPLE 22

2-Chloro-5-(4-{[4-(1-piperazinyl)-1H-indol-1-yl]sulfonyl}phenoxy)benzonitrile hydrochloride (Scheme 1)

The title compound was prepared from 4-(4-boc-piperazinyl)-indole and 2-chloro-5-[(4-(piperazinyl)-1H-indol-1-yl]-sulfonyl chloride according to Method 3: $^1$H NMR (270 MHz, DMSO-d$_6$) δ 9.20 (br, 1 H), 8,06 (d, J=8 Hz, 2 H), 7.81 (d, J=3 Hz, 1 H), 7.75–7.55 (m, 3 H), 7.30–7.15 (m, 4 H), 6.97 (d, J=3 Hz, 1 H), 6.82 (d, J=8 Hz, 1 H), 3.27 (m, 8 H); MS (ESI+) for m/z 493 (M)$^+$, 495.

EXAMPLE 23

4-Bromo-2-{[4-(1-piperazinyl)-1H-indol-1-yl]sulfonyl}phenyl methyl ether hydrochloride (Scheme 1)

The title compound was prepared from 4-(4-boc-piperazinyl)-indole and 4-bromo-2-phenylmethylethersulfonyl chloride according to Method 3: $^1$H NMR (270 MHz, DMSO-d$_6$) δ 9.40 (br, 1 H), 8.12 (d, J=3 Hz, 1 H), 7.88 (d, J=8Hz, 1 H), 7.72 (d, J=5 Hz, 1H), 7.37 (d, J=8 Hz, 1 H), 7.25–7.10 (m, 2 H), 6.89 (d, J=3 Hz, 1 H), 6.78 (d, J=8 Hz, 1 H), 3.71 (s, 3 H), 3.29 (m, 8 H); MS (ESI+) for m/z 450 (M)$^+$, 452.

EXAMPLE 24

4-(1-Piperazinyl)-1-(3-pyridinylsulfonyl)-1H-indole hydrochloride (Scheme 1)

The title compound was prepared from 4-(4-boc-piperazinyl)-indole and 3-pyridinylsulfonyl chloride according to Method 3: $^1$H NMR (270 MHz, DMSO-d$_6$) δ 9.37 (br, 1 H), 9.18 (d, J=3 Hz, 1 H), 8.86 (d, J=5 Hz, 1 H), 8.39 (d, J=8 Hz, 1 H), 7.85 (d, J=3 Hz, 1 H), 7.70–7.60 (m, 2 H), 7.27 (t, J=8 Hz, 1 H), 7.00 (d, J=3 Hz, 1 H), 6.82 (d, J=8 Hz, 1 H), 3.24 (m, 8 H); MS (ESI+) for m/z 343 (M+H)$^+$.

EXAMPLE 25

7-{[4-(1-Piperazinyl)-1H-indol-1-yl]sulfonyl}-2-(trifluoroacetyl)-1,2,3,4-tetrahydroisoquinoline hydrochloride (Scheme 1)

The title compound was prepared from 4-(4-boc-piperazinyl)-indole and 2-(trifluoroacetyl)-1,2,3,4-tetrahydroisoquinolinsulfonyl chloride according to Method 3: $^1$H NMR (500 MHz, DMSO-d$_6$) The experiment was done at 1000° C. δ 9.25 (br, 1 H), 7.94 (br, 1 H), 7.75 (d, J=8 Hz, 1 H), 7.71 (d, J=3 Hz, 1 H), 7.63 (d, J=8 Hz, 1 H), 7.41 (d, J=8 Hz, 1 H), 7.26 (t, J=8 Hz, 1 H), 6.90 (d, J=3 Hz, 1 H), 6.81 (d, J=8 Hz, 1 H), 4.80 (s, 2 H), 3.79 (m, 2 H), 3.35–3.25 (m, 8 H), 2.97 (m, 2 H); MS (ESI+) for m/z 493 (M+H)$^+$.

EXAMPLE 26

Methyl 2-{[4-(1-piperazinyl)-1H-indol-1-yl] sulfonyl}phenyl sulfone hydrochloride (Scheme 1)

The title compound was prepared from 4-(4-boc-piperazinyl)-indole and 2-methylsulfonyl-phenylsulfonyl chloride according to Method 3: $^1$H NMR (270 MHz, DMSO-d$_6$) δ 9.22 (br, 1 H), 8.29 (d, J=-8 Hz, 1 H), 7.99 (t, J=8 Hz, 1 H), 7.90–7.80 (m, 2 H), 7.43 (d, J=8 Hz, 1 H), 7.30–7.15 (m, 2 H), 7.04 (d, J=3 Hz, 1 H), 6.85 (d, J=8 Hz, 1 H), 3.56 (s, 3 H), 3.29 (m, 8 H); MS (ESI+) for m/z 420 (M+H)$^+$.

EXAMPLE 27

1-[(4-fluorophenyl)sulfonyl]-4-(1-piperazinyl)-1H-indole hydrochloride (Scheme 1)

The title compound was prepared from 4-(4-boc-piperazinyl)-indole and 2-methylsulfonyl-phenylsulfonyl chloride according to Method 4 yield the hydrochloride (yield 70%), HPLC purity >95%; $^1$H NMR (DMSO-d$_6$) δ 3.26 (bs, 8H), 6.80 (bs, 1H), 6.95 (bs, 1H), 7.26 (bs, 1H), 7.61 (app t, 2H), 7.80 (bs, 1H), 8.06 (bs, 1H), 9.30 (bs, 1H); $^{13}$C NMR(DMSO-d$_6$) δ 165.20, 144.94, 135.14, 133.31, 130.06 (2C), 125.62 (2C), 123.50, 117.25, 117.06, 111.15, 107.92, 107.71, 47.82 (2C), 42.98 (2C); MS rosES-FIA) m/z 360 (M+H).

EXAMPLE 28

1-[(5-chloro-3-methyl-1-benzothien-2-yl)sulfonyl]-4-(1-piperazinyl)-1H-indole hydrochloride (Scheme 1)

The title compound was prepared 4-(4-boc-piperazinyl)-indole and 1-[(5-chloro-3-methyl-1-benzothien-2-yl)sulfonyl chloride according to Method 4 to afford the hydrochloride salt (yield 45%), HPLC purity >95%; $^1$H NMR (DMSO-d$_6$) δ 2.65 (s, 3H), 3.26 (bs, 8H), 6.82 (app d, 1H), 7.00 (appd, 1H), 7.28 (app t, 1H), 7.60 (app dd, 2H), 7.87 (app d, 1H), 8.08–8.12 (m, 2H); $^{13}$C NMR (DMSO-d$_6$) δ 145.05, 139.82, 139.35, 137.46, 135.14, 133.31, 130.96, 128.70 (2C), 125.62, 124.89, 124.12, 123.52, 111.42, 107.91, 107.71, 47.87 (2C), 43.03 (2C), 12.27; MS (posES-FIA) m/z 446 (M+H).

EXAMPLE 29

4-(4-Methyl-1-piperazinyl)-1-(4-methylbenzenesulfonyl)-1H-indole hydrochloride (Scheme 1)

The title compound was prepared 4-(4-methyl-1-piperazinyl)-1H-indole and p-methylbenzenesulfonyl chloride according to Method 4 (45%): $^1$H NMR (CD$_3$OD) δ 7.81–6.77 (m, 9H), 3.62–3.02 (m, 8H), 2.98 (s, 3H), 2.34 (s, 3H); MS (ESI) 370.5 (M+H)$^+$; Purity (HPLC) >95%.

EXAMPLE (INTERMEDIATE) 30

Synthesis of 4-(trifluoromethylsulfonyloxy)indole (Scheme 2)

Et$_3$N (1.6 mL, 11.3 mmol) was added to a solution of 4-hydroxylindole (1.0 g, 7.5 mmol) in CH$_2$Cl$_2$ (20 mL). The reaction was cooled (ice bath) followed by the careful addition of a solution N-phenyl-bis(trifluoromethanesulfonamide) (2.6 g, 7.5 nunol) in CH$_2$Cl$_2$. The reaction was washed with aqueous K$_2$CO$_3$ after 10 minutes, dried (K$_2$CO$_3$) and filtered. The volatiles were eliminated by vacuum to give 2.9 g of a light brown oil that was purified by flash chromatography (SiO$_2$, CHCl$_3$). This gave 2.47 g (62%) of the title product as a light orange oil. Purity according to GC analysis was 92%. $^1$H NMR (MeOH-d3): δ 7.45 (d, 1H), 7.35 (d, 1H), 7.15 (t, 1H), 7.00 (d, 1H), 6.50 (d, 1H).

EXAMPLE (INTERMEDIATE) 31

Synthesis of 4-(trifluoromethylsulfonyloxy)(N-(4-trifluoromethyl)phenylsulfonyl)indole (Scheme 2)

A solution of 4-(trifluoromethylsulfonyloxy)indole (2.28 g, 8.6 mmol) in CH$_2$Cl$_2$ was added dropwise over 10 minutes to a mixture of NaH (619 mg, 25.8 mmol prewashed with heptane) in CH$_2$Cl$_2$ (20 mL) and DMF (0.5 mL) under N$_2$, A solution of 4-(trifluoromethyl)-benzenesulfonyl chloride (2.31 g, 9.5 mmol) in CH$_2$Cl$_2$ (1 mL) was then added slowly at 0° C. The mixture was left at room temperature under stirring for 1 h. The reaction was then quenched carefully with water, the organic phase isolated, dried, filtered through silica and concentrated to yield 3.3 g crude product as a red oil. The product was purified by flash chromatography (SiO$_2$, heptane to heptane/EtOAc 10:1 to yield 2.43 g (59%) of the title product as a colorless oil. HPLC analysis 100%. MS m/z=496 (M+Na+). $^1$H NMR (MeOH-d3): δ 8.20 (d, 2H), 8.1 (d, 1H), 7.85 (m, 3H), 7.45 (t, 1H), 7.30 (d, 1H), 6.85 (d, 1H).

EXAMPLE 32

4-Piperazino-N-(4-trifluoromethyl)phenylsulfonyl) indole hydrochloride (Scheme 2)

The title compound was prepared from 4-(trifluoromethylsulfonyloxy)(N-(4-trifluoromethyl)-phenylsulfonyl)indole (200 mg, 0.42 mmol) and piperazine (72 mg, 0.84 mmol) according to Method 1. Purification by flash chromatography (SiO$_2$, CHCl$_3$ to MeOH:CHCl$_3$ 10:90:0.4% aq NH$_3$) afforded to 10 mg of a yellow oil. This was dissolved in ethanol and HCl/ether was added and allowed to stir for a few hours. The solid was filtered to yield 10 mg final product as a beige solid that was further purified by preparative HPLC to give, after formation of the HCl salt, the final product (38 mg, 51 %) as an off-white solid. HPLC 97%. MS (posEI) m/z=410 (M+H). $^1$H NMR (CD$_3$OD) δ 8.12 (d, 2H,J=8.3 Hz), 7.84 (d, 2H, J=8.3 Hz), 7.76–7.68 (m, 2H), 7.33–7.27 (m, 1H), 6.88–6.85 (m, 2H) 3.44–3.30 (m, 8H, partly hidden).

EXAMPLE 33

4-(3-Methylpiperazine)-(N-(4-trifluoromethyl)phenylsulfonyl)indole Dihydrochloride (Scheme 2)

The title compound was prepared from 4-(trifluoromethylsulfonyloxy)(N-(4-trifluoromethyl)-phenylsulfonyl)indole and rac-2-methylpiperazine according to Method 1. Filtration through silica using $CHCl_3$ to $MeOH:CHCl_3$ 10:90: 0.4% aq $NH_3$ as eluent gave 48 mg of final product as a beige solid. mp 145° C. (dec); $^1$H NMR (MeOH-d3): δ 8.10 (d, 2H), 7.85 (d, 2H), 7.75 (d, 1H), 7.65 (d, 1H), 7.30 (t, 1H), 6.85 (m, 2H), 3.50 (m, 5H), 3.00 (t, 1H), 2.85 (t, 1H), 1.35 (d, 3H);). HPLC 94%; MS (posEI) m/z-424 (M+H). Anal. ($C_{20}H_{20}F_3N_3O_2S.2HCl$) C,H,N,S. N calcd. 8.47. found 9.32.

EXAMPLE (INTERMEDIATE) 34

4-Bromo-1-(benzenesulfonyl)-1H-indole (Scheme 2)

4-Bromo-1-(benzenesulfonyl)-1H-indole was prepared from 4-bromoindole and phenylsulfonyl chloride according to Method 4 to afford 3.1 g (91%) of a light purple solid: $^1$HNMR ($CDCl_3$) δ 7.94 (d, J=8 Hz, 1H), 7.89–7.84 (m, 2H), 7.62 (d, 4 Hz, 1H), 7.57–7.51 (m, 1H), 7.46–7.37 (m, 3H), 7.19–7.13 (m, 1H), 6.72 (dd, J=1, 4 Hz, 1H); MS (ESI) 419.9+421.9 (M+H)$^+$; Purity (HPLC) >95%.

EXAMPLE (INTERMEDIATE) 35

4-Bromo-1-(2-methyl-benzenesulfonyl)-1H-indole (Scheme 2)

The compound was prepared from 4-bromoindole (1.02 g, 5.25 mmol) and o-methylbenzenesulfonyl chloride (a 9:1 mixture of ortho and para methyl isomers) (1.29 g, 6.78 mmol) according to method 4. Purification by column chromatography ($SiO_2$, $CH_2Cl_2$:heptane) gave 1.6 g (87%) of the title compound which contains ca 10% of the p-methyl isomer) as a light purple viscous oil: $^1$H NMR ($CD_3OD$) δ 7.94–6.68 (m, 9H), 2.52 (s, 3H); MS (ESI) 352.3 (M+H)$^+$; Purity (HPLC) >95%.

EXAMPLE 36

4-(4-Methyl-1-piperazinyl)-1-(2-methylbenzenesulfonyl)-1H-indole (Scheme 2)

The title compound was prepared from 4-bromo-1-(2-methyl-benzenesulfonyl)-1H-indole (0.135 mg, 0.385 mmol) and 4-methyl-1-piperazine (0.143 mg, 0.77 mmol) according to Method 2. The product purified by flash column chromatography ($SiO_2$, $CH_2Cl_2$:MeOH 9:1:0.4% $NH_3$) and converted into its HCl salt to afford 15 mg (10%): $^1$HNMR ($CD_3OD$) δ 7.97–6.79 (m, 9H), 3.72–3.07 (m, 8H), 3.01 (s, 31H), 2.48 (s, 3H); MS (ESI) 370.0 (M+H)$^+$; Purity (HPLC) >95%.

EXAMPLE 37

4-(4-Ethyl-1-piperazinyl)-1-(2-methylbenzenesulfonyl)-1H-indole (Scheme 1)

The compounds was prepared from 4-bromo-1-(2-methyl-benzenesulfonyl)-1H-indole and 4-ethyl-1-piperazine according to Method 1. The product was isolated by column chromatography ($SiO_2$, $CH_2Cl_2$:MeOH/heptane:0.4% $NH_3$) and converted into its hydrochloride salt by addition of HCl/ether to give 85 mg (40%) of a white solid: $^1$HNMR ($CD_3OD$) δ 7.95–6.61 (m, 9H), 3.41–3.26 (m, 8H), 3.20–3.07 (m, 2H), 2.47 (s, 3H), 1.42 (t, J=7 Hz, 3H); MS (ESI) 384.0 (M+H)$^+$; Purity (HPLC) >95%.

EXAMPLE 38

4-(1-Piperazinyl)-1-(2-methylbenzenesulfonyl)-1H-indole (Scheme 1)

The title compound was prepared from 4-bromo-1-(2-methyl-benzenesulfonyl)-1H-indole and piperazine according to Method 1 to give 25 mg (12%) of a white solid: $^1$HNMR ($CD_3OD$) δ 7.91–6.79 (m, 9H), 3.49–3.30 (m, 8H), 2.48 (s, 3H); MS (ESI) 356.1 (M+H)$^+$; Purity (HPLC) >95%.

EXAMPLE 39

4-(5-Aza-indolizidinyl)-1-(2-methylbenzenesulfonyl)-1H-indole (Scheme 1)

The title compound was prepared from 4-bromo-1-(2-methyl-benzenesulfonyl)-1H-indole and 5-aza-indolizidinyl according to Method 1 to give 30 mg (13%) of a white solid: $^1$H NMR on free base ($CDCl_3$) δ 7.85–7.66 (m, 9H), 3.63–3.47 (m, 1H), 3.16–2.93 (m, 3H), 2.67–2.45 (m, 5H), 2.51 (s, 3H), 2.33–2.19 (m, 2H), 1.92–1.74 (m, 4H), 1.52–1.44 (m, 1H); MS (ESI) 396.0 (M+H)$^+$; Purity (HPLC) >95%.

EXAMPLE 40

4-(4-Methyl-1-homopiperazinyl)-1-(2-methylbenzenesulfonyl)-1H-indole (scheme 1)

The compounds was prepared from 4-bromo-1-(2-methyl-benzenesulfonyl)-1H-indole and 4-methyl-1-homopiperazine according Method 1 to give 20 mg (13%) of a white solid: $^1$H NMR ($CD_3OD$) δ 7.91–6.73 (m, 9H), 3.74–3.45 (m, 8H), 3.00 (s, 3H), 2.47 (s, 3H), 2.34–2.26 (m, 2H); MS (ESI) 384.0 (M+H)$^+$; Purity (HPLC) >95%.

EXAMPLE 41

4-(3-Methyl-1-piperazinyl)-1-(2-methylbenzenesulfonyl)-1H-indole (Scheme 1)

The compound was prepared from 4-bromo-1-(2-methyl-benzenesulfonyl)-1H-indole and 3-methylpiperazine according to Method 1 to give 110 mg (38%) of a white solid: $^1$HNMR ($CD_3OD$) δ 7.92–6.82 (m, 9H), 3.64–3.39 (m, 5H), 3.12–3.03 (m, 1H), 2.92–2.83 (m, 1H), 2.47 (s, 3H), 1.40 (d, J=7 Hz, 3H); MS (ESI) 370.0 (M+H)$^+$; Purity (HPLC) 94%.

EXAMPLE 42

4-(cis-3,5-Dimethyl-1-piperazinyl)-1-(2-methylbenzenesulfonyl)-1H-indole (Scheme 1)

The compound was prepared according from 4-bromo-1-(2-methyl-benzenesulfonyl)-1H-indole and cis-3,5-dimethyl-1-piperazine according to Method 1 to give 10 mg (4%) of a white solid: $^1$HNMR (CD$_3$OD) δ 7.90–6.82 (m, 9H), 3.69–3.58 (m, 4H), 2.83–2.74 (m, 2H), 2.45 (s, 3H), 1.41 (d, J=7 Hz, 6H); MS (ESI) 492.1 (M+H)$^+$; Purity (HPLC) 95%.

EXAMPLE 43

4-(4-Isopropyl-1-piperazinyl)-1-(2-methylbenzene-sulfonyl)-1H-indole (Scheme 1)

The compound was prepared from 4-bromo-1-(2-methyl-benzenesulfonyl)-1H-indole and 4-isopropyl-1-piperazine according to Method 1 to give 75 mg (56%) of a white solid: $^1$H NMR (CD$_3$OD) δ 7.92–6.81 (m, 9H), 3.75–3.56 (m, 5H), 3.48–3.40 (m, 2H), 3.19–3.09 (m, 1H), 2.47 (s, 31H), 1.44 (d, J=7 Hz, 6H); MS (ESI) 398.1 (M+H)$^+$; Purity (HPLC) >95%.

EXAMPLE 44

4-((1S,4S)-2-Methyl-2,5-diazabicyclo[2.2.1]heptyl)-1-(2-methylbenzenesulfonyl)-1H-indole (Scheme 1)

The compound was prepared from 4-bromo-1-(2-methyl-benzenesulfonyl)-1H-indole and (1S,4S)-2-methyl-2,5-diazabicyclo[2.2.1]heptane according to Method 1 to give 25 mg (19%) of a white solid: $^1$H NMR (CD$_3$OD) δ 7.91–6.44 (m, 9H), 4.67–4.63 (m, 1H), 4.35–4.33 (m, 1H), 4.09–4.07 (m, 1H), 3.99–3.95 (m, 1H), 3.72–3.70 (m, 1H), 3.21–3.17 (m, 1H), 2.95 (s, 3H), 2.33–2.31 (m, 2H); MS (ESI) 382.1 (M+H)$^+$; Purity (HPLC) >95%.

EXAMPLE 45

4-(4-Methyl-1-homopiperazinyl)-1-(benzenesulfonyl)-1H-indole (Scheme 1)

The compound was prepared from 4-bromo-1-(benzene-sulfonyl)-1H-indole and 4-methyl-1-homopiperazine according to Method 1 to give 4 mg (2%) of a white solid: $^1$H NMR for free base (CDCl$_3$) δ 7.86–7.11 (m, 8H), 6.71 (d, J=4 Hz, 1H) 6.54 (d, J=8 Hz, 1H), 3.60–3.57 (m, 2H), 3.52–3.48 (m, 2H), 2.81–2.78 (m, 2H), 2.68–2.64 (m, 2H), 2.39 (s, 3H), 2.04–2.00 (m, 2H); MS (ESI) 370.1 (M+H)$^+$; Purity (HPLC) >95%.

EXAMPLE 46

4-(cis 3,5-Dimethyl-1-piperazinyl)-1-(benzenesulfonyl)-1H-indole (Scheme 1)

The title compound was prepared from 4-bromo-1-(benzenesulfonyl)-1H-indole and cis 3,5-dimethyl-1-piperazine according to Method 1 to give 138 mg (52%) of a white solid: $^1$HNMR (CD$_3$OD) δ 7.93–6.82 (m, 10 H), 3.64–3.59 (m, 4 H), 2.77–2.68 (m, 2 H), 1.36 (d, J=6 Hz, 6 H); MS (ESI) 370.0 (M+H)$^+$; Purity (HPLC) >95%.

EXAMPLE 47

4-(4-Ethyl-1-piperazinyl)-1-(benzenesulfonyl)-1H-indole (Scheme 1)

The title compound was prepared from 4-bromo-1-(benzenesulfonyl)-1H-indole and 4-ethylpiperazine according to Method 1 to afford 129 mg (48%) of a white solid: $^1$H NMR (CD$_3$OD) δ 7.94–6.81 (m, 10 H), 3.69–3.62 (m, 4 H), 2.34–3.26 (partly hidden) (m, 4 H), 3.14–3.04 (m, 2 H), 1.40 (t, J=7 Hz, 3 H); MS (ESI) 370.1 (M+H)$^+$; Purity (HPLC) >95%.

EXAMPLE 48

4-Piperazinyl-1-(4-nitro-benzenesulfonyl)-1H-indole (Scheme 1)

The title compound was prepared according to Method 5 from 4-nitrobenzenesulfonyl chloride and the sodium salt of 4-(4-t-butyloxycarbonyl)-piperazinyl-indole (stock solution A) to give 60.3 mg (86%) as HCl salt: $^1$HNMR (CD$_3$OD) δ 8.34 (d, 2 H, J=9.0 Hz), 8.18 (d, 2 H, J=9.0 Hz), 7.76–7.69 (m, 2 H), 7.33–7.27 (m, 1 H), 6.90–6.85 (m, 2 H) 3.44–3.30 (m, 8 H, partly obscured); MS (ESI) 386.9 (M+H)$^+$; Purity (HPLC) 95%.

EXAMPLE 49

4-Piperazinyl-1-(4-bromo-benzenesulfonyl)-1H-indole (Scheme 1)

The title compound was prepared according to Method 5 from 4-bromobenzenesulfonyl chloride and the sodium salt of 4-(4-t-butyloxycarbonyl)-piperazinylindole (stock solution A) to give 40.3 mg (53%) as HCl salt; $^1$HNMR (CD$_3$OD) δ 7.81–7.61 (m, 6 H), 7.30–7.24 (m, 1 H), 6.86–6.83 (m, 2 H) 3.44–3.30 (m, 8 H); MS (ESI) 419.9, 421.9 (M+H)$^+$; Purity (HPLC) 98%.

EXAMPLE 50

4-Piperazinyl-1-(4-chloro-benzenesulfonyl)-1H-indole (Scheme 1)

The title compound was prepared according to Method 5 from 4-chloro-benzenesulfonyl chloride and the sodium salt of 4-(4-t-butyloxycarbonyl)-piperazinyl-indole (stock solution A) to give 42 mg (61%) as HCl salt: $^1$HNMR (CD$_3$OD) δ 7.88 (d, 2 H, J=8.7 Hz), 7.72–7.63 (m, 2 H), 7.50 (d, 2 H, J=8.7 Hz), 7.30–7.24 (m, 1 H), 6.86–6.84 (m, 2 H) 3.44–3.31 (m, 8 H); MS (ESI) 375.9, 377.9 (M+H)$^+$; Purity (HPLC) 95%.

EXAMPLE 51

4-Piperazinyl-1-(E 2-phenyl-ethensulfonyl)-1H-indole (Scheme 1)

The title compound was prepared according to Method 5 from 1-(E 2-phenyl-ethensulfonyl chloride and the sodium salt of 4-(4-t-butyloxycarbonyl)-piperazinyl-indole (stock solution A) to give 8 mg (11%) as HCl salt: $^1$HNMR (CD$_3$OD) δ 7.78 (d, 1 H, J=15.4 Hz) 7.68–7.25 (m, 9 H), 7.16 (d, 1 H, J=15.4), 6.88–6.84 (m, 2 H) 3.46–3.34 (m, 8 H); MS (ESI) 368.0 (M+H)$^+$; Purity (HPLC) 97%.

EXAMPLE 52

4-Piperazinyl-1-(3-trifluoromethyl-benzenesulfonyl)-1H-indole (Scheme 1)

The title compound was prepared according to Method 5 from 3-trifluoromethyl-benzenesulfonyl chloride and the sodium salt of 4-(4-t-butyloxycarbonyl)-piperazinyl-indole (stock solution A) to give 42 mg (61%) of a white solid:

¹HNMR (CD₃OD) δ 8.21–8.16 (m, 2 H) 7.96–7.93 (m, 1 H), 7.34–7.27 (m, 1 H), 6.89–6.85 (m, 2 H) 3.44–3.32 (m, 8 H); MS (ESI) 410.0 (M+H)⁺; Purity (HPLC) 95%.

EXAMPLE 53

4-Piperazinyl-1-(4-cyanobenzenesulfonyl)-1H-indole (Scheme 1)

The title compound was prepared according to Method 5 from 4-cyanobenzenesulfonyl chloride and the sodium salt of 4-(4-t-butyloxycarbonyl)-piperazinyl-indole (stock solution A) to give 28 mg (42%) of a white solid: MS (ESI) 367.0 (M+H)⁺; Purity (HPLC) 95%.

EXAMPLE 54

4-Piperazinyl-1-(4-chloro-7-chloro-2,1,3-benzoxadiazole sulfonyl)-1H-indole (Scheme 1)

The title compound was prepared according to Method 5 from 4-chloro-7-chlorosulfonyl-2,1,3-benzoxadiazole sulfonylchloride and the sodium salt of 4-(4-t-butyloxycarbonyl)-piperazinyl-indole (stock solution A) to give 12 mg (16%) of a white solid: ¹HNMR (CD₃OD) δ 8.42 (d, 2 H, J=7.1 Hz), 7.84–7.63 (m, 3 H), 7.27–7.21 (m, 1 H), 6.85–6.81 (m, 2 H) 3.43–3.27 (m, 8 H, partly hidden); MS (EST) 418.0 (M+H)⁺; Purity (HPLC) 91%.

EXAMPLE 55

4-Piperazinyl-1-(3-cyanobenzenesulfonyl)-1H-indole (Scheme 1)

The title compound was prepared according to Method 5 from 4-trifluoromethyl-benzenesulfonyl chloride and sodium salt of 4-(4-t-butyloxycarbonyl)-piperazinyl-indole (stock solution A) to give 68 mg (50%) of a white solid: MS (ESI) 367.1 (M+H)⁺; Purity (HPLC) 93%.

EXAMPLE 56

4-Piperazinyl-1-(4-phenoxybenzenesulfonyl)-1H-indole (Scheme 1)

The title compound was prepared according to Method 5 from 4-phenoxybenzenesulfonyl chloride and sodium salt of 4-(4-t-butyloxycarbonyl)-piperazinyl-indole (stock solution A) to give 68 mg (87%) of a white solid: ¹HNMR (CD₃OD) 7.82–7.59 (m, 4 H), 7.76–7.34 (m, 4 H), 6.88–6.78 (m, 6 H) 3.45–3.30 (m, 8 H); MS (ESI) 434.1 (M+H)⁺; Purity (HPLC) 95%.

EXAMPLE 57

4-Piperazinyl-1-(4-chlorophenylmethanesulfonyl)-1H-indole (Scheme 1)

The title compound was prepared according to Method 5 from 4-chlorophenylmethanesulfonyl chloride and sodium salt of 4-(4-t-butyloxycarbonyl)-piperazinyl-indole (stock solution A) to give 3 mg (4%) of a white solid: ¹H NMR (CD₃OD) δ 7.44 (d, 1 H. J=8.2 Hz) 7.24–7.18 (m, 4 H), 6.87–6.84 (m, 3 H), 6.69–6.67 (m, 1 H) 4.72 (s, 2 H) 3.43–3.31 (m, 8 H, partly hidden); MS (ESI) 390.0, 392.1 (M+H)⁺; Purity (HPLC) 91%.

EXAMPLE 58

4-Piperazinyl-1-(4-methylphenylmethanesulfonyl)-1H-indole (Scheme 1)

The title compound was prepared according to Method 5 from 4-methylphenylmethanesulfonyl chloride and sodium salt of 4-(4-t-butyloxycarbonyl)-piperazinyl-indole (stock solution A) to give 9 mg (13%) of a white solid: ¹HNMR (CD₃OD) δ 7.46 (d, 1 H, J=8.4 Hz) 7.24–7.18 (m, 1 H), 7.06 (d, 1 H, J=4.0 Hz) 6.95–6.85 (m, 3 H), 6.76–6.64 (m, 3 H) 4.65 (s, 2 H) 3.47–3.35 (m, 8 H) 2.24 (s, 3 H); MS (ESI) 370.1 (M+H)⁺; Purity (HPLC) 95%.

EXAMPLE 59

4-Piperazinyl-1-(1,1-diphenylethanesulfonyl)-1H-indole (Scheme 1)

The title compound was prepared according to Method 5 from 1,1-diphenylethanesulfonyl chloride and the sodium salt of 4-(4-t-butyloxycarbonyl)-piperazinyl-indole (stock solution A) to give 57 mg (71%) of a white solid: ¹H NMR (CD₃OD) δ 7.59 (d, 1 H, J=8.4 Hz), 7.31–7.25 (m, 1 H), 7.12–7.05 (m, 10 H), 6.86–6.83 (m, 1 H) 6.50–6.48 (m, 1 H) 6.42 (t, 1 H, J=6.6 Hz) 4.28 (d, 2 H, J=6.6 Hz) 3.47–3.32 (m, 8 H); MS (ESI) 446.1 (M+H)⁺; Purity (HPLC) 92%.

EXAMPLE 60

4-Piperazinyl-1-(4-trifluoromethoxybenzenesulfonyl)-1H-indole (Scheme 1)

The title compound was prepared according to Method 5 from 4-trifluoromethoxybenzenesulfonyl chloride and the sodium salt of 4-(4-t-butyloxycarbonyl)-piperazinyl-indole (stock solution A) to give 46 mg (60%) of a white solid: ¹HNMR (CD₃OD) δ 8.07–8.04 (m, 2 H), 7.75–7.72 (m, 1 H) 7.67–7.68 (m, 1 H) 7.43–7.40 (m, 2 H), 7.32–7.20 (m, 1 H) 6.87–6.85 (m, 2 H) 3.44–3.31 (m, 8 H, partly hidden); MS (ESI) 426.1 (M+H)⁺; Purity (HPLC) 93%.

EXAMPLE 61

4-Piperazinyl-1-(5-[(benzoylamino)methyl] thiophene-2-sulfonyl)-1H-indole (Scheme 1)

The title compound was prepared according to Method 5 from 5-[(benzoylamino)methyl]thiophene-2-sulfonylchloride and the sodium salt of 4-(4-t-butyloxycarbonyl)-piperazinyl-indole (stock solution A) to give 5 mg (6%) of a white solid: ¹H NMR (CD₃OD) δ 7.79–7.42 (m, 8 H), 7.30–7.24 (m, 1 H) 7.00–6.98 (m, 1 H) 6.85–6.81 (m, 2 H) 3.39–3.28 (m, 8 H, partly hidden); MS (ESI) 481.1 (M+H)⁺; Purity (HPLC) 91%.

EXAMPLE 62

1-[(N-methyl-1H-imidazol-4-yl)sulfonyl]-4-(1-piperazinyl)-1H-indole hydrochloride The compound was prepared from 4-(4-boc-piperazinyl)-indole 1-methyl-1H-imidazol-4-yl)sulfonyl chloride according to Method 3:Yield: 74%. ¹H NMR (270 MHz, DMSO-d₆) δ 9.23 (br, 1 H), 8.25 (s, 1 H), 7.75 (s, 1 H), 7.61 (d, J=3 Hz, 1 H), 7.53 (d, J=8 Hz, 1 H), 7.22 (t, J=8 Hz, 1 H), 6.86

(d, J=3 Hz, 1 H), 6.79 (d, J=8 Hz, 1 H), 3.65 (s, 3 H), 3.27 (m, 8 H); MS (ESI+) for m/z 346 (M+H)⁺.

Scheme 3 (i) (iPr)₃Si, NaH, dimethylformamide/dichlorometane; R⁵(when it is different than H)(tBu)₃P, Pd(OAc)₂, NaOtBu; (iii) Bu₄NF in THF, acetonitrile; (iv) R¹(ArSO₂— as indicated in Table II), NaOH, dichlorometane.

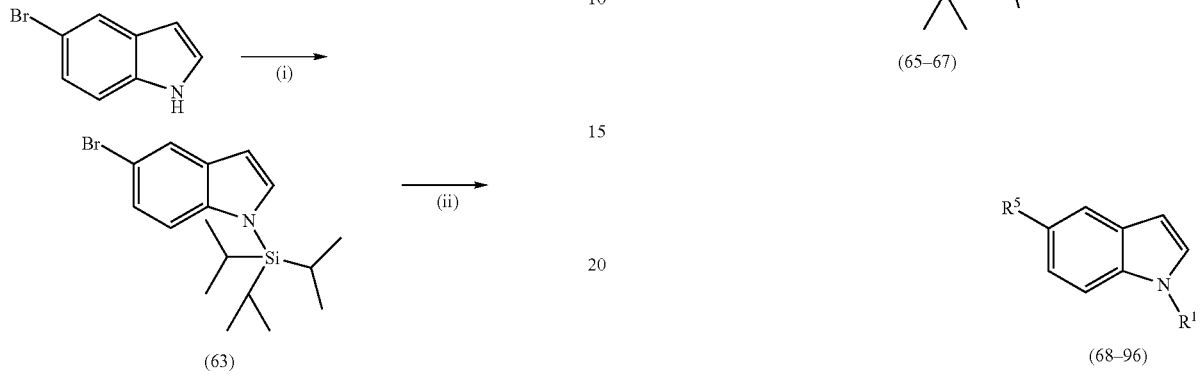

TABLE II

Compounds prepared according to synthetic scheme 3.

| EXAMPLE | —SO₂—Ar | R⁵ |
|---|---|---|
| (68) 5-(4-methyl-1-piperazinyl)-1-(phenylsulfonyl)-1H-indole | phenylsulfonyl | 4-methyl-1-piperazinyl |
| (69) 1-[(4-methylphenyl)sulfonyl]-5-(4-methyl-1-piperazinyl)-1H-indole | (4-methylphenyl)sulfonyl | 4-methyl-1-piperazinyl |
| (70) 5-(4-isopropyl-1-piperazinyl)-1-(phenylsulfonyl)-1H-indole | phenylsulfonyl | 4-isopropyl-1-piperazinyl |

TABLE II-continued

Compounds prepared according to synthetic scheme 3.

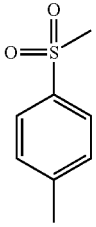

| EXAMPLE | —SO$_2$—Ar | R$^5$ |
|---|---|---|
| (71) 5-(4-isopropyl-1-piperazinyl)-1-[(4-methylphenyl)sulfonyl]-1H-indole | 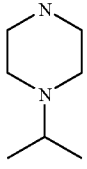 | 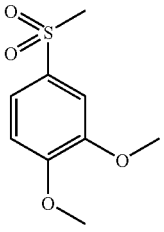 |
| (72) 1-[(3,4-dimethoxyphenyl)sulfonyl]-5-(4-propyl-1-piperazinyl)-1H-indole | 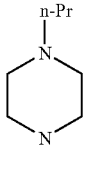 | n-Pr 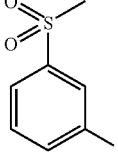 |
| (73) 1-[(3-fluorophenyl)sulfonyl]-5-(4-propyl-1-piperazinyl)-1H-indole | 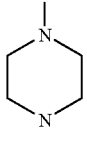 | n-Pr 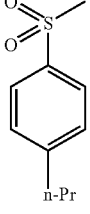 |
| (74) 5-(4-methyl-1-piperazinyl)-1-[(4-propylphenyl)sulfonyl]-1H-indole | 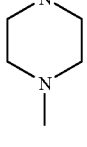 | 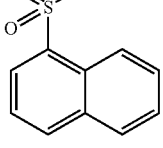 |
| (75) 5-(4-methyl-1-piperazinyl)-1-(1-naphthylsulfonyl)-1H-indole | 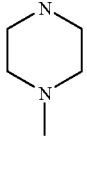 | 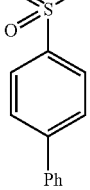 |
| (76) 1-([1,1'-biphenyl]-4-ylsulfonyl)-5-(4-methyl-1-piperazinyl)-1H-indole | 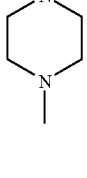 | |

TABLE II-continued

Compounds prepared according to synthetic scheme 3.

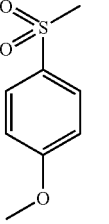

| EXAMPLE | —SO$_2$—Ar | R$^5$ |
|---|---|---|
| (77) 1-[(4-methoxyphenyl)sulfonyl]-5-(4-methyl-1-piperazinyl)-1H-indole | 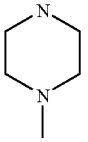 | 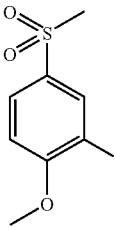 |
| (78) 1-[(3,4-dimethoxyphenyl)sulfonyl]-5-(4-methyl-1-piperazinyl)-1H-indole | 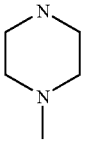 | 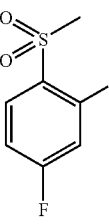 |
| (79) 1-[(2,4-difluorophenyl)sulfonyl]-5-(4-methyl-1-piperazinyl)-1H-indole | 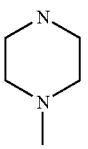 | 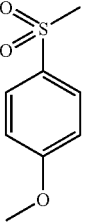 |
| (80) N-(4-Methoxybenzenesulfonyl)-5-(4-benzylpiperazin-1-yl)-indole, hydrochloride | 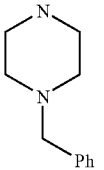 | 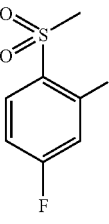 |
| (81) N-(2,4-Difluorobenzenesulfonyl)-5-(4-benzylpiperazin-1-yl)-indole, hydrochloride BVT.1311 | 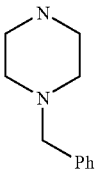 | |

TABLE II-continued

Compounds prepared according to synthetic scheme 3.

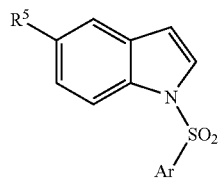

| EXAMPLE | —SO$_2$—Ar | R$^5$ |
|---|---|---|
| (82) N-(4-Butoxybenzenesulfonyl)-5-(4-benzylpiperazin-1-yl)-indole, hydrochloride | 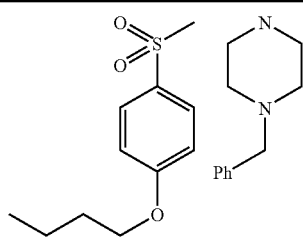 | |
| (83) N-(3,4-Dimethoxybenzenesulfonyl)-5-(4-benzylpiperazin-1-yl)-indole, hydrochloride | 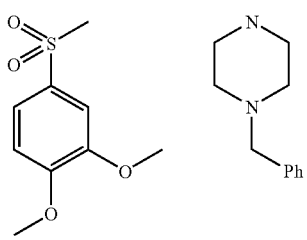 | |
| (84) N-(Biphenyl-4-sulfonyl)-5-(4-benzylpiperazin-1-yl)-indole, hydrochloride | 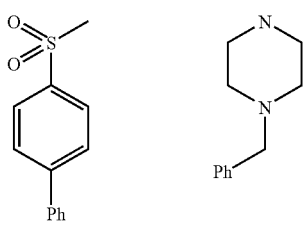 | |
| (85) N-(Napthalene-2-sulfonyl)-5-(4-benzylpiperazin-1-yl)-indole, hydrochloride | 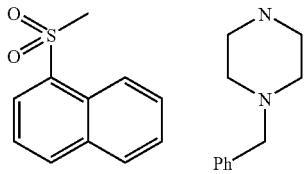 | |
| (86) N-(4-Propylbenzenesulfonyl)-5-(4-benzylpiperazin-1-yl)-indole, hydrochloride | 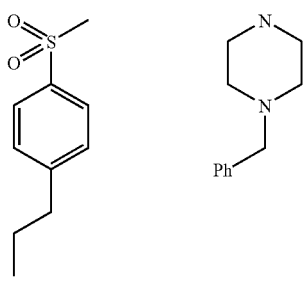 | |
| (87) N-(3-Fluorobenzenesulfonyl)-5-(4-benzylpiperazin-1-yl)-indole, hydrochloride | 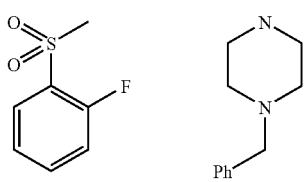 | |

TABLE II-continued

Compounds prepared according to synthetic scheme 3.

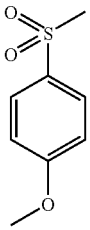

| EXAMPLE | —SO₂—Ar | R⁵ |
|---|---|---|
| (88) N-(4-Methoxybenzenesulfonyl)-5-(piperazin-1-yl)-indole, hydrochloride |  | 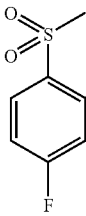 |
| (89) N-(2,4-Difluorobenzenesulfonyl)-5-(piperazin-1-yl)-indole, hydrochloride | 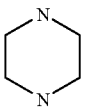 |  |
| (90) N-(4-Butoxybenzenesulfonyl)-5-(piperazin-1-yl)-indole, hydrochloride |  | 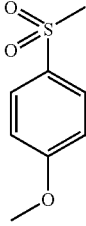 |
| (91) N-(3,4-Dimethoxybenzenesulfonyl)-5-(piperazin-1-yl)-indole, dihydrochloride | 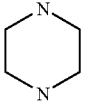 | 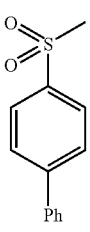 |
| (92) N-(Biphenyl-4-sulfonyl)-5-(piperazin-1-yl)-indole, dihydrochloride |  |  |

TABLE II-continued

Compounds prepared according to synthetic scheme 3.

| EXAMPLE | —SO₂—Ar | R⁵ |
|---|---|---|
| (93) N-(Napthalene-2-sulfonyl)-5-(piperazin-1-yl)-indole, dihydrochloride | naphthalen-2-ylsulfonyl | piperazin-1-yl |
| (94) N-(4-Propylbenzenesulfonyl)-5-(piperazin-1-yl)-indole, dihydrochloride | 4-propylphenylsulfonyl | piperazin-1-yl |
| (95) N-(3-Fluorobenzenesulfonyl)-5-(piperazin-1-yl)-indole, dihydrochloride | 2-fluorophenylsulfonyl | piperazin-1-yl |
| (96) N-Benzenesulfonyl-5-(piperazin-1-yl)-indole, dihydrochloride 1-(phenylsulfonyl)-5-(1-piperazinyl)-1H-indole | phenylsulfonyl | piperazin-1-yl |

EXAMPLE 63 (INTERMEDIATE)

5-Bromo-1-triisopropylsilyl-indole

5-Bromoindole (3.92 g; 20 mmol) was dissolved in DCM (100 mL) and DMF (1 mL). NaH (0.88 g, 22 mmol; 60% in oil) was added to the cooled solution. After stirring for 15 minutes, triisopropylsilyl chloride (3.86 g, 20 mmol) was added dropwise to the reaction mixture. After 3 h, water (1 mL) was added, followed by MgSO₄. The mixture was filtered and concentrated and the residue put through a silica column with hexane as eluent. The product was obtained as a pale yellow oil (5.96 g, 17 mmol; yield 85%). $^1$H NMR (CDCl$_3$) δ 1.13 (18 H, d, J=8), 1.67 (3 H, m), 6.55 (1 H, d, J=3), 7.21 (1 H, dd, J=9, 2), 7.24 (1 H, d, J=3), 7.36 (1 H, d, J=9) and 7.74 (1 H, d, J=2).

EXAMPLE 64 (INTERMEDIATE)

5-(4-Methylpiperazin-1-yl)-indole

5-Bromo-1-triisopropylsilyl-indole (5.8 g, 16.4 mmol), N-methylpiperazine (1.8 g, 18 numol), NaOt-Bu (2.2 g, 23 mmol), Pd(OAc)$_2$ (37 mg, 0.16 mmol), Pt-Bu$_3$ (66 mg, 0.33 nmmol) and xylene (30 mL) were mixed and heated to 130° C. under stirring for 5 h. The crude material was chromatographed on a silica column using DCM/MeOH 95/5 as eluent. Concentration of the main fractions left 5.6 g of an oil which was dissolved in MeCN (10 mL), 20 mL of a 1 M solution of tetrabutylammonium fluoride in THF was added and the mixture left over-night. The reaction mixture was put on a silica column and eluted with DCM/MeOH 95/5 to give the product as an oil (2 g, 9.3 mmol; yield 57 %) $^1$H NMR (CDCl$_3$) δ 2.37 (3 H, s), 2.64 (4 H, t, J=5), 3.19 (4 H, t, J=5), 6.44–6.48 (1 H, m), 6.95–7.00 (1 H, m), 7.16 (1 H, d, J=3), 7.18 (1 H, d, J=2), 7.29 (1H, d, J=9) and 8.12 (1 H, bs).

Intermediates 65–67 were prepared using the same method as for intermediate 64.

EXAMPLE 65 (INTERMEDIATE)

5-(4-Isopropylpiperazin-1-yl)-indole (0.46 g, 1.9 mmol; yield 63%), $^1$H NMR (CDCl$_3$) δ 1.12 (6 H, d, J=7), 2.70–2.78 (5 H, m), 3.15–3.22 (4 H, m), 6.45–6.49 (1 H, m), 6.97–7.01 (1 H, dm), 7.14–7.19 (2 H, m), 7.30 (1 H, d, J=9) and 8.05 (1 H, bs).

EXAMPLE 66 (INTERMEDIATE)

5-(4-Benzylpiperazin-1-yl)-indole (3.6 g, 12.4 mmol; yield 55%), $^1$H NMR (CDCl$_3$) δ 2.67 (4 H, t, J=5), 3.18 (4 H, t, J=5), 3.60 (2 H, s), 6.44–6.47 (1 H, m), 6.97 (2 H, dd, J=9, 3), 7.13–7.17 (2 H, m), 7.25–7.39 (5 H, m) and 8.01 (1 H, bs).

EXAMPLE 67 (INTERMEDIATE)

5-(4-Propylpiperazin-1-yl)-indole (0.54 g, 2.2 mmol; yield 24%), $^1$H NMR (CDCl$_3$) δ 0.94 (3 H, t, J=7), 1.53–1.62 (2 H, m), 2.37–2.43 (2 H, m), 2.65–2.73 (4 H, m), 3.17–3.22 (4 H, m), 6.45–6.48 (1 H, m), 6.96–7.00 (1 H, dm), 7.14–7.19 (2 H, m), 7.30 (1 H, d, J=9) and 8.13 (1 H, bs).

EXAMPLE 68

N-Benzenesulfonyl-5-(4-methylpiperazin-1-yl)-indole 5-(4-Methylpiperazin-1-yl)-indole (215 mg, 1 mmol), benzenesulfonylchloride (265 mg, 1.5 mmol) and Aliquat 336 (10 mg) were dissolved in DCM (10 mL). Aqueous NaOH (20%, 2 mL) was added and the mixture was stirred vigorously for 6 h. The organic layer was separated, dried and concentrated to give the crude as an oil that was purified on a silica column using DCM and MeOH as eluent. The pure fractions were concentrated to give an oil (260 mg, 0.66 mmol) $^1$H NMR (CDCl$_3$) δ 2.35 (3 H, s), 2.59 (4 H, t, J=5), 3.18 (4 H, t, J=5), 6.57 (1 H, d, J=4), 6.98–7.03 (2 H, m), 7.38–7.54 (4 H, m), 7.82–7.90 (3 H, m); MS (posES-FIA) 355.1345 M$^+$; Purity (HPLC chromsil C18) >98%.

Examples 69–87 were prepared using the same method as for Example 1. Examples 72–87 are reported as hydrochloride salts.

EXAMPLE 69

N-(4-Methylbenzenesulfonyl)-5-(4-methylpiperazin-1-yl)-indole (0.24 g, yield 59%) $^1$H NMR (CDCl$_3$) δ 2.33 (3 H, s), 2.37 (3 H, s), 2.61 (4 H, t, J=5), 3.18 (4 H, t, J=5), 6.55 (1 H, d, J=3), 6.98–7.30 (2 H, m), 7.19 (2 H, d, J=7, 7.47 (1 H, d, J=4), 7.72 (2 H, d, J=9) and 7.86 (1 H, d, J=9); MS (posES-FIA) 369.1502 M$^+$; Purity (HPLC chromsil C18) >98%.

EXAMPLE 70

N-Benzenesulfonyl-5-(4-isopropylpiperazin-1-yl)-indole (0.24 g, yield 57%), $^1$H NMR (CDCl$_3$) δ 1.12 (6 H, d, J=7), 2.68–2.77 (5 H, m), 3.15–3.25 (4 H, m), 6.57 (1 H, d, J=5), 6.98–7.04 (2 H, m), 7.39–7.44 (2 H, m), 7.46–7.54 (1 H, m) and 7.81–7.89 (3 H, m); MS (posES-FIA) 383.1655 M$^+$; Purity (HPLC chromsil C18) >98%.

EXAMPLE 71

N-(4-Methylbenzenesulfonyl)-5-(4-isopropylpiperazin-1-yl)-indole (0.29 g, yield 67%), $^1$H NMR (CDCl$_3$) δ 1.11 (6 H, d, J=6), 2.33 (3 H, s), 2.67–2.78 (5 H, m), 3.15–3.25 (4 H, m), 6.54 (1 H, d, J=4), 6.97–7.03 (2 H, m), 7.19 (2 H, d, J=8), 7.46 (1H, d, J=4), 7.67–7.81 (3 H, m) and 7.86 (1 H, d, J=9); MS (posES-FIA) 397.1823 M$^+$; Purity (HPLC chromsil C18) >90%.

EXAMPLE 72

N-(3,4-Dimethoxybenzenesulfonyl)-5-(4-propylpiperazin-1-yl)-indole, hydrochloride (0.27 g, yield 67%), $^1$H NMR (CDCl$_3$) δ 1.10 (3 H, t, J=7), 1.93–2.03 (2 H, m), 3.10–3.20 (2 H, m), 3.63–3.70 (4 H, m), 3.88 (3 H, s), 3.90 (3 H, s), 4.30–4.42 (2 H, m), 4.82–4.94 (2 H, m), 6.76 (1 H, d, J=4), 6.87–6.94 (2 H, m), 7.53–7.60 (2 H, m), 7.72–7.76 (1 H, m), 7.83–7.88 (1 H, m), 8.08–8.12 (1 H, m), 8.16–8.20 (1 H, m) and 13.45 (1 H, bs); MS (posES-FIA) 443.1871 M$^+$; Purity (HPLC chromsil C18) >75%.

EXAMPLE 73

N-(3-Fluorobenzenesulfonyl)-5-(4-propylpiperazin-1-yl)-indole, hydrochloride (0.16 g, yield 67%), $^1$H NMR (MeOH d6) δ 1.02 (3 H, t, J=7), 1.72–1.84 (2 H, m), 3.02–3.18 (4 H, m), 3.19–3.26 (2 H, m), 3.60–3.68 (2 H, m), 3.71–3.80 (2 H, m), 6.67 (1 H, d, J=4), 7.08–7.13 (1 H, m), 7.15–7.18 (1 H, m), 7.30–7.37 (1 H, m), 7.46–7.54 (1 H, m), 7.58–7.64 (2 H, m), 7.66–7.72 (1 H, m) and 7.86–7.91 (1 H, m); MS (posES-FIA) 401.1585 M$^+$; Purity (HPLC chromsil C18) >90%.

EXAMPLE 74

N-(4-Propylbenzenesulfonyl)-5-(4-methylpiperazin-1-yl)-indole, hydrochloride (0.15 g, yield 38%) $^1$H NMR (CDCl$_3$) δ 0.90 (3 H, t, J=7), 1.56–1.66 (2 H, m), 2.60 (2 H, t, J=8), 2.98 (3 H, s), 3.56–3.68 (4 H, m), 4.27–4.40 (2 H, m), 4.64–4.74 (2 H, m), 6.74 (1 H, d, J=3), 7.25–7.29 (2 H, m), 7.71–7.81 (4 H, m), 8.06–8.13 (2 H, m) and 13.89 (1 H, bs); MS posES-FIA) 397.1813 M$^+$; Purity (HPLC chromsil C18) >93%.

EXAMPLE 75

N-(1-Naphtalenesulfonyl)-5-(4-methylpiperazin-1-yl)-indole, hydrochloride (0.18 g, yield 45%) $^1$H NMR (CDCl$_3$) δ 2.97 (3 H, s), 3.59 (4 H, t, J=15), 4.35–4.46 (2 H, m), 4.68–4.78 (2 H, m), 6.75 (1 H, d, J=3), 7.50–7.76 (4 H, m), 7.88–7.98 (3 H, m), 8.11–8.15 (2 H, m), 8.34–8.38 (1 H, m), 8.62 (1 H, d, J=9) and 13.94 (1 H, bs); MS (posES-FIA) 405.1503 M$^+$; Purity (HPLC chromsil C18) >90%.

EXAMPLE 76

N-(Biphenyl-4-sulfonyl)-5-(4-methylpiperazin-1-yl)-indole, hydrochloride (0.13 g, yield 30%) $^1$H NMR (MeOH-d$_6$) δ 2.93 (3 H, s), 3.05–3.15 (2 H, m), 3.20–3.30 (2 H, m), 3.50–3.60 (2 H, m), 3.70–3.80 (2 H, m), 6.66 (1 H, d, J=5),7.11 (1 H, dd, J=9, 3), 7.16 (1 H, d, J=3), 7.32–7.43 (3 H, m), 7.51–7.56 (2 H, m), 7.61 (1 H, d, J=4), 7.66–7.70 (2 H, m) and 7.88–7.94 (3 H, m); MS posES-FIA) 431.1662 M$^+$; Purity (HPLC chromsil C18) >98%.

EXAMPLE 77

N-(4-Methoxybenzenesulfonyl)-5-(4-methylpiperazin-1-yl)-indole, hydrochloride (0.17 g, yield 44%) $^1$H NMR (CDCl$_3$) δ 2.98 (3 H, s), 3.55–3.68 (4 H, m), 3.82 (3 H, s), 4.30–4.45 (2 H, m), 4.66–4.76 (2 H, m), 6.72 (1 H, d, J=4), 6.93 (2 H, d, J=9), 7.71 (1 H, d, J=4), 7.74–7.79 (1 H, m), 7.83 (2 H, d, J=9), 8.10 (2 H, d, J=9) and 13.97 (1 H, bs); MS (posES-FIA) 385.1456 M$^+$; Purity (HPLC chromsil C18) >95%.

EXAMPLE 78

N-(3,4-Dimethoxybenzenesulfonyl)-5-(4-methylpiperazin-1-yl)-indole, hydrochloride (0.13 g, yield 28%) $^1$H NMR (CDCl$_3$) δ 2.98 (3 H, s), 3.55–3.70 (4 H, m), 3.88 (3 H, s), 3.89 (3 H, s), 4.32–4.45 (2 H, m), 4.66–4.78 (2 H, m), 6.75 (1 H, d, J=4), 6.85–6.93 (2 H, m), 7.53–7.58 (1 H, m), 7.73 (1 H, d, J=4), 7.77–7.82 (1 H, m), 8.08–8.14 (2 H, m) and 13.97 (1 H, bs); MS (posES-FIA) 415.1561 M$^+$; Purity (HPLC chromsil C18) >80%.

EXAMPLE 79

N-(2,4-Difluorobenzenesulfonyl)-5-(4-methylpiperazin-1-yl)-indole, hydrochloride (0.23 g, yield 53%) $^1$H NMR (CDCl$_3$) δ 2.2.99 (3 H, s), 3.55–3.68 (4 H, m), 4.35–4.45 (2 H, m), 4.71–4.82 (2 H, m), 6.77 (1 H, d, J=4), 6.84–6.93 (2 H, m), 7.04–7.12 (1 H, m), 7.75–7.82 (2 H, m), 7.98 (1 H, d, J=9), 8.10–8.20 (2H, m) and 13.88 (1H, bs); MS (posES-FIA) 391.1155 M$^+$; Purity (HPLC chromsil C18) >88%.

EXAMPLE 80

N-(4-Methoxybenzenesulfonyl)-5-(4-benzylpiperazin-1-yl)-indole, hydrochloride (0.34 g, yield 61%). $^1$H NMR (CD$_3$OD) δ 3.26–3.29 (8 H, m), 3.76 (3 H, s), 4.40 (2 H, s), 6.93 (1 H, d, J=9), 7.08 (1 H, dd, J=9, 3), 7.17 (1 H, d, J=3), 7.46–7.51 (3 H, m), 7.52–7.57 (3 H, m), 7.76 (2 H, d, J=9) and 7.86 (1 H, d, J=9); MS (posES-FIA) 461.1763 M$^+$; Purity (HPLC chromsil C18) >90%.

EXAMPLE 81

N-(2,4-Difluorobenzenesulfonyl)-5-(4-benzylpiperazin-1-yl)-indole, hydrochloride (0.30 g, yield 64%). 1H NMR (CD$_3$OD) δ 3.30–3.80 (8 H, m), 4.40 (2 H, s), 6.66 (1 H, d, J=4), 7.04–7.15 (3 H, m), 7.30 (1 H, d, J=3), 7.43–7.47 (3 H, m), 7.52–7.56 (2 H, m), 7.57–7.66 (1 H, m), 7.74 (1 H, d, J=9) and 8.06–8.14 (1 H, m); MS (posES-FIA) 467.1492 M$^+$; Purity (HPLC chromsil C18) >98%.

EXAMPLE 82

N-(4-Butoxybenzenesulfonyl)-5-(4-benzylpiperazin-1-yl)-indole, hydrochloride (0.30 g, yield 64%). $^1$H NMR (DMSO d$_6$) δ 0.86 (3 H, t, J=7), 1.29–1.42 (2 H, m), 1.55–1.69 (2 H, m), 3.05–3.37 (6 H, m), 3.60–3.70 (2 H, m), 3.97 (2 H, t, J=6), 4.35 (2 H, s), 6.70 (1 H, d, J=3), 7.02–7.15 (4 H, m), 7.43–7.50 (3 H, m), 7.65–7.71 (3 H, m), 7.78–7.86 (3 H, m) and 11.45 (1 H, bs); MS (posES-FIA) 503.2236 M$^+$; Purity (HPLC chromsil C18) >95%.

EXAMPLE 83

N-(3,4-Dimethoxybenzenesulfonyl)-5-(4-benzylpiperazin-1-yl)-indole, hydrochloride (0.36 g, yield 68%). $^1$H NMR (DMSO d$_6$) δ 3.10–3.40 (6 H, m), 3.65–3.85 (2 H, m), 3.76 (6 H, s), 4.35 (2 H, s), 6.70 (1 H, d, J=4), 7.04–7.14 (3 H, m), 7.34 (1 H, d, J=2), 7.42–7.47 (3 H, m), 7.50 (1 H, dd, J=9, 2), 7.65–7.70 (2 H, m), 7.73 (1 H, d, J=4), 7.83 (1 H, d, J=9) and 11.65 (1 H, bs); MS (posES-FIA) 491.1875 M$^+$; Purity (HPLC chromsil C18) >98%.

EXAMPLE 84

N-(Biphenyl-4-sulfonyl)-5-(4-benzylpiperazin-1-yl)-indole, hydrochloride (0.35 g, yield 64%). $^1$H NMR (DMSO d$_6$) δ 3.10–3.20 (4 H, m), 3.30–3.40 (2 H, m), 3.70–3.80 (2 H, m), 4.36 (2 H, s), 6.74 (1 H, d, J=4), 7.05–7.13 (2 H, m), 7.40–7.50 (6 H, m), 7.58–7.63 (2 H, m), 7.63–7.68 (2 H, m), 7.76 (1 H, d, J=4), 7.82–7.87 (3 H, m), 7.98 (2 H, d, J=9) and 10.81 (1 H, bs); MS (posES-FIA) 507.1981 M$^+$; Purity (HPLC chromsil C18) >98%.

EXAMPLE 85

N-(Napthalene-2-sulfonyl)-5-(4-benzylpiperazin-1-yl)-indole, hydrochloride (0.40 g, yield 55%). $^1$H NMR (DMSO d$_6$) δ 3.05–3.35 (6 H, m), 3.66 (2 H, d, J=12), 4.33 (2 H, s), 6.71 (1 H, d, J=4), 6.99 (1 H, dd, J=9, 2), 7.10 (1 H, d, J=4), 7.41–7.45 (3 H, m), 7.58–7.75 (6 H, m), 8.00 (1 H, d, J=4), 8.07 (1 H, d, J=8), 8.29 (1 H, d, J=9), 8.32 (1 H, d, J=7), 8.62 (1 H, d, J=9) and 11.53 (1 H, bs); MS posES-FIA) 481.1842 M$^+$; Purity (HPLC chromsil C18) >98%.

EXAMPLE 86

N-(4-Propylbenzenesulfonyl)-5-(4-benzylpiperazin-1-yl)-indole, hydrochloride (0.49 g, yield 63%). $^1$H NMR (DMSO d$_6$) δ 0.81 (3 H, t, J=7), 1.44–1.56 (2 H, m), 2.54 (2 H, t, J=8), 3.10–3.27 (6 H, m), 3.28–3.38 (2 H, m), 4.35 (2 H, s), 6.70 (1 H, d, J=4), 7.05–7.09 (1 H, m), 7.10–7.12 (1 H, m), 7.37 (2 H, d, J=8), 7.43–7.48 (3 H, m), 7.63–7.67 (2 H, m), 7.69 (1 H, d, J=4), 7.77–7.84 (3 H, m), and 11.37 (1 H, bs); MS (posES-FIA) 473.2152 M$^+$; Purity (HPLC chromsil C18) >98%.

EXAMPLE 87

N-(3-Fluorobenzenesulfonyl)-5-(4-benzylpiperazin-1-yl)-indole, hydrochloride (0.36 g, yield 70%). $^1$H NMR (DMSO d$_6$) δ 3.10–3.23 (2 H, m), 3.26–3.40 (4 H, m), 3.65–3.77 (2 H, m), 4.37 (2 H, s), 6.75 (1 H, d, J=4), 7.11 (1H, dd, J=9, 2), 7.17 (1 H, d, J=2), 7.40–7.45 (3 H, m), 7.48–7.56 (1 H, m), 7.58–7.65 (1 H, m), 7.65–7.71 (2 H, m), 7.73–7.78 (2 H, m), 7.80–7.86 (2 H, m) and 11.79 (1 H, bs); MS (posES-FIA) 449.1595 M$^+$; Purity (HPLC chromsil C18) >98%.

EXAMPLE 88

N-(4-Methoxybenzenesulfonyl)-5-(piperazin-1-yl)-indole, hydrochloride

N-(4-Methoxybenzenesulfonyl)-5-(4-benzylpiperazin-1-yl)-indole (0.25 g, 0.54 mmol) was dissolved in DCM (4 mL), a-chloroethyl chlorofonnate (0.150 g, 1.05 mmol) was added and the mixture left at room temperature for 2 h after which it was concentrated. MeOH (10 mL) was added and the mixture refluxed for 2 hrs and then concentrated to give the product (0.22 g, quantitative yield). $^1$H NMR (MeOH d$_6$) δ 3.39–3.47 (8 H, m), 3.77 (3 H, s), 6.64 (1 H, d, J=3), 6.94 (2 H, d, J=9), 7.15 (1 H, dd, J=9, 2), 7.26 (1 H, d, J=2), 7.59 (1 H, d, J=4), 7.80 (2 H, d, J=9) and 7.90 (1 H, d, J=9); MS (posES-FIA) 371.1304 M$^+$; Purity (HPLC chromsil C18) >98%. Examples 89–95 were prepared using the same procedure as in example 88.

EXAMPLE 89

N-(2,4-Difluorobenzenesulfonyl)-5-(piperazin-1-yl)-indole, hydrochloride (Isolated 0.20 g). $^1$H NMR (CDCl$_3$) δ 3.49–3.54 (4 H, m), 3.57–3.62 (4 H, m), 6.71 (1 H, d, J=4), 7.04–7.15 (2 H, m), 7.28 (1 H, dd, J=9,3), 7.51 (1 H, d, J=3), 7.62–7.65 (1 H, m), 7.81 (1 H, d, J=9) and 8.08–8.16 (1 H, m); MS posES-FIA) 377.1012 M$^+$; Purity (HPLC chromsil C18) >98%.

EXAMPLE 90

N-(4-Butoxybenzenesulfonyl)-5-(piperazin-1-yl)-indole, hydrochloride (Isolated 0.30 g) $^1$H NMR (DMSO d$_6$) δ 0.84 (3 H, t, J=8), 1.28–1.39 (2 H, m), 1.55–1.65 (2 H, m), 3.22–3.30 (4 H, m), 3.40–3.48 (4 H, m), 3.95 (2 H, t, J=7), 6.73 (1 H, d, J=4), 7.00 (2 H, d, J=9), 7.19 (1 H, d, J=9), 7.29 (1 H, bs), 7.71 (1 H, d, J=4), 7.84 (3 H, d, J=9) and 9.64 (1 H, bs); MS (posES-FIA) 413.1770 M$^+$; Purity (HPLC chromsil C18) >88%.

EXAMPLE 91

N-(3,4-Dimethoxybenzenesulfonyl)-5-(piperazin-1-yl)-indole, Dihydrochloride (Isolated 0.24 g ). $^1$H NMR (DMSO d$_6$) δ 3.28–3.36 (4 H, m), 3.48–3.55 (4 H, m), 3.75 (3 H, s), 3.76 (3 H, s), 6.76 (1 H, d, J=4), 7.05 (1 H, d, J=9), 7.23–7.44 (3 H, m), 7.53 (1 H, dd, J=9, 3), 7.80 (1 H, d, J=4), 7.93 (1 H, d, J=9), and 9.81 (2 H, bs); MS (posES-FIA) 401.1401 M$^+$; Purity (HPLC chromsil C18) >98%.

EXAMPLE 92

N-(Biphenyl-4-sulfonyl)-5-(piperazin-1-yl)-indole, Dihydrochloride (Isolated 0.21 g). $^1$H NMR (DMSO d$_6$) δ 3.16–3.23 (4 H, m), 3.27.3.32 (4 H. m), 6.74 (1H, d, J=4), 7.07–7.14 (2 H, m), 7.38–7.49 (3 H, m), 7.63–7.68 (2 H, m), 7.75 (1 H, d, J=4), 7.82–7.87 (3 H, m), 7.98 (2 H, d, J=9) and 9.00 (2 H, bs); MS (posES-FIA) 417.1519 M$^+$; Purity (HPLC chromsil C18) >98%.

EXAMPLE 93

N-(Napthalene-2-sulfonyl)-5-(piperazin-1-yl)-indole, Dihydrochloride (Isolated 0.25 g). $^1$H NMR (DMSO d$_6$) δ 3.15–3.25 (4 H, m), 3.30–3.36 (4 H, m), 6.73 (1 H, d, J=4), 7.05 (1 H, dd, J=9, 3), 7.17 (1 H, d, J=3), 7.61–7.74 (4 H, m), 8.02 (1 H, d, J=4), 8.07 (1 H, d, J=8), 8.30 (1 H, d, J=8), 8.33 (1 H, d, J=8), 8.62 (1 H, d, J=9) and 9.46 (2 H, bs); MS (posES-FIA) 391.1349 M$^+$; Purity (HPLC chromsil C18) >98%.

EXAMPLE 94

N-(4-Propylbenzenesulfonyl)-5-(piperazin-1-yl)-indole, Dihydrochloride (Isolated 0.24 g). $^1$H NMR (DMSO d$_6$) δ 0.80 (3 H, t, J=8), 1.44–1.55 (2 H, m), 2.53 (2 H, t, J=8), 3.18–3.26 (4 H, m), 3.36–3.42 (4 H, m), 6.73 (1 H, d, J=4), 7.14 (1 H, dd, J=9, 2), 7.21 (1 H, d, J=3), 7.36 (2 H, d, J=8), 7.71 (1 H, d, J=4), 7.79–7.85 (3 H, m), 9.52 (2 H, bs); MS (posES-FIA) 383.1679 M$^+$; Purity (HPLC chromsil C18) >98%.

EXAMPLE 95

N-(3-Fluorobenzenesulfonyl)-5-(piperazin-1-yl)-indole, Dihydrochloride (Isolated 0.18 g). $^1$H NMR (DMSO d$_6$) δ 3.31–3.28 (4 H, m), 3.32–3.43 (4 H, m), 6.77 (1 H, d, J=4), 7.14 (1 H, dd, J=9, 3), 7.19 (1 H, d, J=2), 7.50–7.58 (1 H, m), 7.59–7.66 (1 H, m), 7.73–7.79 (2 H, m), 7.80–7.87 (1 H, m) and 9.53 (2 H, bs); MS (posES-FIA) 359.1109 M$^+$, Purity (HPLC chromsil C18) >98%.

EXAMPLE 96

N-Benzenesulfonyl-5-(piperazin-1-yl)-indole, Dihydrochloride

1-Benzenesulfonyl-5-bromo-indole (0.336 g, 1 mmol), piperazine (0.516 g, 6 mmol), CsCO$_3$ (0.456 g, 1.4 mmol), Pd$_2$(dba)$_3$ (46 mg, 0.05 mmol), BINAP (62 mg, 0.1 mmol) and xylene (10 mL) were mixed and heated to 120° C. under stirring for 18 h. The product was isolated as the hydrochloride salt (0.05 g). $^1$H NMR (CDCl$_3$) δ 3.00–3.16 (8 H, m), 6.57 (1 H, d, J=3), 6.99 (1 H, s), 7.02 (1 H, d, J=3), 7.40 (2 H, t, J=8), 7.47–7.53 (2 H, m) and 7.81–7.90 (3 H, m); MS (posES-FIA) 341.1187 M$^+$; Purity (HPLC chromsil C18) >98%.

Scheme 4

Preparation of 3-substituted-1-arylsulfonyl indole, hydrochloride.

(i) p-Fluoro-sulfonylchloride, NaH, DMF.

EXAMPLE 97 (INTERMEDIATE)

3-(1-azabicyclo[2.2.2]oct-2-en-3-yl)-1H-indole, Oxalate

The compound was obtained according to the procedure described in the literature (Illi, V. O. *Synthesis* 1979, 136; Boettcher, H.; Seyfried, C.; Minck, K. O.; Wolf H. P. *Ger. Offen.* (1991), DE 90-4009565). $^1$H NMR (400 MHz, DMSO-$d_6$) δ 11.48 (s, 1 H), 7.75–7.70 (m, 2 H), 7.42 (d, J=8 Hz, 1 H), 7.20–7.05 (m, 2 H), 6.92 (s, 1 H), 3.34(s, 1H), 3,26 (br, 2 H), 2.84 (br, 2 H), 1.88 (br, 2 H), 1.63 (br, 2H).

EXAMPLE 98

3-(1-Azabicyclo[2.2.2]oct-2-en-3-yl)-1-[(4-fluorophenyl)sulfonyl]-1H-indole

At 0° C. 3-(3-indolyl)-2,3-dihydroquinuclidine (179 mg, 0.80 mmol) was added to a suspension of NaH (20 mg, 0.85 mmol) in DMF (1 mL) and stirred for 15 min. Then the 4-fluorophenylsulfonyl chloride (174 mg, 0.90 mmol) was added and the resulting solution was stirred for 30 min at 0° C. and 3h at room temperature. The DMF was evaporated and the resulting solid was chromatographed (Eluant $CH_2Cl_2$/MeOH, 90/10) to afford 100 mg (32%) of the desired compound. $^1$H NMR (270 MHz, DMSO-$d_6$) δ 8.25–8.10 (m, 3 H), 7.99 (d, J=8 Hz, 1 H), 7.83 (d, J=8 Hz, 1 H), 7.65–7.30 (m, 3 H), 7.20–7.05 (m, 2 H), 3,18 (br, 2 H), 2.75 (br, 2 H), 1.78 (br, 2 H), 1.50 (br, 2 H); MS (ESI+) for m/z 383 (M+H)$^+$.

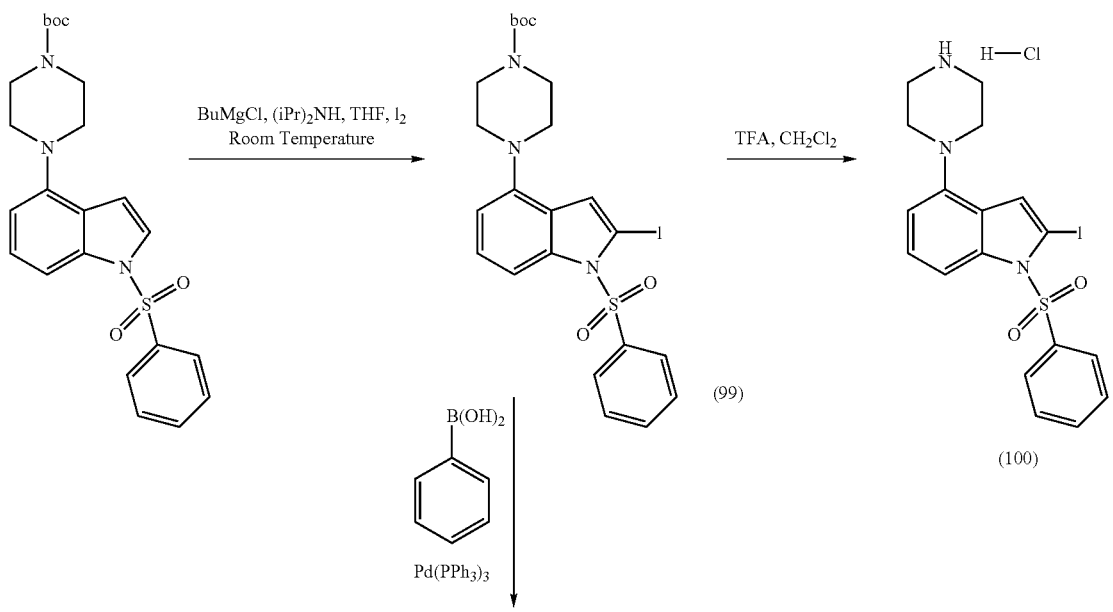

Scheme 5

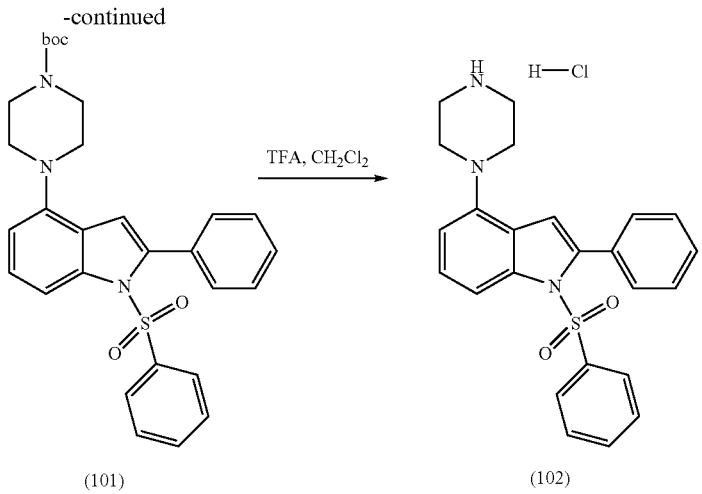

EXAMPLE 99 (INTERMEDIATE)

tert-Butyl 4-[2-iodo-1-(phenylsulfonyl)-1H-indol-4-yl]-1-piperazinecarboxylate

A mixture of butylmagnesium chloride (1 mL, 1mmol, 2.0 M in ether) and di-isopropyl amine (0.279 mL, 2 mmol) in dry THF (5 mL) was stirred for 4 h under inert atmosphere at room temperature. A solution of tert-butyl 4-[1-(phenylsulfonyl)-1H-indol-4-yl]-1-piperazinecarboxylate (220 mg, 0.5 mmol) in THF (2 mL) was added slowly and the resulting mixture stirred for 2 h at room temperature. A solution of iodine (380 mg, 2.2 mmol) in THF (2 mL) was added dropwise and the mixture was stirred overnight. After evaporation of the solvent in vacuo, the residue was treated with an aqueous solution of $NH_4Cl$ (10 mL). The mixture was extracted with $CH_2Cl_2$ (3×10 mL) and the combined organic layers were dried ($MgSO_4$) and concentrated in vacuo. The residue was purified by column chromatography ($SiO_2$) using $CH_2Cl_2$ as eluent to give 100 mg (35%).$^1$H NMR (500 MHz, $CDCl_3$) δ 8.05–7.80 (m, 3 H), 7.60–7.35 (m, 3 H), 7.19 (t, J=8 Hz, 1 H), 6.98 (s, 1 H), 6.72 (d, J=8 Hz, 1 H), 3.62 (m, 4 H), 3.05 (m, 4 H), 1.47 (m, 9 H); MS (ESI+) for m/z 568 (M+H)$^+$.

EXAMPLE 100

2-Iodo-1-(phenylsulfonyl)-4-(1-piperazinyl)-1H-indole hydrochloride

In $CH_2Cl_2$ (1 mL) tert-butyl 4-[2-iodo-1-(phenylsulfonyl)-1H-indol-4-yl]-1-piperazinecarboxylate (25 mg, 0.044 mmol) and HCl in ether (1 mL) were added and shaken for 2 h at room temperature. The resulting precipitate was filtered off and washed with ether giving 20 mg of the desired compound. $^1$H NMR (270 MHz, DMSO-$d_6$) δ 9.02 (br, 1 H), 7.90–7.80 (m, 3 H), 7.75–7.55 (m, 3 H), 7.32 (s, 1 H), 7.22 (t, J=8 Hz, 1 H), 6.79 (d, J=8 Hz, 1 H), 3.35–310 (in, 8 H); MS (ESI+) for m/z 468 (M+H)$^+$.

EXAMPLE 101 (INTERMEDIATE)

tert-Butyl 4-[2-phenyl-1-(phenylsulfonyl)-1H-indol-4-yl]-1-piperazinecarboxylate tert-Butyl 4-[2-iodo-1-(phenylsulfonyl)-1H-indol-4-yl]-1-piperazinecarboxylate(40 mg, 0.07 mmol), phenyl boronic acid (12 mg, 0.1 mmol), Pd(PPh$_3$)$_4$ (2 mg, 0.002 mmol) and a 2M aqueous solution of $K_2CO_3$ (0.075 mL) were stirred for 3 days at 80° C. in dimethoxyethane (2 mL). After evaporation of the solvent, the crude was purified by column chromatography ($SiO_2$) and led to 30 mg of the desired compound (80%). $^1$H NMR (270 MHz, DMSO-$d_6$) δ 8.02 (d, J=8 Hz, 1 H), 7.55–7.20 (in, 11 H), 6.78 (t, J=8 Hz, 1 H), 7.57 (s, 1 H), 3.58 (in, 4 H), 3.02 (in, 4 H), 1.48 (in, 9 H). MS (ESI+) for m/z 518 (M+H)$^+$.

EXAMPLE 102

2-Phenyl-1-(phenylsulfonyl)-4-(1-piperazinyl)-1H-indole hydrochloride tert-Butyl 4-[2-phenyl-1-(phenylsulfonyl)-1H-indol-4-yl]-1-piperazinecarboxylate (30 mg, 0.058 mmol) was dissolved in $CH_2Cl_2$ (1 mL) followed by addition of HCl in ether (1 mL). The reaction was shaken for 2 h at room temperature. The resulting precipitate was filtered off and washed with ether giving 20 mg of the desired compound (80%). $^1$H NMR (270 MHz, DMSO-$d_6$) δ 9.02 (br, 1 H), 7.90–7.80 (m, 3 H), 7.75–7.55 (m, 3 H), 7.32 (s, 1 H), 7.22 (t, J=8 Hz, 1 H), 6.79 (d, J=8 Hz, 1 H), 3.35–310 (m, 8 H). MS (ESI+) for m/z 418 (M+H)$^+$.

EXAMPLE 103 (INTERMEDIATE)

4-Trifluoromethanesulfonyloxy-2-methyl-1-tetrabutyldimethylsilylindole

4-Hydroxy-2-methylindole (3.0 g, 20 mmol) was dissolved in 30 mL of DCM followed by addition of triethylamine (4.2 mL). Solution was cooled (ice bath) and a solution of trifluoromethanesulfonic anhydride (6.3 g, 22 nmmol) in DCM (6 mL) was slowly added under stirring. After 10 minutes the solution was washed by aqueous $K_2CO_3$, dried ($K_2CO_3$) and solvent was evaporated. Compound was dissolved in THF (10 mL) and NaH (0.8 g of 80% suspension in oil) was added. TBDMSCl (3.3 g, 22 mmol) in THF (5 mL) was added. The solution was diluted by 20 mL of DCM, washed by aqueous $NH_4Cl$. Organic phase was dried and evaporated. The compound was purified by chromatography ($SiO_2$ hexane-ether). Yield 5.7 g (75%): $^1$H NMR ($CDCl_3$) δ 7.48 (d, J=7.9 Hz, 1 H), 7.10–6.96 (m, 2 H), 6.44 (s, 1 H), 2.50 (s, 3 H), 0.96 (s, 9 H), 0.64 (s, 6 H); MS (ESI) 381.1 (M+H).

EXAMPLE 104 (INTERMEDIATE)

4-(N-Boc-piperazinyl)-2-methyl-1-tetrabutyldimethylsilylindole 4-trifluoromethanesulfonyloxy-2-methyl-1-tetrabutyldimethylsilylindole (1.0 g, 2.6 numol) and boc-piperazine (0.73 g, 3.9 mmol) were reacted according to Method 1 to give 0.75 g (67%) of a solid: $^1$HNMR (CDCl$_3$) δ 7.20 (d, J=8.2 Hz, 1 H), 6.96 (t, 1 H), 6.55 (d, J=7.4 Hz, 1 H), 6.31 (s, 1 H), 3.63 (pt, 4 H), 3.11 pt, 4 H), 2.47 (s, 3 H), 1.48 (s, 9 H), 0.94 (s, 9 H), 0.64 (s, 6 H); MS (ESI) 417.4 (M+H).

EXAMPLE 105

4-Piperazinyl-2-methyl-1-benzosulfonylindole trifluoroacetate 4-(N-Boc-piperazinyl)-2-methyl-1-tetrabutyldimethylsilylindole (0.2 g, 0.48 mmol) was dissolved in ethyl acetate (5 ml) followed by the addition of a solution of sodium fluoride (0.1 g) in water (1 mL). Mixture was vigorously stirred (50° C.) for 2 h. The organic phase was separated, dried and evaporated. The crude was dissolved in DCM (10 mL) followed by the addition of benzosulfonylchloride (0.1 g, 0.58 mmol) and aqueous NaOH (0.5 mL, 50% water solution). The mixture was vigorously stirred for 1 h. Water (5 mL) was added, the organic phase was separated, dried and evaporated. The crude was dissolved in DCM (10 mL) and trifluoroacetic acid (1 mL) was added. After 3 h solvent was evaporated and compound was crystallized from ethanol. Yield 60 mg (54%): $^1$H NMR (CDCl$_3$) δ 7.83–7.77 (m, 3 H), 7.59–7.56 (m, 1 H), 7.50–7.46 (m, 2 H), 7.19 (t, 1 H), 6.81 (d, J=7.8 Hz, 1 H), 6.52 (s, 1 H), 3.41 (pt, 4 H), 3.30 (pt, 4 H), 2.61 (s, 3 H); $^{13}$CNMR (CDCl$_3$) δ 143.7, 138.8, 138.0, 136.6, 133.9, 129.2, 126.1, 124.3, 123.5, 111.5, 110.0, 107.3, 48.5, 43.8, 14.6; MS (ESI) 356.4 (M+H).

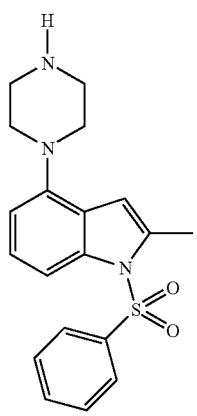

EXAMPLE 105

EXAMPLE 106 (INTERMEDIATE)

N-(t-Butyl-dimethylsilyl-4-(4-boc-homopiperazinyl)-indole

The title compound was prepared according as Example 4.
$^1$H NMR (D$_2$O) δ 9.37 (bs, 2 H) NH; 7.95 (m, 2 H); 7.73–7.56 (m, 4 H); 7.44 (d, J=8.2, 1 H); 7.18 (t, J=8.2, 1 H); 6.84 (m, 1 H); 6.65 (d, J=7.9, 1 H); 3.65 (m, 2 H); 3.46 (m, 2 H); 3.31 (m, 2 H); 3.19 (m, 2 H); 2.13 (m, 2 H). $^{13}$C NMR (D$_2$O): 145.7, 137.5, 136.3, 135.2, 130.4, 127.3, 126.2, 125.1, 121.3, 109.3, 105.4, 100.0, 50.8, 48.7, 46.6, 45.1, 25.6. MS (ESI) 356 (M+H).

EXAMPLE 107 (INTERMEDIATE)

1-Phenylsulfonyl-N-(t-butyl-dimethylsilyl-4-(4-boc-homopiperazinyl)-indole $^1$H NMR (CDCl$_3$) δ 7.86 (m, 2 H); 7.54–7.38 (m, 6 H); 7.4 (t, J=8.2, 1 H); 6.65–6.62 (m, 1 H); 3.63–3.41 (m, 8 H); 1.97 (m, 2 H); 1.43 (s, 9 H); MS (ESI) 456 (M+H).

EXAMPLE 108

1-Phenylsulfonyl-4-(homopiperazinyl)-indole hydrochloride $^1$H NMR (CDCl$_3$): 7.24 (m, 2 H); 7.09–7.07 (m, 6 H); 7.01 (t, J=8.1, 1 H); 6.53 (m, 1 H); 3.69–3.28 (m, 8 H); 2.06 (m, 2 H); 1.42 (s, 9 H); 0.91 (s, 9 H); 0.56 (s, 6 H). MS (ESI) 430 (M+H).

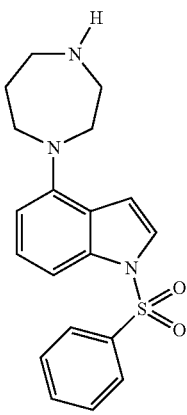

EXAMPLE 108

Pharmacological Tests

The ability of a compound of the invention to bind the 5HT$_6$ receptor can be determined using in vivo and in vitro assays known in the art. The biological activity of compounds prepared in the Examples was tested using different tests.

5-HT$_6$ Intrinsic Activity Assay

Antagonists at the 5HT$_6$ receptor were characterized by measuring inhibition of 5-HT induced increase in cAMP in HEK 293 cells expressing the human 5-HT$_6$ receptor (see Boess et al. (1997) Neuropharmacology 36: 713–720). Briefly, HEK293/5-HT$_6$ cells were seeded in polylysine coated 96-well plates at a density of 25 000/well and grown in DMEM (Dubecco's Modified Eagle Medium) (without phenol-red) containing 5% dialyzed Foetal Bovine Serum for 48 hours at 37° C. in a 5% CO$_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 μl dissolved in assay medium, the cells were incubated for 10 min at 37° C. in a 5% CO$_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times $EC_{50}$) evoked increase in cAMP, using the formula $Ki=IC_{50}/(1+[SHT]/EC_{50})$. Typically, the 5-$HT_6$ receptor affinity values (Ki) were in the range of from 0.1 nM to 2 µM.

Method for in vivo Assay of Reduction of Food Intake

Animals

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lepob and lean wild-type C57BI/6JBom; Bomholtsgaard, Denmark) 8–9 weeks with an average body weight of 50 g (obese) and 25 g (lean) are used in all the studies. The animals are housed singly in cages at 23+1° C., 40–60% humidity and have free access to water and standard laboratory chow. The 12/12-h light/dark cycle is set to lights off at 5 p.m. The animals are conditioned for at least one week before start of study.

Compounds

The test compounds are dissolved in solvents suitable for each specific compound such as cyclodextrin, cyclodextrin/methane sulfonic acid, polyethylene glycol/methane sulfonic acid, saline. Fresh solutions are made for each study. Doses of 30, 50 and 100 mg $kg^{-1}day^{-1}$ are used. The purity of the test compounds is of analytical grade.

Minipump Implantation

The animals are weighed at the start of the study and randomized based on body weight. Alzet osmotic minipumps (Model 2001D; infusion rate 8 ul/h) are used and loaded essentially as recommended by the Alzet technical information manual (Alza Scientific Products, 1997; Teeuwes and Yam, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min. It takes about 3 h to reach steady state delivery of the compound.

Food Intake Measurements

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

Determination of Plasma Concentration

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring is used.

A linear regression analysis of the standards forced through the origin is used to calculate the concentrations of the unknown samples.

Statistical Evaluation

Food consumption for 15 hours is measured for the three consecutive days and the percentage of basal level values is derived for each animal from the day before and after treatment. The values are expressed as mean±SD and ±SEM from eight animals per dose group. Statistical evaluation is performed by Kruskal-Wallis one-way ANOVA using the per cent basal values. If statistical significance is reached at the level of p<0.05, Mann-Whitney U-test for statistical comparison between control and treatment groups is performed.

What is claimed is:

1. A compound of formula (I):

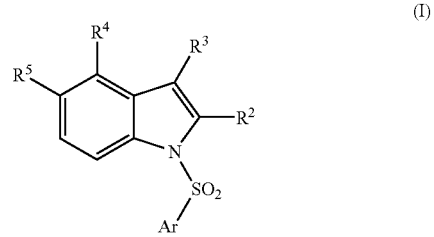

wherein

Ar is (1) a 5- to 10-membered monocyclic or bicyclic heterocyclic ring having 1 to 4 heteroatoms selected from the group consisting of oxygen, sulfur, or nitrogen, or (2) —$R^9$-phenyl;

wherein the phenyl, or heterocyclic ring is optionally substituted with halogen, $C_{1-6}$ alkyl, $CF_3$, hydroxyl, $C_{1-6}$ alkoxyl, $OCF_3$, $COCF_3$, CN, $NO_2$, phenyloxy, phenyl, $C_{1-6}$ alkylsulfonyl, $C_{2-6}$ alkenyl, —$NR^7R^8$, $C_{1-6}$ alkylcarboxyl, formyl, —$C_{1-6}$ alkyl-NH—CO-phenyl, —$C_{1-6}$ alkyl-CO—NH-phenyl, —NH—CO—$C_{1-6}$ alkyl, —CO—$NR^7R^8$, or $SR^7$; wherein each of $R^7$ and $R^8$ is independently H or $C_{1-6}$ alkyl; and $R^9$ is $C_{1-6}$ alkyl or $C_{2-6}$ alkenyl, either of which is optionally substituted with phenyl or phenyloxy;

$R^2$ is H, phenyl, I, or $C_{1-6}$ alkyl;

$R^3$ is H or 3-(1-azabicyclo[2.2.2]oct-2-en)yl;

$R^4$ is H or is selected from the group consisting of:

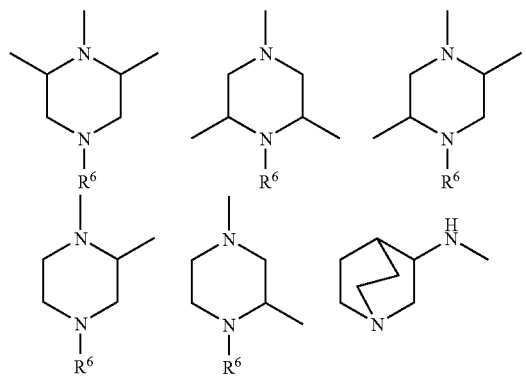

-continued

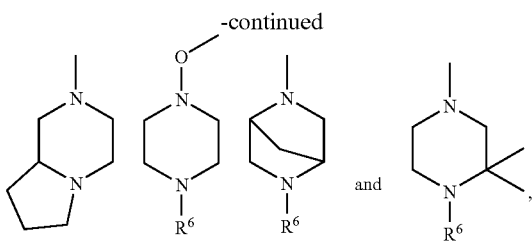

wherein R⁶ is H, C₁₋₆ alkyl, or benzyl; and
R⁵ is H, hydroxy, C₁₋₃ alkoxy, F, NO₂, CF₃, OCF₃, or is selected from the group consisting of:

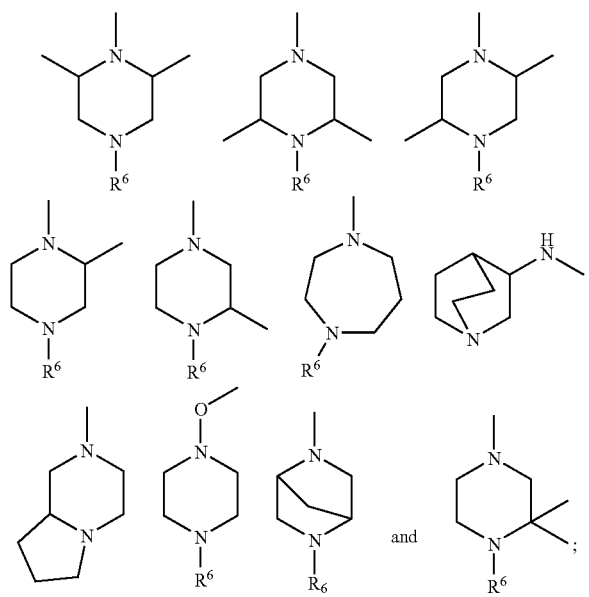

or a pharmaceutically acceptable salt, hydrate, or stereoisomer thereof, with the proviso that when R² is alkyl, R⁴ is not H.

2. The compound according to claim 1, wherein
Ar is
(1) cynnamoyl;
(2) benzyl;
(3) 1,1-diphenylethyl;
(4) a monocyclic or bicyclic heterocyclic ring selected from the group consisting of furyl, pyrrolyl, triazolyl, diazolyl, oxazolyl, thiazolyl, oxadiazolyl, isothiazolyl, isoxazolyl, thiadiazolyl, pyrimidyl, pyrazinyl, thienyl, imidazolyl, pyrazolyl, indolyl, quinolinyl, isoquinolinyl, benzofuryl, benzothienyl, and benzoxadiazolyl, said heterocyclic ring being optionally mono- or di-substituted substituted with halogen or C₁₋₆ alkyl;
R⁴ is H or is selected from the group consisting of:

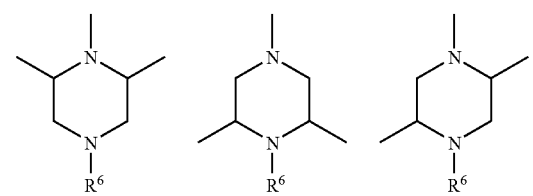

-continued

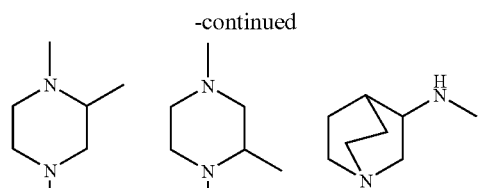

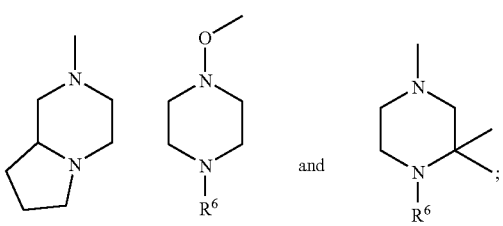

wherein R⁶ is H, C₁₋₆ alkyl, or benzyl; and
R⁵ is H, hydroxy, C₁₋₃ alkoxy, F, NO₂, CF₃, OCF₃ or is selected from the group consisting of:

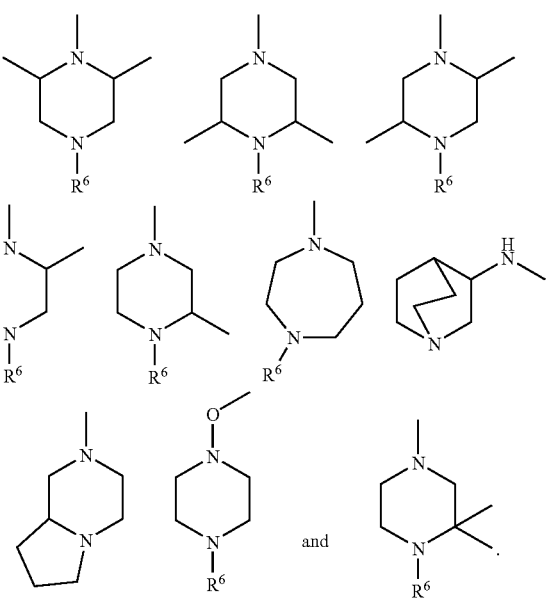

3. A compound according to claim 1, wherein
Ar is
(1) a 5- to 10-membered monocyclic or bicyclic heterocyclic ring having 1 to 4 heteroatoms selected from the group consisting of oxygen, sulfur, or nitrogen, or
(2) —R⁹-phenyl;
wherein the phenyl, naphthyl, or heterocyclic ring is optionally substituted with F, Cl, Br, C₁₋₆ alkyl, CF₃, hydroxyl, C₁₋₆ alkoxyl, OCF₃, phenyl, C₂₋₆ alkenyl, —NR⁷R⁸, —NH—CO—C₁₋₆ alkyl, or SR⁷, wherein each of R⁷ and R⁸ is independently H or C₁₋₆ alkyl; and R⁹ is C₁₋₂ alkyl;
R² is H, phenyl, I, or C₁₋₆ alkyl;

R⁴ is selected from the group consisting of

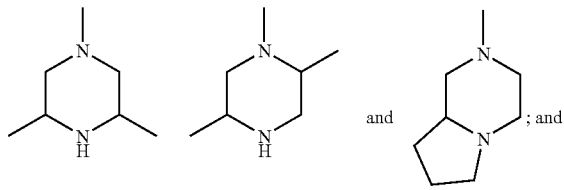

R⁵ is $C_{1-3}$ alkoxy or a heterocyclic ring selected from the group consisting of:

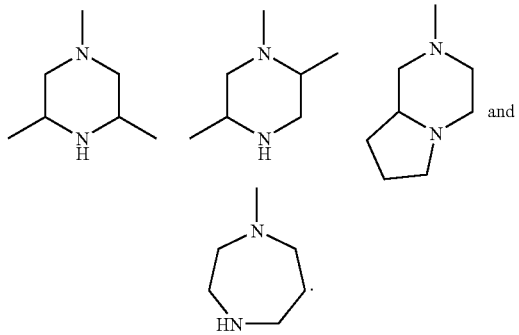

4. A compound according to claim 1, wherein Ar is a heterocyclic ring selected from the group consisting of fuiryl, pyrrolyl, triazolyl, diazolyl, oxazolyl, thiazolyl, oxadiazolyl, isothiazolyl, isoxazolyl, thiadiazolyl, pyridinyl, pyrimidyl, pyrazinyl, thienyl, imidazolyl, pyrazolyl, indolyl, quinolinyl, isoquinolinyl, benzofuryl, benzothienyl, and benzoxadiazolyl, each of which is optionally substitiuted with halogen, $C_{1-6}$ alkyl, $CF_3$, hydroxyl, $C_{1-6}$ alkoxyl, $OCF_3$, CN, $NO_2$, phenyloxy, phenyl, $C_{1-6}$ alkylsulfonyl, $C_{2-6}$ alkenyl, —$NR^7R^8$, $C_{1-6}$ alkylcarboxyl, formyl, —NH—CO—$C_{1-6}$ alkyl, —CO—$NR^7R^8$, or $SR^7$; wherein each of $R^7$ and $R^8$ is independently H or $C_{1-6}$ alkyl.

5. A compound according to claim 1, wherein Ar is a heterocyclic ring selected from the group consisting of pyridinyl, thienyl, imidazolyl, pyrazolyl, benzothienyl, and benzoxadiazolyl, each of which is optionally substituted with halogen or $C_{1-6}$ alkyl.

6. A compound according to claim 1, wherein Ar is 2-pyridyl, 3-pyridyl, or 4-pyridyl.

7. A compound according to claim 1, wherein Ar is a 5- to 7-membered aromatic, partially saturated, or completely saturated heterocyclic ring having 1 to 4 heteroatoms selected from the group consisting of O, S, or $NR^{10}$, where $R^{10}$ is H, $C_{1-6}$ alkyl, —CO—$CF_3$, or absent.

8. A compound according to claim 1, wherein Ar is —$R^9$-phenyl, wherein $R^9$ is $C_{1-3}$ alkyl or $C_{2-3}$ alkenyl, either of which is optionally substituted with phenyl or phenyloxy, each phenyl being optionally substituted with F, Cl, Br, methyl, $CF_3$, $C_{1-4}$ alkoxyl, $OCF_3$, CN, $NO_2$, phenyloxy, phenyl, methylsulfonyl, or —$NR^7R^8$; and each of $R^7$ and $R^8$ being independently H or $C_{1-6}$ alkyl.

9. A compound according to claim 1, wherein each of $R^2$ and $R^3$ is H.

10. A compound according to claim 1, wherein $R^4$ is independently a heterocyclic ring selected from the group consisting of:

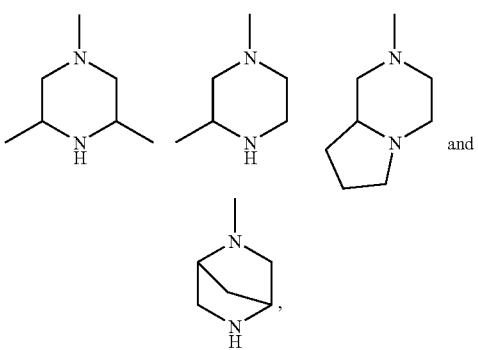

and $R^5$ is independently H or a heterocyclic ring selected from the group consisting of:

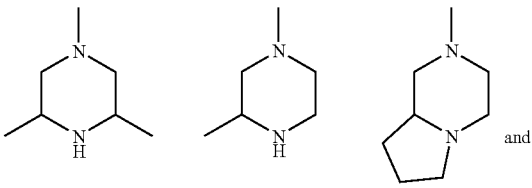

wherein $R^6$ is H, $C_{1-3}$ alkyl, or benzyl.

11. A compound according to claim 1, wherein Ar is a heterocyclic ring selected from the group consisting of pyridinyl, thienyl, imidazolyl, pyrazolyl, benzothienyl, and benzoxadiazolyl, each being optionally substituted with halogen or $C_{1-6}$ alkyl; each of $R^2$ and $R^3$ is H; and $R^4$ is independently a heterocyclic ring selected from the group consisting of:

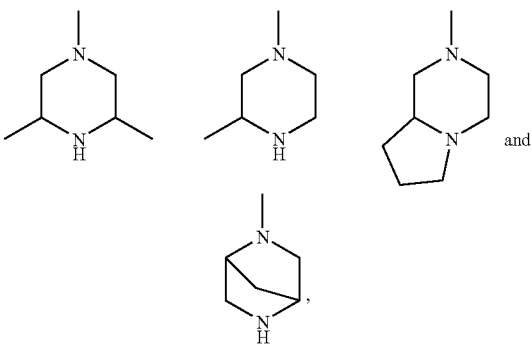

and $R^5$ is independently H or a heterocyclic ring selected from the group consisting of:

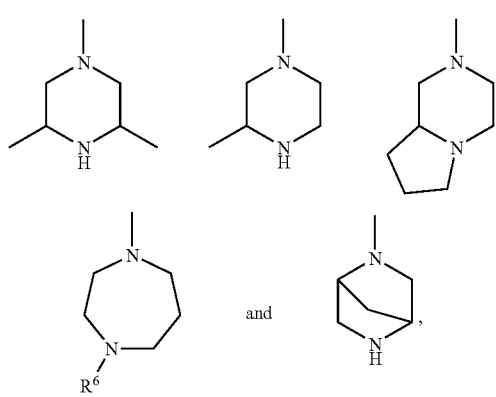

wherein R⁶ is H, C$_{1-3}$ alkyl, or benzyl.

12. A compound according to claim 1, wherein Ar is 2-pyridyl, 3-pyridyl, or 4-pyridyl; each of R² and R³ is H; and R⁴ is independently a heterocyclic ring selected from the group consisting of:

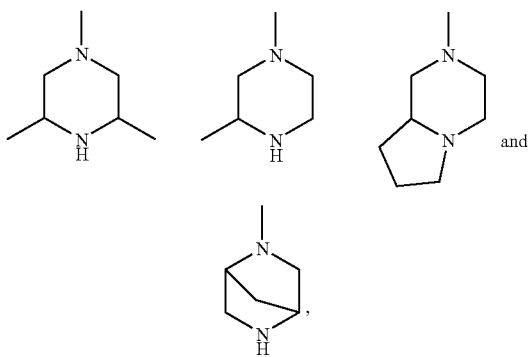

and R⁵ is independently H or a heterocyclic ring selected from the group consisting of:

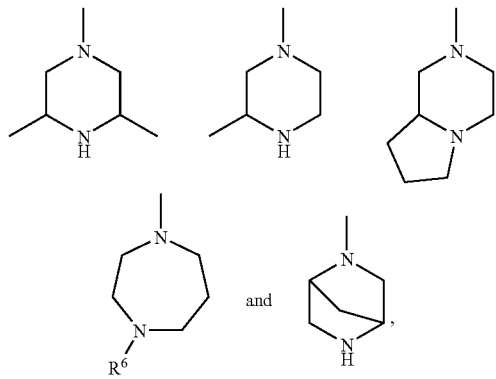

wherein R⁶ is H, C$_{1-3}$ alkyl, or benzyl.

13. A compound according to claim 1, wherein Ar is —R⁹-phenyl; each of R² and R³ is H; and R⁴ is independently a heterocyclic ring selected from the group consisting of:

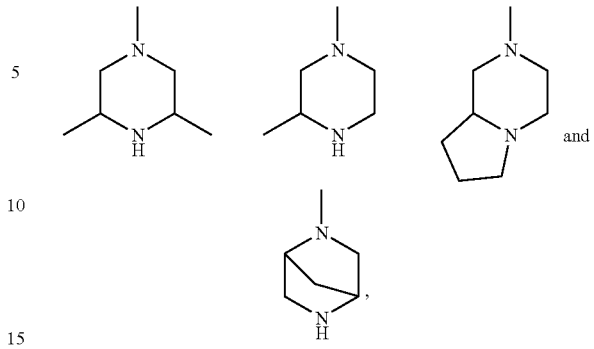

and R⁵ is independently H or a heterocyclic ring selected from the group consisting of:

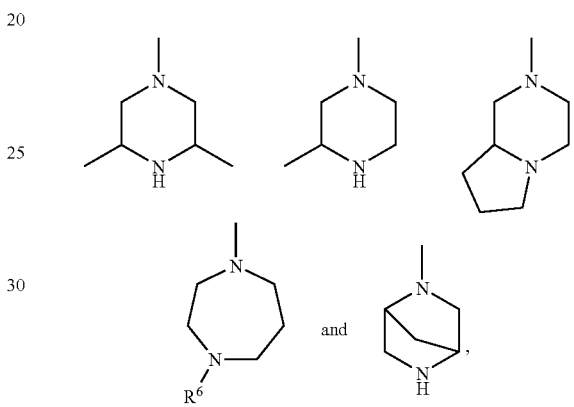

wherein R⁶ is H, C$_{1-3}$ alkyl, or benzyl; R⁹ is C$_{1-3}$ alkyl or C$_{2-3}$ alkenyl, either of which is optionally substituted with phenyl or phenyloxy; each phenyl being optionally substituted with F, Cl, Br, methyl, CF₃, C$_{1-4}$ alkoxyl, OCF₃, CN, NO₂, phenyloxy, phenyl, methylsulfonyl, or —NR⁷R⁸; and each of R⁷ and R⁸ being independently H or C$_{1-6}$ alkyl.

14. A compound of formula (I):

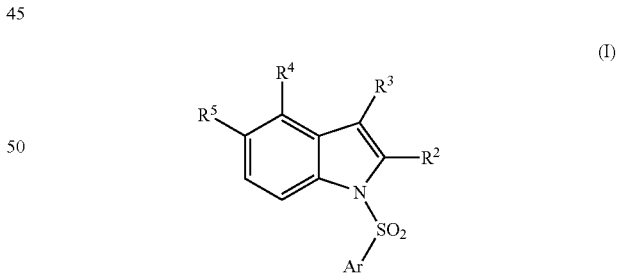

wherein
Ar is
(3) a 5- to 10-membered monocyclic or bicyclic heterocyclic ring having 1 to 4 heteroatoms selected from the group consisting of oxygen, sulfur, or nitrogen, or
(4) —R⁹-phenyl;
wherein the phenyl, or heterocyclic ring is optionally substituted with halogen, C$_{1-6}$ alkyl, CF₃, hydroxyl, C$_{1-6}$ alkoxyl, OCF3, COCF3, CN, NO₂, phenyloxy, phenyl, C$_{1-6}$ alkylsulfonyl, C$_{2-6}$ alkenyl, —NR⁷R⁸, C$_{1-6}$ alkylcarboxyl, formyl, —C$_{1-6}$ alkyl-NH—CO-phenyl, —C$_{1-6}$ alkyl-CO—

NH-phenyl, —NH—CO—C$_{1-6}$ alkyl, —CO—NR$^7$R$^8$, or SR$^7$; wherein each of R$^7$ and R$^8$ is independently H or C$_{1-6}$ alkyl; and R$^9$ is C$_{1-6}$ alkyl or C$_{2-6}$ alkenyl, either of which is optionally substituted with phenyl or phenyloxy;

R$^2$ is H, phenyl, I, or C$_{1-6}$ alkyl;

R$^3$ is H or 3-(1-azabicyclo[2.2.2]oct-2-en)yl;

R$^4$ is H or is selected from the group consisting of:

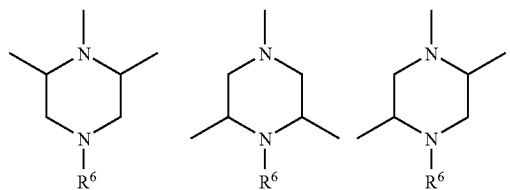

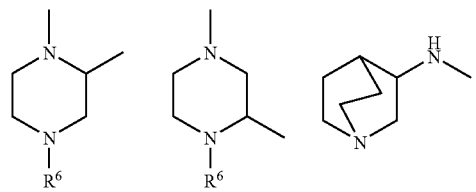

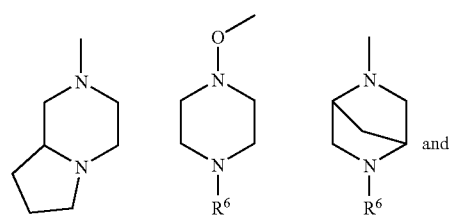

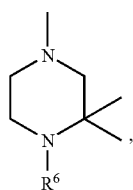

wherein R$^6$ is H, C$_{1-6}$ alkyl, or benzyl; and

R$^5$ is hydroxy, C$_{1-3}$ alkoxy, F, NO$_2$, CF$_3$, OCF$_3$, or is selected from the group consisting of:

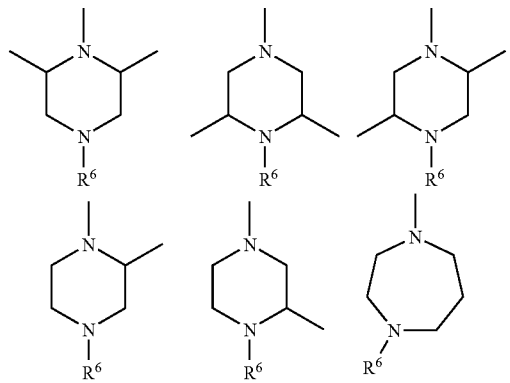

-continued

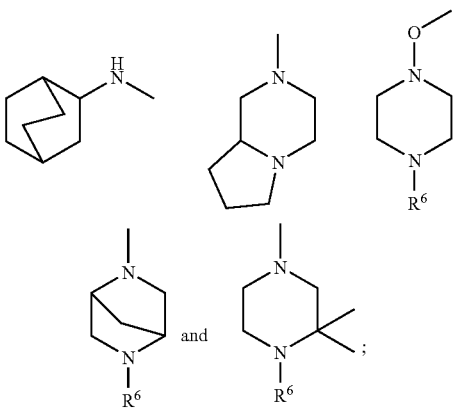

or a pharmaceutically acceptable salt, hydrate, or stereoisomer thereof, with the proviso that when R$^2$ is alkyl, R$^4$ is not H.

15. The compound of claim 1, wherein R$^5$ is H.

16. The compound of claim 14, wherein R$^4$ is H.

17. A compound that is 3-(1-azabicyclo[2.2.2]oct-2-en-3-yl)-1-[(4-fluorophenyl)sulfonyl]-1H-indole.

18. A pharmaceutical composition comprising a compound of claim 14 or 16 and a pharmaceutically acceptable carrier.

19. A method of treatment of schizophrenia or depression comprising administering to a patient in need thereof a therapeutically effective amount of a compound according to claim 14.

20. A method of treating schizophrenia or depression, comprising administering to a patient in need thereof a therapeutically effective amount of a compound according to claim 14.

21. A method of treating schizophrenia or depression, comprising administering to a patient in need thereof a therapeutically effective amount of a compound according to claim 15 or 16.

22. A compound according to claim 4, wherein R$^4$ is independently H or a heterocyclic ring selected from the group consisting of:

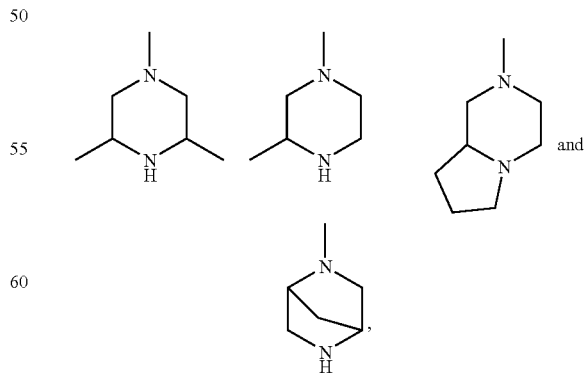

and R$^5$ is independently a heterocyclic ring selected from the group consisting of:

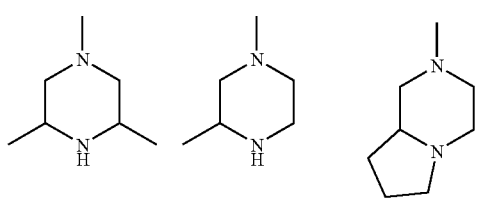

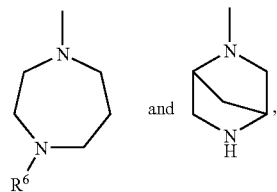

wherein $R^6$ is H, $C_{1-3}$ alkyl, or benzyl.

23. A compound according to claim 1, wherein Ar is a heterocyclic ring selected from the group consisting of pyridinyl, thienyl, imidazolyl, pyrazolyl, benzothienyl, and benzoxadiazolyl, each being optionally substituted with halogen or $C_{1-6}$ alkyl; each of $R^2$ and $R^3$ is H; and $R^4$ is independently H or a heterocyclic ring selected from the group consisting of:

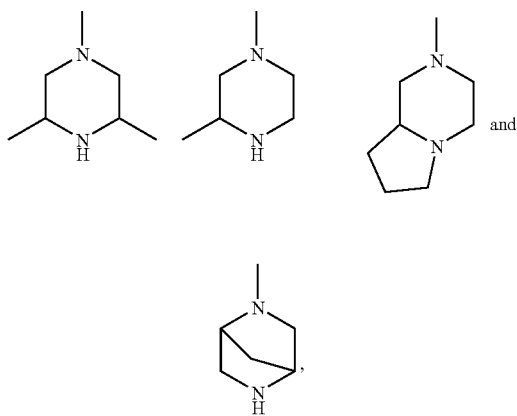

and $R^5$ is independently a heterocyclic ring selected from the group consisting of:

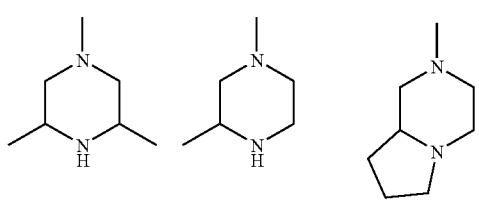

-continued

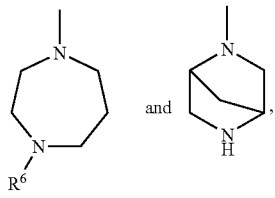

wherein $R^6$ is H, $C_{1-3}$ alkyl, or benzyl.

24. A compound according to claim 14, wherein Ar is 2-pyridyl, 3-pyridyl, or 4-pyridyl; each of $R^2$ and $R^3$ is H; and $R^4$ is independently H or a heterocyclic ring selected from the group consisting of:

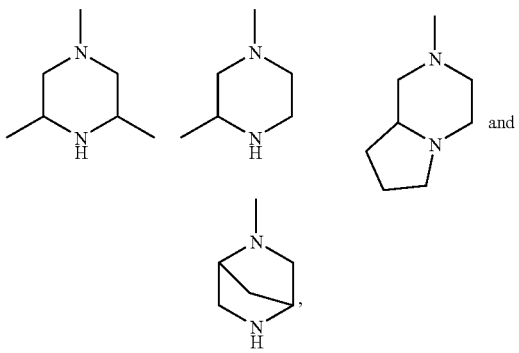

and $R^5$ is independently a heterocyclic ring selected from the group consisting of:

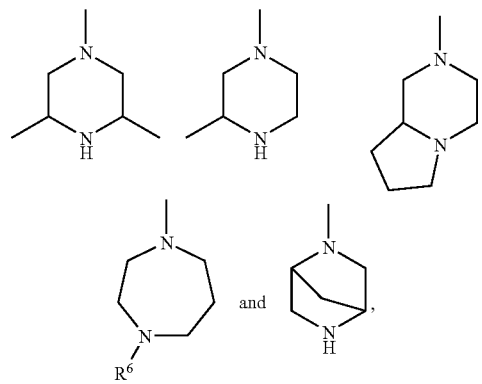

wherein $R^6$ is H, $C_{1-3}$ alkyl, or benzyl.

25. A compound according to claim 1, wherein Ar is —$R^9$-phenyl; each of $R^2$ and $R^3$ is H; and $R^4$ is independently H or a heterocyclic ring selected from the group consisting of:

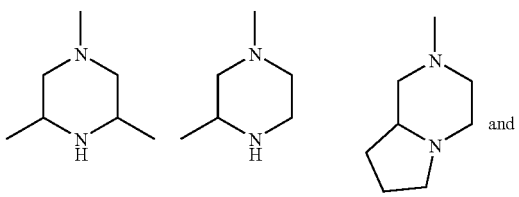

-continued

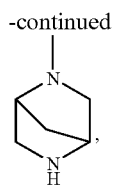

and R⁵ is independently a heterocyclic ring selected from the group consisting of:

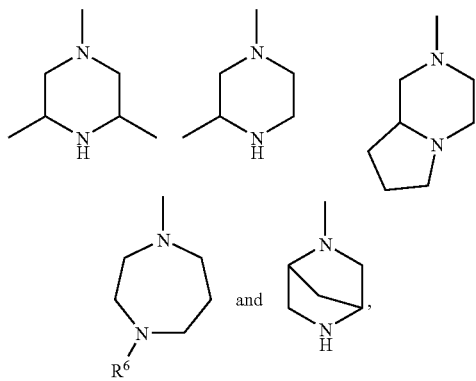

wherein R⁶ is H, $C_{1-3}$ alkyl, or benzyl; R⁹ is $C_{1-3}$ alkyl or $C_{2-3}$ alkenyl, either of which is optionally substituted with phenyl or phenyloxy; each phenyl being optionally substituted with F, Cl, Br, methyl, $CF_3$, $C_4$ alkoxyl, $OCF_3$, CN, $NO_2$, phenyloxy, phenyl, methylsulfonyl, or —$NR^7R^8$; and each of $R^7$ and $R^8$ being independently H or $C_{1-6}$ alkyl.

26. The compound according to claim 14, wherein
Ar is
(1) cinnamoyl;
(2) benzyl;
(3) 1,1-diphenylethyl;
(4) a monocyclic or bicyclic heterocyclic ring selected from the group consisting of furyl, pyrrolyl, triazolyl, diazolyl, oxazolyl, thiazolyl, oxadiazolyl, isothiazolyl, isoxazolyl, thiadiazolyl, pyrimidyl, pyrazinyl, thienyl, imidazolyl, pyrazolyl, indolyl, quinolinyl, isoquinolinyl, benzofuryl, benzothienyl, and benzoxadiazolyl, said heterocyclic ring being optionally mono- or di-substituted substituted with halogen or $C_{1-6}$ alkyl;
$R^4$ is H or is selected from the group consisting of:

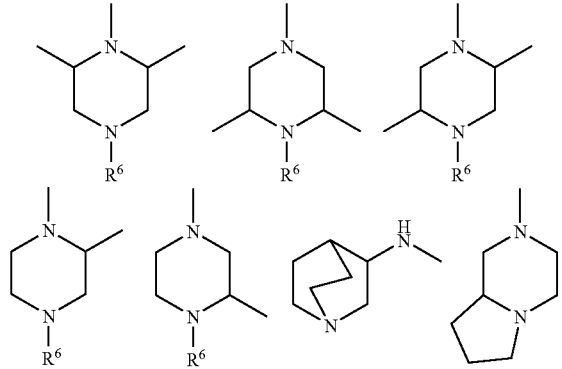

-continued

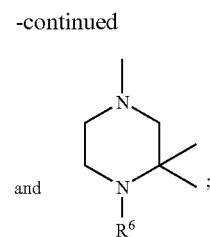

wherein $R^6$ is H, $C_{1-6}$ alkyl, or benzyl; and
$R^5$ is hydroxy, $C_{1-3}$ alkoxy, F, $NO_2$, $CF_3$, $OCF_3$ or is selected from the group consisting of:

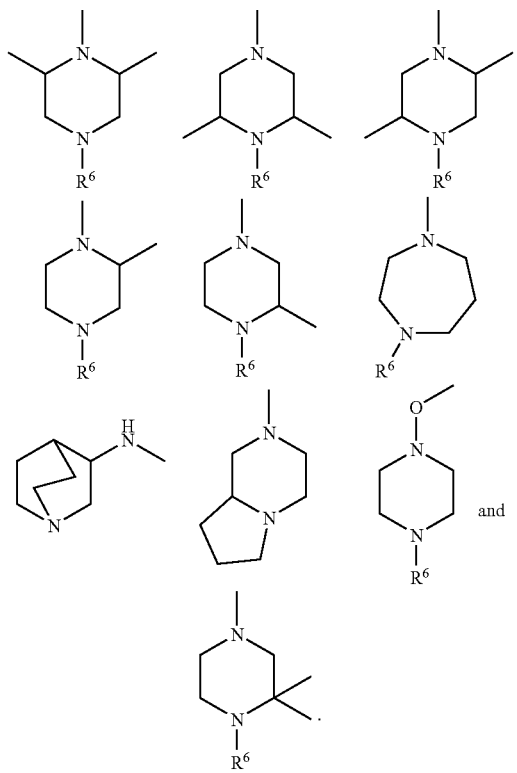

27. A compound of formula (I):

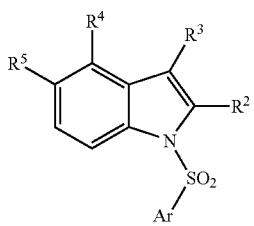

(I)

wherein
$R^1$ is —$SO_2Ar$; —$SO_2(alkyl)$;
Ar is a bicyclic heterocyclic ring or a 5- to 7-membered partially or completely saturated heterocyclic ring each having 1 to 4 heteroatoms selected from the group consisting of oxygen, sulfur, or nitrogen; and alkyl is linear or branched $C_{1-6}$ alkyl;

R² is H or linear or branched C₁₋₄ alkyl;
R³ is H, or 3-(1-azabicyclo[2.2.2]oct-2-en)yl, or 3-quinuclidinyl;
R⁴ is H or the following amine groups:

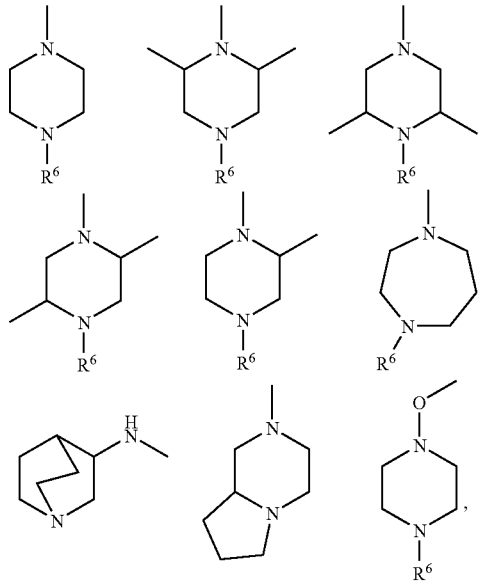

wherein R⁶ is H or a linear or branched C₁₋₆ alkyl; and
R⁵ is R⁴ or H, hydroxy, C₁₋₃ alkoxy, F, NO₂, CF₃, OCF₃; and pharmaceutically acceptable salts, hydrates, or stereoisomeric forms thereof.

28. The compound of claim 27, wherein the compound is selected from:
1-[(5 chloro-3-methyl-1-benzothien-2-yl)sulfonyl]-4-(1-piperazinyl)-1H-indole, or
1-[(5 chloro-3-methyl-1-benzothien-2-yl)sulfonyl]-5-(1-piperazinyl)-1H-indole.

29. A compound of formula (I):

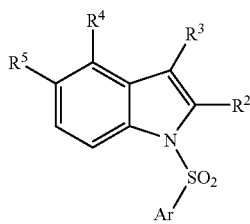

(I)

wherein
Ar is
(1) phenyl, or
(2) naphthyl,
wherein the phenyl or naphthyl ring is optionally substituted with halogen, C₁₋₆ alkyl, CF₃, hydroxyl, C₁₋₆ alkoxyl, OCF₃, COCF₃, CN, NO₂, phenyloxy, phenyl, C₁₋₆ alkylsulfonyl, C₂₋₆ alkenyl, —NR⁷R⁸, C₁₋₆ alkylcarboxyl, formyl, —C₁₋₆ alkyl-NH—CO-phenyl, —C₁₋₆ alkyl-CO—NH-phenyl, —NH—CO—C₁₋₆ alkyl, —CO—NR⁷R⁸, or SR⁷; wherein each of R⁷ and R⁸ is independently H or C₁₋₆ alkyl; and R⁹ is C₁₋₆ alkyl or C₂₋₆ alkenyl, either of which is optionally substituted with phenyl or phenyloxy;
R² is H, phenyl, I, or C₁₋₆ alkyl;

R³ is H or 3-(1-azabicyclo[2.2.2]oct-2-en)yl;
R⁴ is selected from the group consisting of:

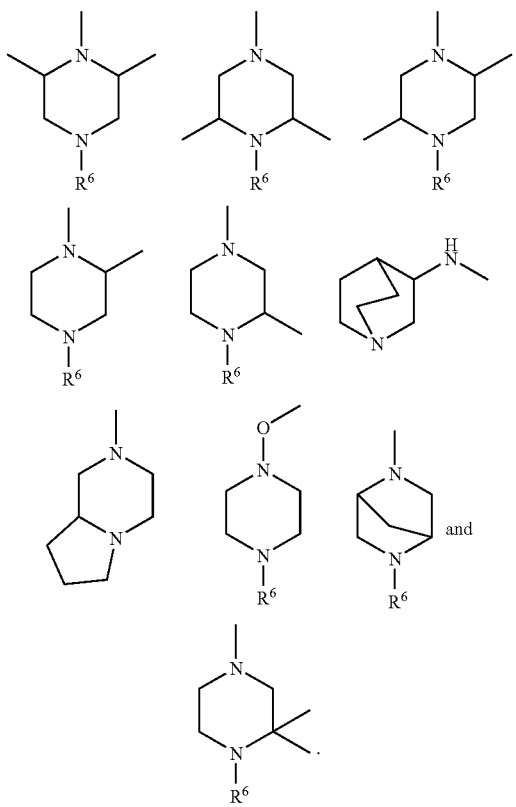

wherein R⁶ is H, C₁₋₆ alkyl, or benzyl; and
R⁵ is H, hydroxy, C₁₋₃ alkoxy, F, NO₂, CF₃, OCF₃, or is selected from the group consisting of:

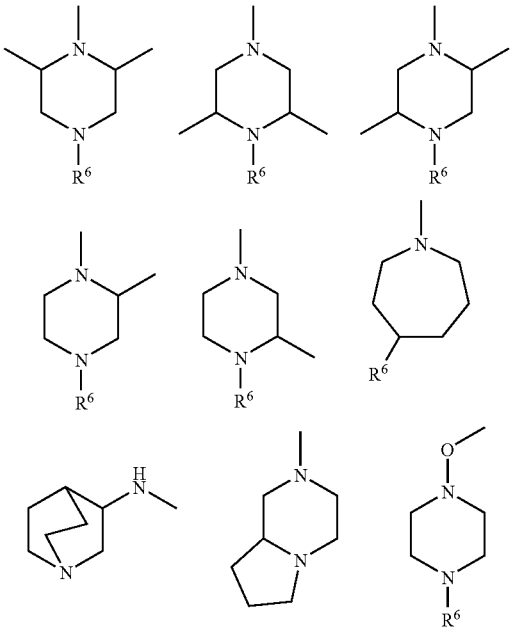

-continued

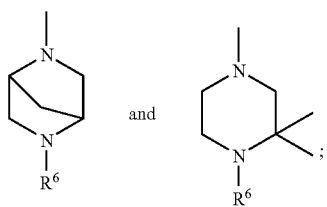
and or a pharmaceutically acceptable salt, hydrate, or stereoisomer thereof, with the proviso that when $R^2$ is alkyl, $R^4$ is not H.

30. The compound according to claim 29, wherein

Ar is (1) phenyl that is unsubstituted or optionally mono- or poly-substituted with halogen, $C_{1-6}$ alkyl, $CF_3$, hydroxyl, $C_{1-6}$ alkoxyl, $OCF_3$, CN, $NO_2$, phenyloxyl, phenyl, alkylsulfonyl, $C_{1-6}$ alkenyl, —$NH_2$, —$NHR^7$, —$NR^7R^8$, $C_{1-6}$ alkylcarboxyl, formyl, —NH—CO—$C_{1-6}$ alkyl, —CO—$NR^7R^8$, or $SR^7$ wherein each of $R^7$ and $R^8$ is independently H or $C_{1-6}$ alkyl;

(2) 1-naphthyl or 2-naphthyl that is unsubstituted or optionally mono- or poly-substituted with halogen, $C_{1-6}$ alkyl, $CF_3$, hydroxyl, $C_{1-6}$ alkoxyl, $OCF_3$, CN, $NO_2$, phenyloxyl, phenyl, alkylsulfonyl, $C_{2-6}$ alkenyl, —$NH_2$, —$NHR^7$, —$NR^7R^8$, $C_{1-6}$ alkylcarboxyl, formyl, —NH—CO—$C_{1-6}$ alkyl, —CO—$NR^7R^8$, or $SR^7$ wherein each of $R^7$ and $R^8$ is independently H or $C_{1-6}$ alkyl;

$R^4$ selected from the group consisting of:

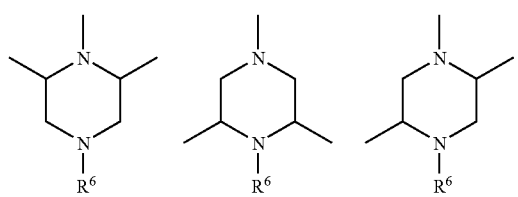

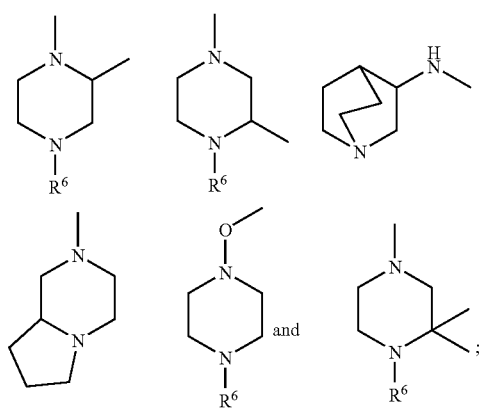

wherein $R^6$ is H, $C_{1-6}$ alkyl, or benzyl; and $R^5$ is H, hydroxy, $C_{1-3}$ alkoxy, F, $NO_2$, $CF_3$, $OCF_3$ or is selected from the group consisting of:

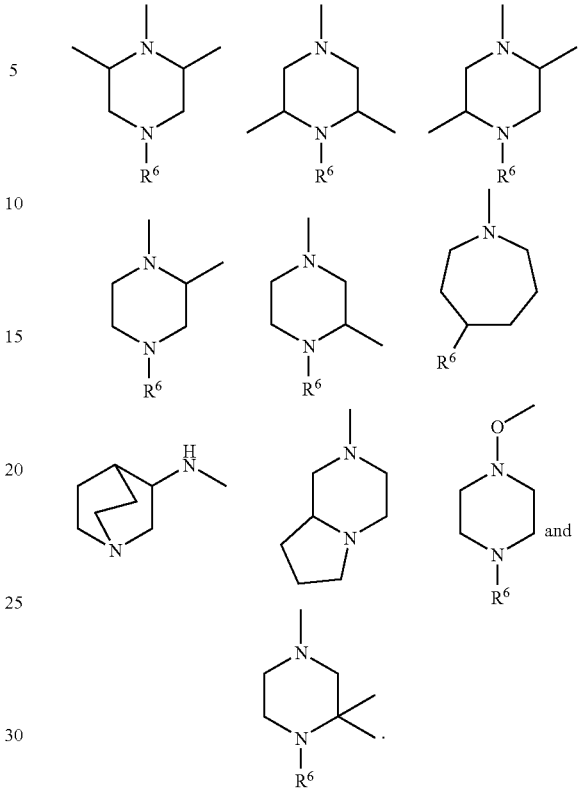

31. A compound according to claim 29, wherein

Ar is (1) phenyl, (2) 1-naphthyl or 2-naphthyl, wherein the phenyl or naphthyl ring is optionally substituted with F, Cl, Br, $C_{1-6}$ alkyl, $CF_3$, hydroxyl, $C_{1-6}$ alkoxyl, $OCF_3$, phenyl, $C_{2-6}$ alkenyl, —$NR^7R^8$, —NH—CO—$C_{1-6}$ alkyl, or $SR^7$, wherein each of $R^7$ and $R^8$ is independently H or $C_{1-6}$ alkyl; and $R^9$ is $C_{1-2}$ alkyl;

$R^2$ is H, phenyl, I, or $C_{1-6}$ alkyl;

$R^4$ selected from the group consisting of:

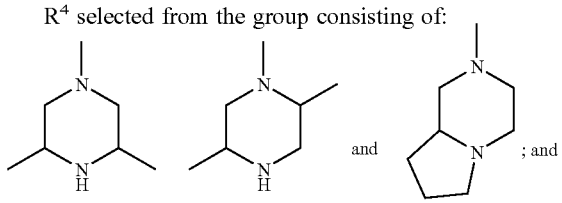

$R^5$ is $C_{1-3}$ alkoxy or a heterocyclic ring selected from the group consisting of:

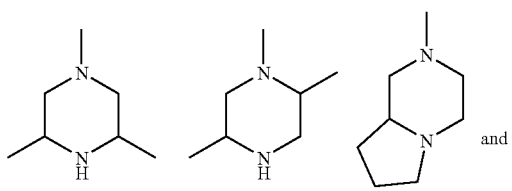

-continued

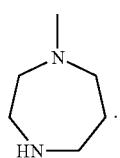

32. A compound according to claim 29, wherein Ar is phenyl, optionally substituted with F, Cl, Br, methyl, $CF_3$, $C_{1-4}$ alkoxyl, $OCF_3$, CN, $NO_2$, phenyloxy, phenyl, methylsulfonyl, or $-NR^7R^8$, where each of $R^7$ and $R^8$ is independently H or methyl.

33. A compound according to claim 29, wherein Ar is 1-naphthyl or 2-naphthyl, each of which is optionally substituted with F, Cl, Br, methyl, $CF_3$, $C_{1-4}$ alkoxyl, $OCF_3$, CN, $NO_2$, phenyloxy, phenyl, methylsulfonyl, or $-NR^7R^8$, where each of $R^7$ and $R^8$ is independently H or methyl.

34. A compound according to claim 29, wherein each of $R^2$ and $R^3$ is H.

35. A compound according to claim 29, wherein $R^4$ is independently a heterocyclic ring selected from the group consisting of:

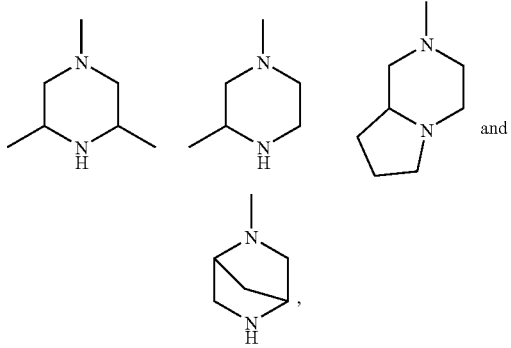

and $R^5$ is independently H or a heterocyclic ring selected from the group consisting of:

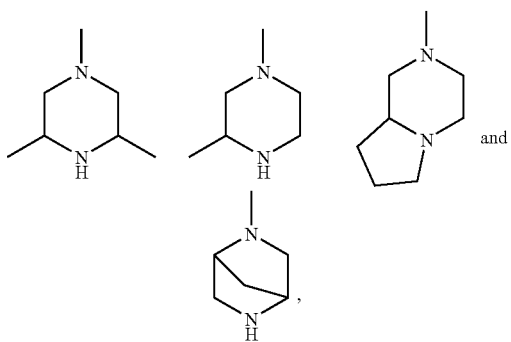

wherein $R^6$ is H, $C_{1-3}$ alkyl, or benzyl.

36. A compound according to claim 29, wherein Ar is phenyl, optionally substituted with F, Cl, Br, methyl, $CF_3$, $C_{1-4}$ alkoxyl, $OCF_3$, CN, $NO_2$, phenyloxy, phenyl, methylsulfonyl, or $-NR^7R^8$ where each of $R^7$ and $R^8$ is independently H or methyl; each of $R^2$ and $R^3$ is H; and $R^4$ is independently a heterocyclic ring selected from the group consisting of:

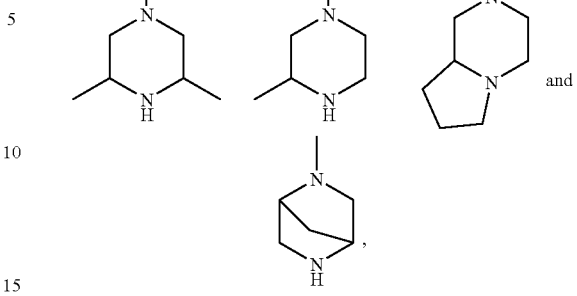

and $R^5$ is independently H or a heterocyclic ring selected from the group consisting of:

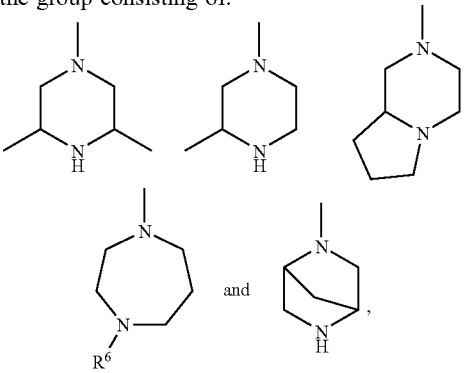

wherein $R^6$ is H, $C_{1-3}$ alkyl, or benzyl.

37. A compound according to claim 29, wherein Ar is 1-naphthyl or 2-naphthyl, each of which is optionally substituted with F, Cl, Br, methyl, $CF_3$, $C_{1-4}$ alkoxyl, $OCF_3$, CN, $NO_2$, phenyloxy, phenyl, methylsulfonyl, or $-NR^7R^8$, where each of $R^7$ and $R^8$ is independently H or methyl; each of $R^2$ and $R^3$ is H; and $R^4$ is independently a heterocyclic ring selected from the group consisting of:

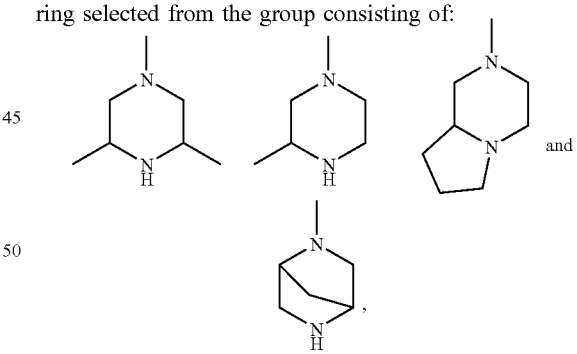

and $R^5$ is independently H or a heterocyclic ring selected from the group consisting of:

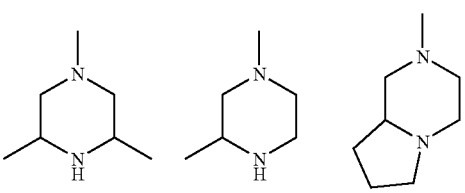

-continued

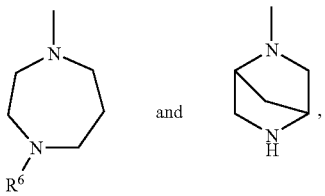
and wherein R⁶ is H, $C_{1-3}$ alkyl, or benzyl.

38. A compound selected from the group consisting of:
4-(5-aza-indolizidinyl)-1-(2-methylbenzenesulfonyl)-1H-indole hydrochloride,
4-(3-methyl-1-piperazinyl)-1-(2-methylbenzenesulfonyl)-1H-indole hydrochloride,
4-(cis-3,5-dimethyl-1-piperazinyl)-1-(2-methylbenzenesulfonyl)-1H-indole hydrochloride,
4-((1S,4S)-2-methyl-2,5-diazabicyclo[2.2.1]heptyl)-1-(2-methylbenzenesulfonyl)-1H-indole hydrochloride,
4-(cis 3,5-dimethyl-1-piperazinyl)-1-(benzenesulfonyl)-1H-indole hydrochloride, and
4-(3-methylpiperazine)-(N-(4-trifluoromethyl)phenylsulfonyl)indole dihydrochloride.

39. A compound of formula (I):

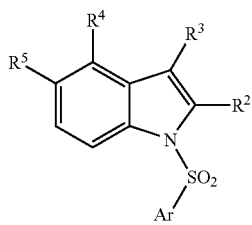

(I)

wherein
Ar is
(1) phenyl, or
(2) naphthyl,
wherein the phenyl or naphthyl ring is optionally substituted with halogen, $C_{1-6}$ alkyl, $CF_3$, hydroxyl, $C_{1-6}$ alkoxyl, $OCF_3$, $COCF_3$, CN, $NO_2$ phenyloxy, phenyl, $C_{1-6}$ alkylsulfonyl, $C_{2-6}$ alkenyl, $-NR^7R^8$, $C_{1-6}$ alkylcarboxyl, formyl, $-C_{1-6}$ alkyl-NH—CO-phenyl, $-C_{1-6}$ alkyl-CO—NH phenyl, —NH—CO—$C_{1-6}$ alkyl, —CO—$NR^7R^8$, or $SR^7$; wherein each of $R^7$ and $R^8$ is independently H or $C_{1-6}$ alkyl; and $R^9$ is $C_{1-6}$ alkyl or $C_{2-6}$ alkenyl, either of which is optionally substituted with phenyl or phenyloxy;

$R^2$ is H, phenyl, I, or $C_{1-6}$ alkyl;
$R^3$ is H or 3-(1-azabicyclo[2.2.2]oct-2-en)yl;
$R^4$ is H or is selected from the group consisting of:

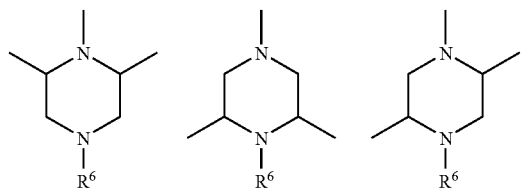

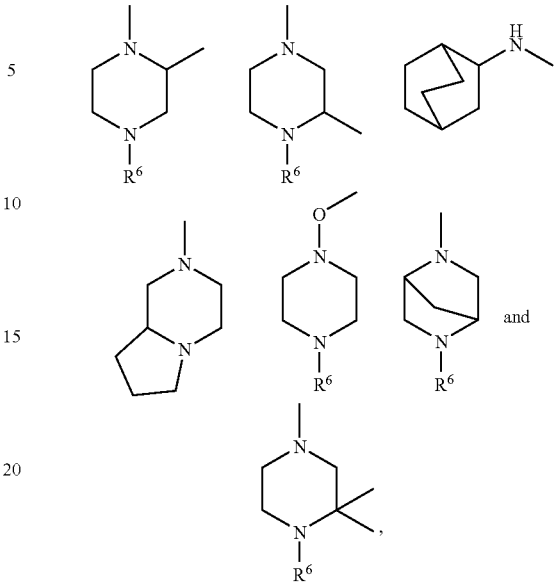

wherein $R^6$ is H, $C_{1-6}$ alkyl, or benzyl; and
$R^5$ is hydroxy, $C_{1-3}$ alkoxy, F, $NO_2$, $CF_3$, $OCF_3$, or is selected from the group consisting of:

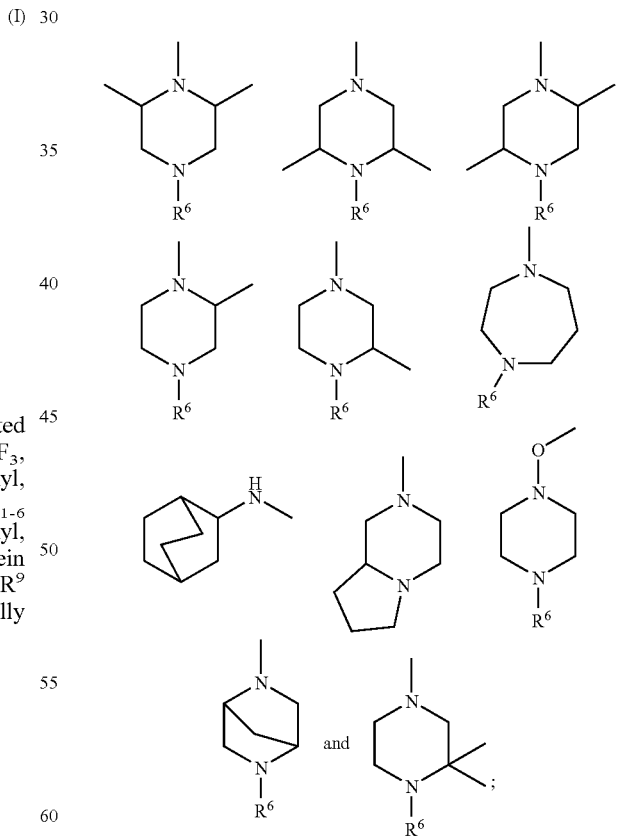

or a pharmaceutically acceptable salt, hydrate, or stereoisomer thereof, with the proviso that when $R^2$ is alkyl, $R^4$ is not H.

40. The compound of claim 29, wherein $R^5$ is H.
41. The compound of claim 39, wherein $R^4$ is H.

42. A compound according to claim 39, wherein R⁴ is independently H or a heterocyclic ring selected from the group consisting of:

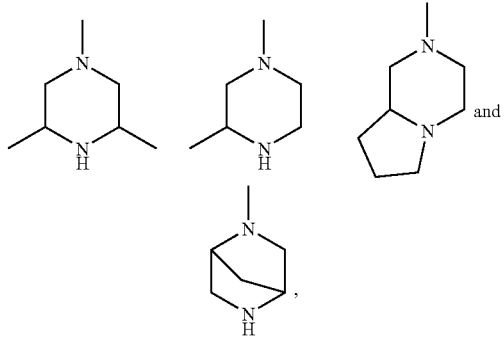

and R⁵ is independently a heterocyclic ring selected from the group consisting of:

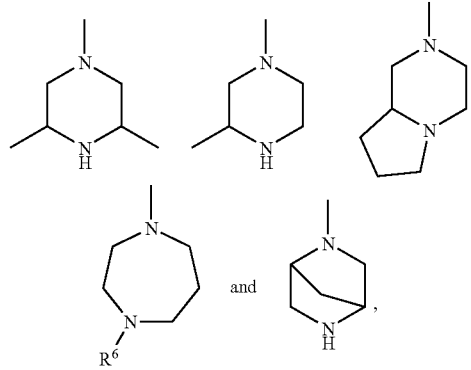

wherein R⁶ is H, $C_{1-3}$ alkyl, or benzyl.

43. A compound according to claim 39, wherein Ar is phenyl, optionally substituted with F, Cl, Br, methyl, CF₃, $C_{1-4}$ alkoxyl, OCF₃, CN, NO₂, phenyloxy, phenyl, methylsulfonyl, or —NR⁷R⁸ where each of R⁷ and R⁸ is independently H or methyl; each of R² and R³ is H; and R⁴ is independently H or a heterocyclic ring selected from the group consisting of:

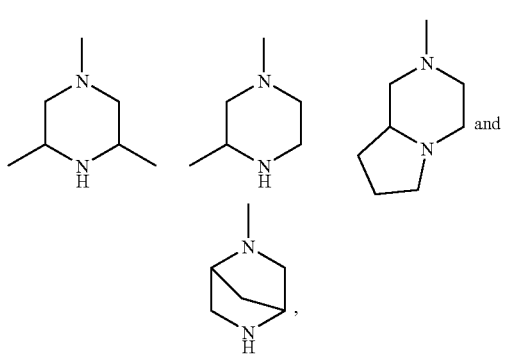

and R⁵ is independently a heterocyclic ring selected from the group consisting of:

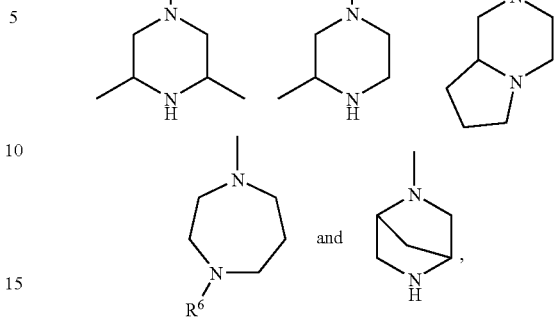

wherein R⁶ is H, $C_{1-3}$ alkyl, or benzyl.

44. A compound according to claim 39, wherein Ar is 1-naphthyl or 2-naphthyl, each of which is optionally substituted with F, Cl, Br, methyl, CF₃, $C_{1-3}$ alkoxyl, OCF₃, CN, NO₂, phenyloxy, phenyl, methylsulfonyl, or —NR⁷R⁸, where each of R⁷ and R⁸ is independently H or methyl; each of R² and R³ is H; and R⁴ is independently H or a heterocyclic ring selected from the group consisting of:

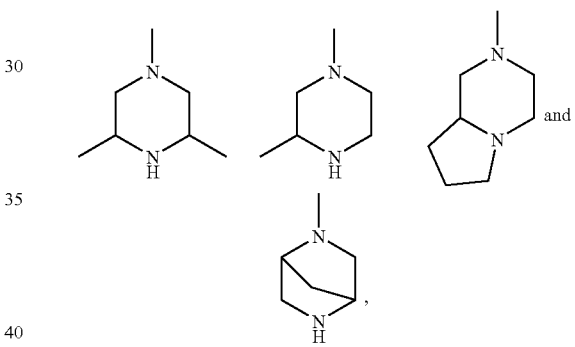

and R⁵ is independently a heterocyclic ring selected from the group consisting of:

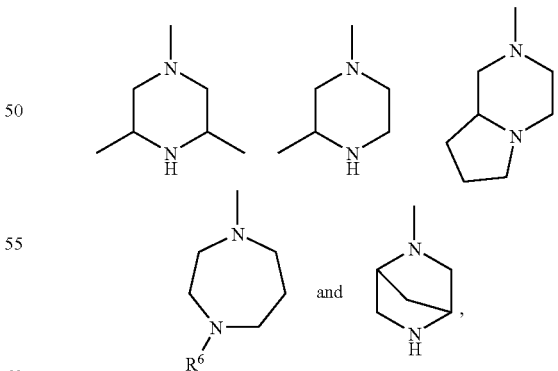

wherein R⁶ is H, $C_{1-3}$ alkyl, or benzyl.

45. The compound according to claim 39, wherein Ar is
(1) phenyl that is unsubstituted or optionally mono- or poly-substituted with halogen, $C_{1-6}$ alkyl, CF₃, hydroxyl, $C_{1-6}$ alkoxyl, OCF₃, CN, NO₂, phenyloxyl, phenyl, alkylsulfonyl, $C_{1-6}$ alkenyl, —$NH_2$, —$NHR^7$, —$NR^7R^8$, $C_{1-6}$ alkylcarboxyl, formyl, —NH—CO—$C_{1-6}$ alkyl, —CO—$NR^7R^8$, or $SR^7$ wherein each of $R^7$ and $R^8$ is independently H or $C_{1-6}$ alkyl;

(2) 1-naphthyl or 2-naphthyl that is unsubstituted or optionally mono- or poly-substituted with halogen, $C_{1-6}$ alkyl, $CF_3$, hydroxyl, $C_{1-6}$ alkoxyl, $OCF_3$, CN, $NO_2$, phenyloxyl, phenyl, alkylsulfonyl, $C_{2-6}$ alkenyl, —$NH_2$, —$NHR^7$, —$NR^7R^8$, $C_{1-6}$ alkylcarboxyl, formyl, —NH—CO—$C_{1-6}$ alkyl, —CO—$NR^7R^8$, or $SR^7$ wherein each of $R^7$ and $R^8$ independently H or $C_{1-6}$ alkyl;

$R^4$ is H or is selected from the group consisting of:

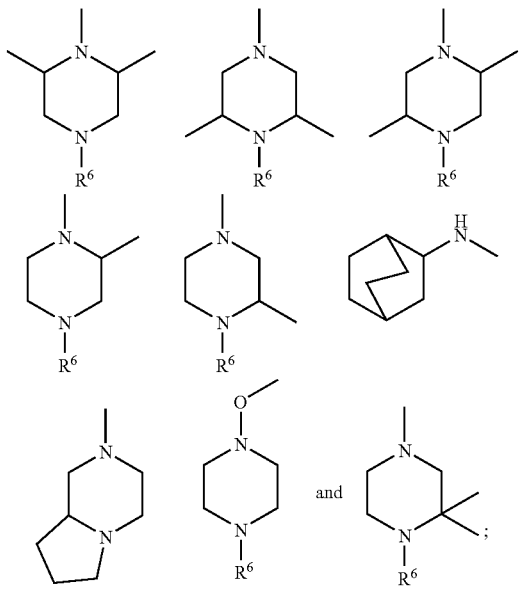

wherein $R^6$ is H, $C_{1-6}$ alkyl, or benzyl; and $R^5$ is hydroxy, $C_{1-3}$ alkoxy, F, $NO_2$, $CF_3$, $OCF_3$ or is selected from the group consisting of:

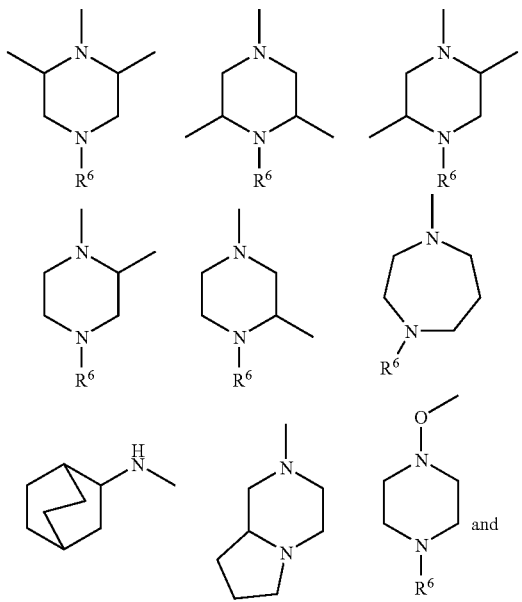

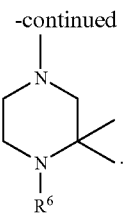

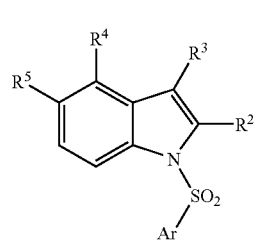

46. A compound of formula (I):

$$\text{(I)}$$

wherein $R^1$ is —$SO_2Ar$; —$SO_2$(alkyl);

Ar is phenyl, optionally substituted with F, Cl, Br, $C_{1-6}$ alkyl, $CF_3$, hydroxyl, $C_{1-6}$ alkoxy, $OCF_3$, $NO_2$, amino, alkylamino, dialkylamino, methylcarboxyl, aminocarbonyl, or $SR^7$; wherein $R^7$ is H or $C_{1-6}$ alkyl; 1-naphthyl, 2-naphthyl;

$R^2$ is H or linear or branched $C_{1-4}$ alkyl;

$R^3$ is H, or 3-(1-azabicyclo[2.2.2]oct-2-en)yl, or 3-quinuclidinyl;

$R^4$ is H or the following amine groups:

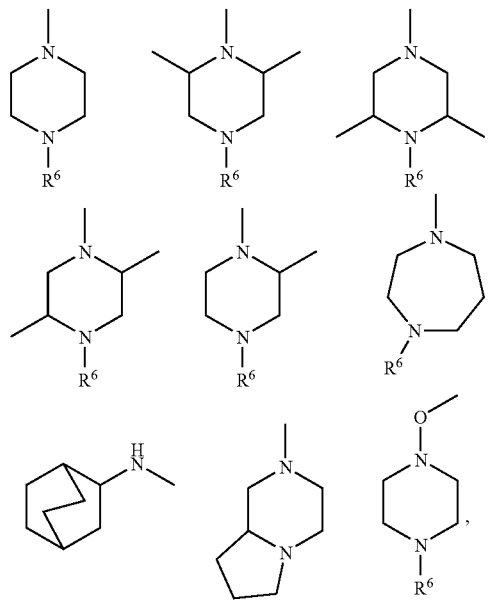

wherein $R^6$ is H or a linear or branched $C_{1-6}$ alkyl; and $R^5$ is $R^4$ or H, hydroxy, $C_{1-3}$ alkoxy, F, $NO_2$, $CF_3$, $OCF_3$;

and pharmaceutically acceptable salts, hydrates, or stereoisomeric forms thereof.

47. The compound according to claim 46, wherein
$R^1$ is —SO$_2$Ar in which Ar is phenyl substituted with F or C$_{1-6}$ alkyl; 1-naphthyl, 2-naphthyl;
$R^2$ is H, propyl;
$R^4$ is selected from the group consisting of:

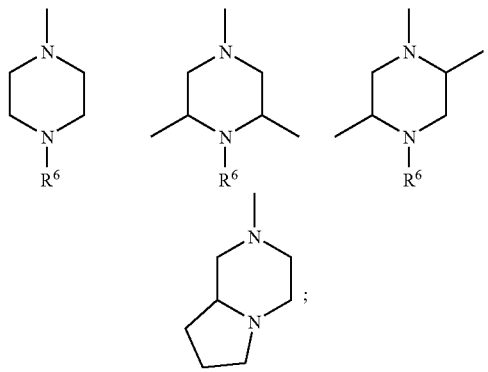

wherein $R^6$ is H; and
$R^5$ is H or C$_{1-3}$ alkoxy.

48. The compound of claim 46, wherein the compound is selected from:
1-(phenylsulfonyl)-4-(1-piperazinyl)-1H-indole,
1-[(4-fluorophenyl)sulfonyl]-4-(1-piperazinyl)-1H-indole,
3-(1-azabicyclo[2.2.2]oct-2-en-3-yl)-1-(phenylsulfonyl)-1H-indole,
5-methoxy-1-(phenylsulfonyl)-4-(1-piperazinyl)-1H-indole,
4-(4-ethyl-1-piperazinyl)-1-(phenylsulfonyl)-1H-indole,
1-[(4-methylphenyl)sulfonyl]-4-(4-methyl-1-piperazinyl)-1H-indole,
1-(phenylsulfonyl)-5-(1-piperazinyl)-1H-indole,
4-(2,5-dimethyl-1-piperazinyl)-1-(phenylsulfonyl)-1H-indole,
4-(2,6-dimethyl-1-piperazinyl)-1-(phenylsulfonyl)-1H-indole,
4-(1,4-diazepan-1-yl)-1-(phenylsulfonyl)-1H-indole,
2-[1-(phenylsulfonyl)-1H-indol-4-yl]octahydropyrrolo[1,2-a]pyrazine1-(2-naphthylsulfonyl)-4-(1-piperazinyl)-1H-indole,
1-(1-naphthylsulfonyl)-4-(1-piperazinyl)-1H-indole,
1-[(4-methylphenyl)sulfonyl]-4-(1-piperazinyl)-1H-indole,
N-(1-azabicyclo[2.2.2]oct-3-yl)-N-{1-[(4-methylphenyl)sulfonyl]-1H-indo-4-yl}amine,
2-ethyl-4-(4-ethyl-1-piperazinyl)-1-[phenyl)sulfonyl]-1H-indole,
4-(2,5-dimethyl-1-piperazinyl)-2-ethyl-1-(phenylsulfonyl)-1H-indole,
4-(2,5-dimethyl-1-piperazinyl)-1-[(4-methylphenyl)sulfonyl]-2-propyl-1H-indole,
4-(4-ethyl-1-piperazinyl)-1-[(4-methylphenyl)sulfonyl]-2-propyl-1H-indole,
4-(4-ethyl-1-piperazinyl)-5-fluoro-1-[(4-methylphenyl)sulfonyl]-1H-indole,
5-fluoro-4-(1-piperazinyl)-1-{[4-(trifluoromethyl)phenyl]sulfonyl}-1H-indole,
5-chloro-1-(phenylsulfonyl)-4-(1-piperazinyl)-1H-indole,
1-[(5-chloro-3-methyl-1-benzothien-2-yl)sulfonyl]-5-methoxy-4-(1-piperazinyl)-1H-indole,
1-[(4-methylphenyl)sulfonyl]-4-(3-methyl-1-piperazinyl)-1H-indole,
1-[(4-methylphenyl)sulfonyl]-4-(piperidinyloxy)-1H-indole, or
2-ethyl-1-(4-methyl-phenylsulfonyl)-4-(1-piperazinyl)-1H-indole.

49. The compound of claim 48, wherein the compound is 1-(phenylsulfonyl)-4-(1-piperazinyl)-1H-indole.

50. The compound of claim 48, wherein the compound is 1-[(4-fluorophenyl)sulfonyl]-4-(1-piperazinyl)-1H-indole.

51. The compound of claim 48, wherein the compound is 1-[(5-chloro-3-methyl-1-benzothien-2-yl)sulfonyl]-4-(1-piperazinyl)-1H-indole.

52. A pharmaceutical composition comprising a compound of claim 1 and a pharmaceutically acceptable carrier.

53. A pharmaceutical composition comprising a compound of claim 15 and a pharmaceutically acceptable carrier.

54. A pharmaceutical composition comprising a compound of claim 27 and a pharmaceutically acceptable carrier.

55. A pharmaceutical composition comprising a compound of claim 28 and a pharmaceutically acceptable carrier.

56. A pharmaceutical composition comprising a compound of claim 29 and a pharmaceutically acceptable carrier.

57. A pharmaceutical composition comprising a compound of claim 38 and a pharmaceutically acceptable carrier.

58. A pharmaceutical composition comprising a compound of claim 39 or 41 and a pharmaceutically acceptable carrier.

59. A pharmaceutical composition comprising a compound of claim 40 and a pharmaceutically acceptable carrier.

60. A pharmaceutical composition comprising a compound of claim 46 and a pharmaceutically acceptable carrier.

61. A pharmaceutical composition comprising a compound of claim 47 and a pharmaceutically acceptable carrier.

62. A pharmaceutical composition comprising a compound of claim 48 and a pharmaceutically acceptable carrier.

63. A method of treatment of schizophrenia or depression comprising administering to a patient in need thereof a therapeutically effective amount of a compound according to claim 1.

64. A method of treatment of schizophrenia or depression comprising administering to a patient in need thereof a therapeutically effective amount of a compound according to claim 15.

65. A method of treatment of schizophrenia or depression comprising administering to a patient in need thereof a therapeutically effective amount of a compound according to claim 27.

66. A method of treatment of schizophrenia or depression comprising administering to a patient in need thereof a therapeutically effective amount of a compound according to claim 28.

67. A method of treatment of schizophrenia or depression comprising administering to a patient in need thereof a therapeutically effective amount of a compound according to claim 29.

68. A method of treatment of schizophrenia or depression comprising administering to a patient in need thereof a therapeutically effective amount of a compound according to claim 38.

69. A method of treatment of schizophrenia or depression comprising administering to a patient in need thereof a therapeutically effective amount of a compound according to claim 39.

70. A method of treating schizophrenia or depression, comprising administering to a patient in need thereof a therapeutically effective amount of a compound according to claim 39.

71. A method of treating schizophrenia or depression, comprising administering to a patient in need thereof a therapeutically effective amount of a compound according to claim 40 or 41.

72. A method of treatment of schizophrenia or depression comprising administering to a patient in need thereof a therapeutically effective amount of a compound according to claim 40.

73. A method of treatment of schizophrenia or depression comprising administering to a patient in need thereof a therapeutically effective amount of a compound according to claim 46.

74. A method of treatment of schizophrenia or depression comprising administering to a patient in need thereof a therapeutically effective amount of a compound according to claim 47.

75. A method of treatment of schizophrenia or depression comprising administering to a patient in need thereof a therapeutically effective amount of a compound according to claim 48.

* * * * *